US012691161B2

(12) United States Patent
Longaker et al.

(10) Patent No.: US 12,691,161 B2
(45) Date of Patent: Jul. 28, 2026

(54) MECHANICAL AND BIOCHEMICAL ACTIVATION AND CONTROL OF SKELETAL STEM CELLS FOR CARTILAGE REGENERATION

(71) Applicant: The Board of Trustees of the Leland Stanford Junior University, Stanford, CA (US)

(72) Inventors: Michael T. Longaker, Atherton, CA (US); Charles K.F Chan, Redwood City, CA (US); Matthew Philip Murphy, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 874 days.

(21) Appl. No.: 17/996,920

(22) PCT Filed: Apr. 27, 2021

(86) PCT No.: PCT/US2021/029459
§ 371 (c)(1),
(2) Date: Oct. 21, 2022

(87) PCT Pub. No.: WO2021/222298
PCT Pub. Date: Nov. 4, 2021

(65) Prior Publication Data
US 2023/0158111 A1      May 25, 2023

Related U.S. Application Data

(60) Provisional application No. 63/017,373, filed on Apr. 29, 2020.

(51) Int. Cl.
| | |
|---|---|
| *A61K 38/18* | (2006.01) |
| *A61K 35/545* | (2015.01) |
| *A61K 38/17* | (2006.01) |
| *A61K 45/06* | (2006.01) |
| *A61L 27/58* | (2006.01) |
| *A61P 19/02* | (2006.01) |
| *C07K 16/28* | (2006.01) |

(52) U.S. Cl.
CPC ........ *A61K 38/1875* (2013.01); *A61K 35/545* (2013.01); *A61K 38/17* (2013.01); *A61K 45/06* (2013.01); *A61L 27/58* (2013.01); *A61P 19/02* (2018.01); *C07K 16/2863* (2013.01); *A61L 2300/412* (2013.01); *A61L 2430/06* (2013.01)

(58) Field of Classification Search
CPC ..... A61K 38/1875; A61K 38/17; A61K 45/06
See application file for complete search history.

(56) References Cited

U.S. PATENT DOCUMENTS

| | | | |
|---|---|---|---|
| 2012/0077743 A1* | 3/2012 | Rueger | A61K 38/18 |
| | | | 514/8.8 |
| 2017/0360838 A1* | 12/2017 | Chan | A61L 27/54 |
| 2019/0336575 A1 | 11/2019 | Longaker et al. | |

OTHER PUBLICATIONS

Murphy et al., Journal of the American College of Surgeons, 2017, vol. 225(4), Suppl. 1, p. S160.*
Murphy et al. (2017) "Activation of the Mouse Resident Skeletal Stem Cell for Articular Cartilage 1-4 Repair," Plastic and Maxillofacial Surgery, vol. 225, Suppl. 1, pp. 1 of 1.
Murphy et al. (2018) "Translational Approach Using Trimodal Manipulation of Resident Skeletal Stem Cells for Articular Cartilage Repair." Journal of the American College of Surgeons, vol. 227, Suppl. 1, pp. S213-S214.
Murphy et al. (2020) "Articular cartilage regeneration by activated skeletal stem cells." Nat Med, vol. 26, pp. 1-39.

* cited by examiner

*Primary Examiner* — Xiaozhen Xie
(74) *Attorney, Agent, or Firm* — Pamela J. Shewood; Bozicevic, Field & Francis LLP

(57) ABSTRACT

Methods and compositions are provided for the regeneration of articular cartilage by activating skeletal stem cells with a combination of (i) mechanical and (ii) biochemical stimulus. The mechanical stimulus can be an acute local injury. The biochemical stimulus can be a combination of an effective dose of a BMP2 activating agent and a VEGF inhibitor.

15 Claims, 42 Drawing Sheets

Actin Cre ER Clonality
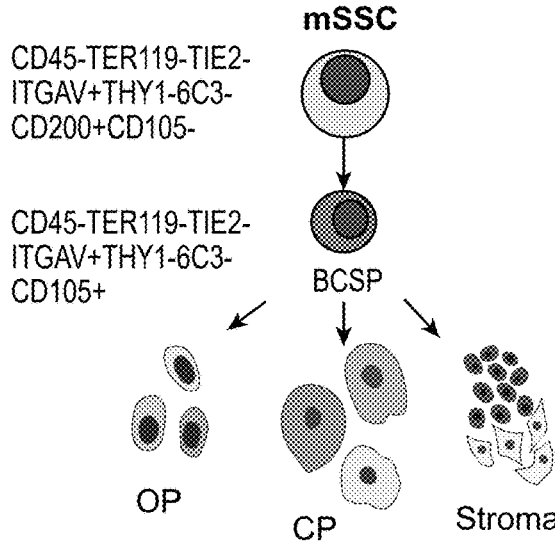
FIG. 1D
FIG. 1E
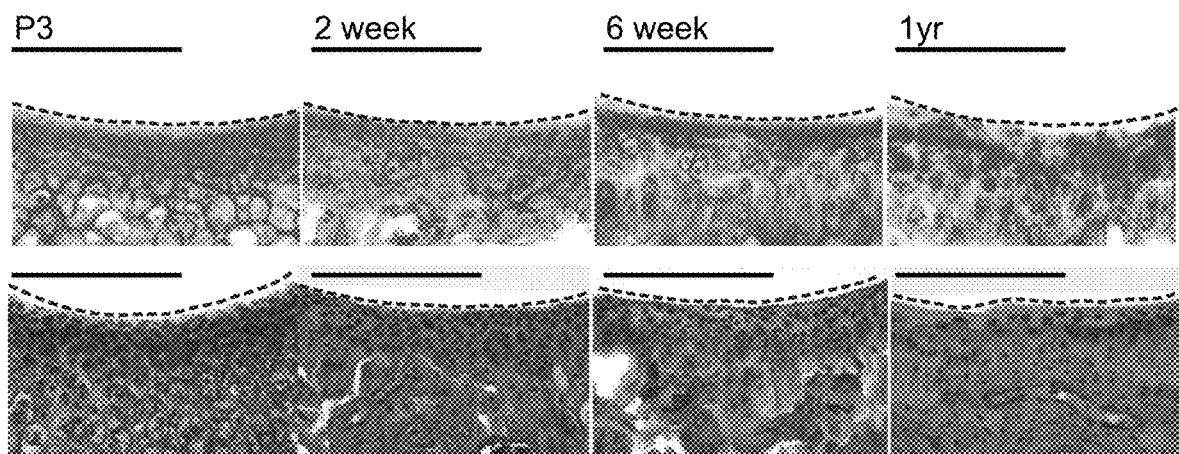
P3          2 week          6 week          1yr
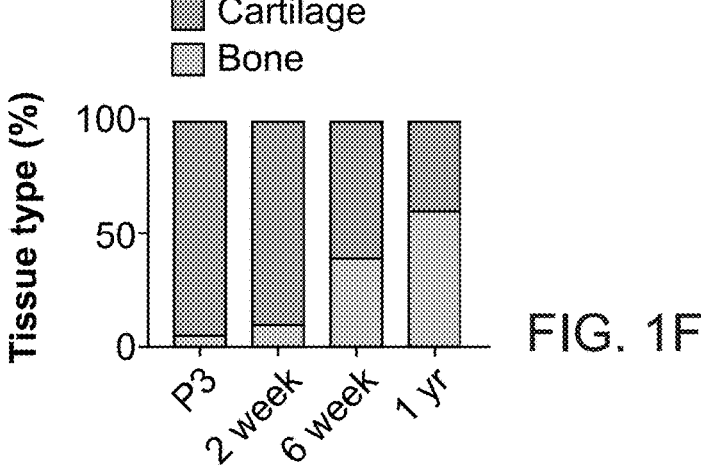
□ Cartilage
□ Bone
FIG. 1F

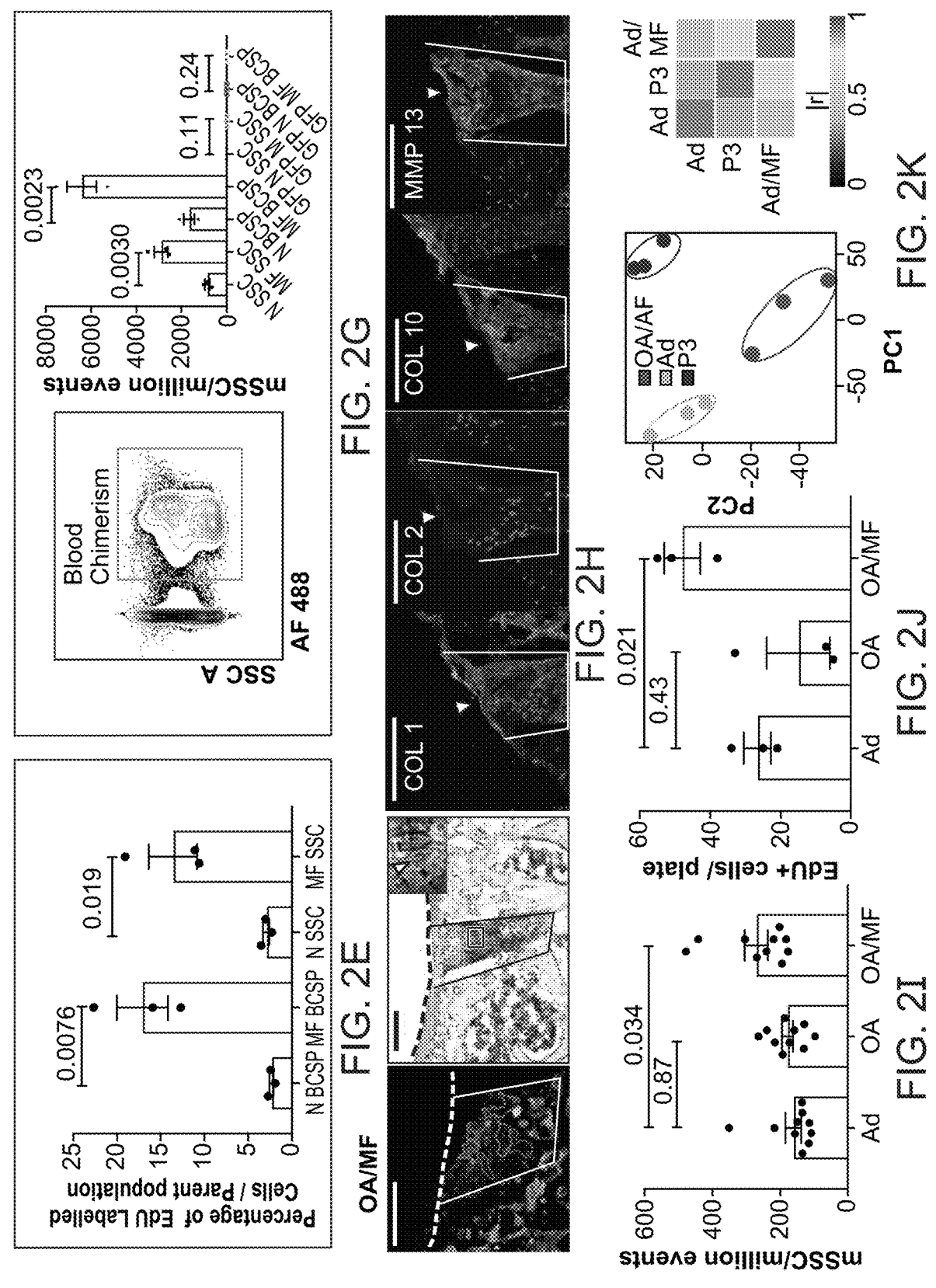

FIG. 3 A-F

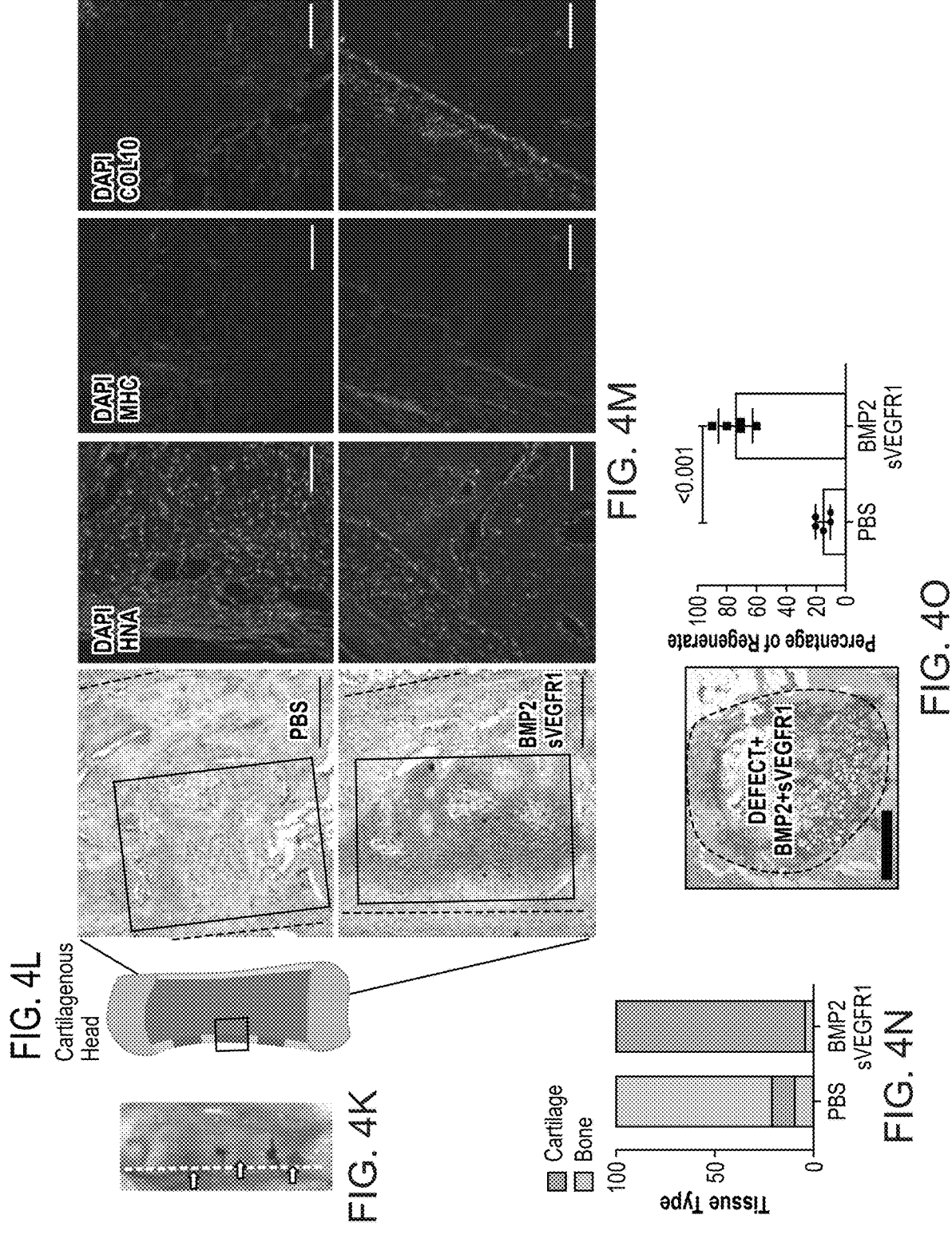

Pathways enriched in the Ad/MF and P3 mSSC populations compared with Ad mSSC.

Enrichment plot: HALLMARK_MYC_TARGETS_V1

Enrichment plot: HALLMARK_PROTEIN_SECRETION

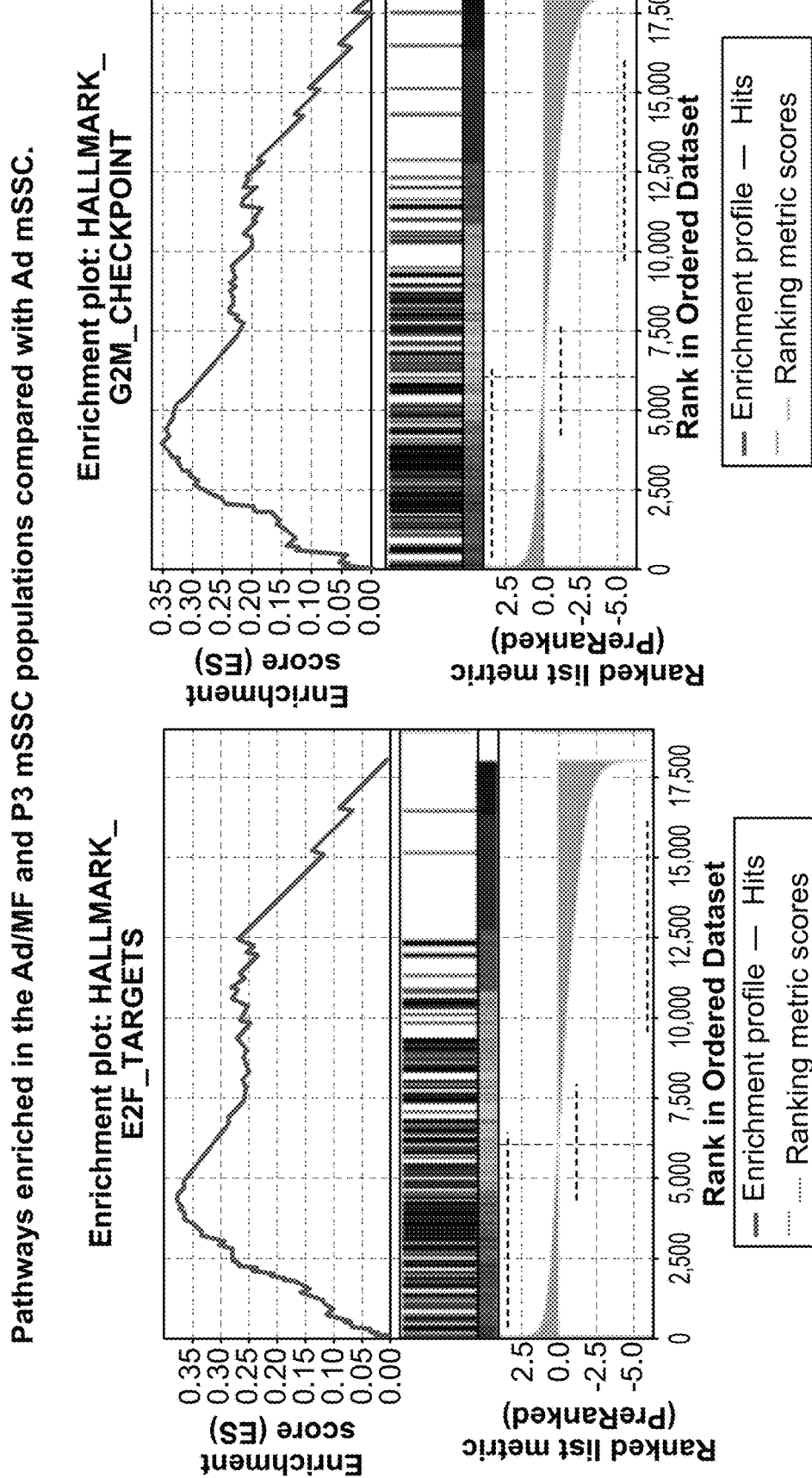
FIG. 6A (Cont. 1)

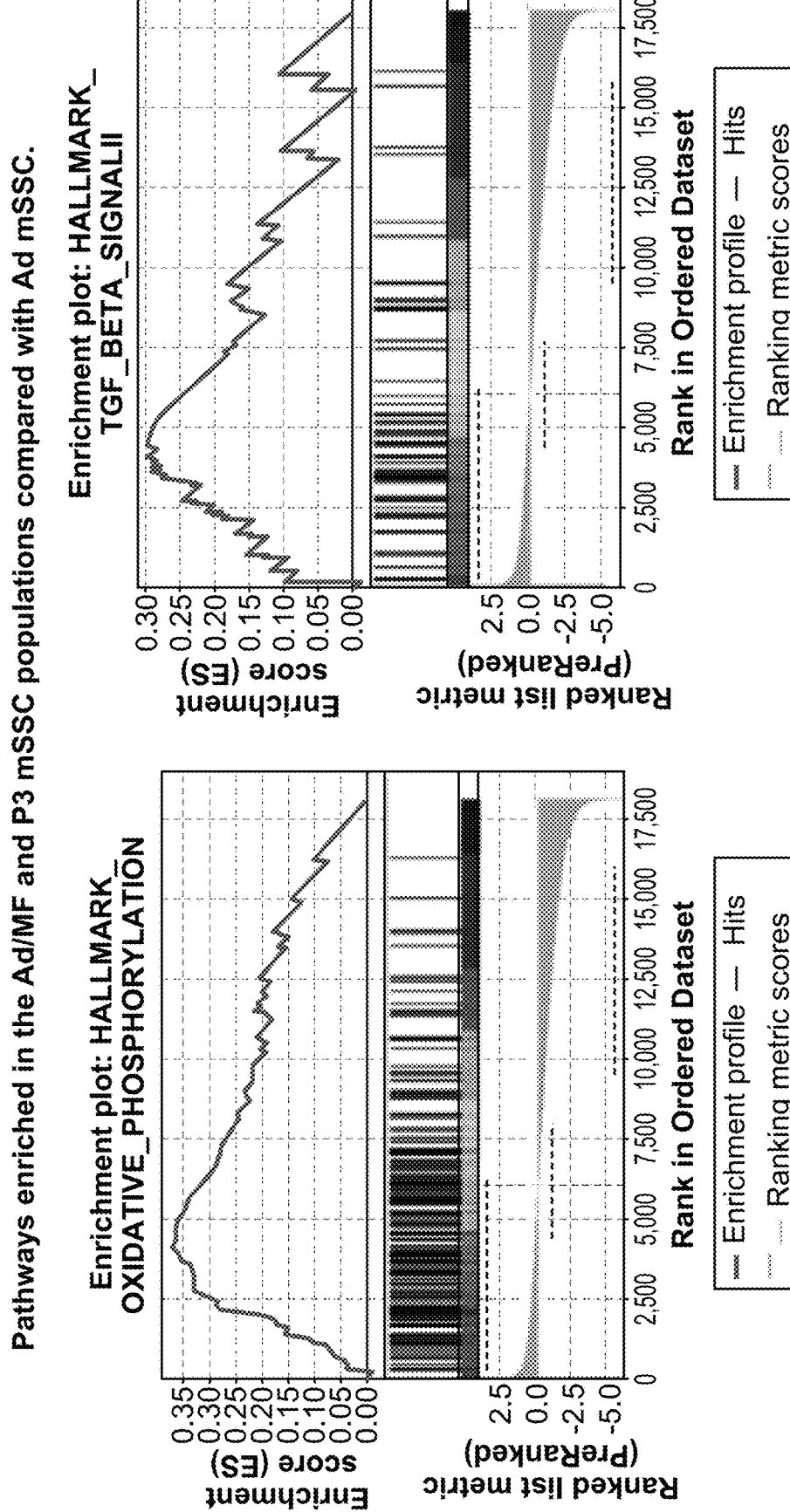
FIG. 6A (Cont. 2)

FIG. 7 A a  Alizarin red assay b Alcian blue assay c Oil red O assay

Schematic of distal femur with each tissue component labelled
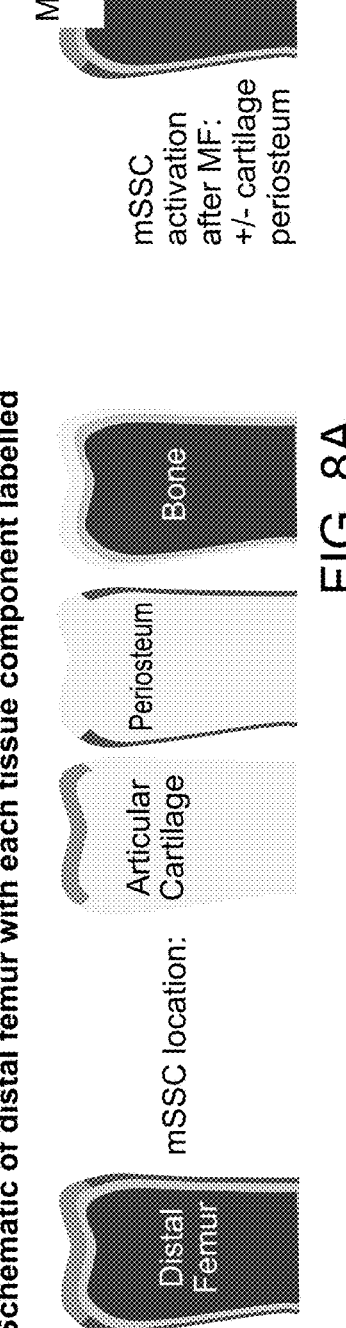
FIG. 8A
FACS diagrams showing relative populations within the major tissue compartments
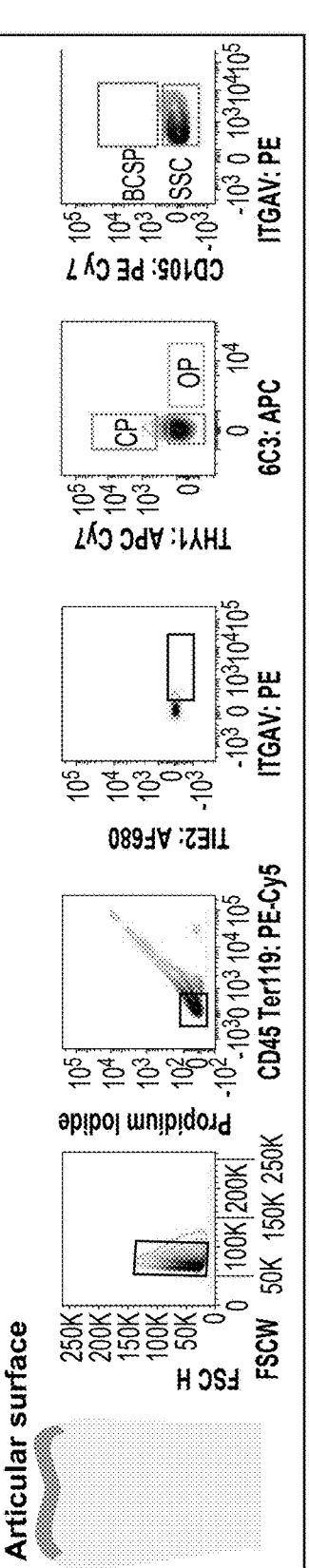
FIG. 8B
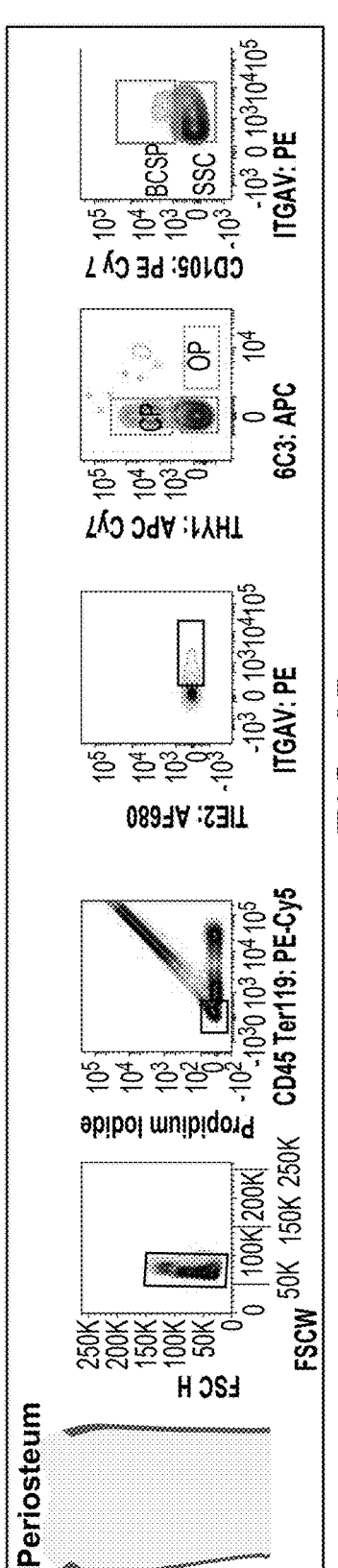

Effect of MF on joints that have been microdissected (removal of articular cartilage and periosteum) vs normal joints.

Graph showing the number of mSSC/ million events in each tissue compartment.

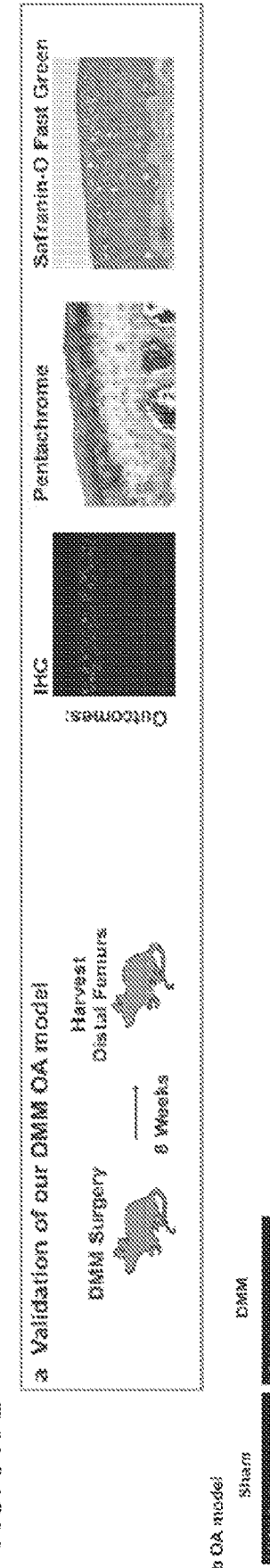
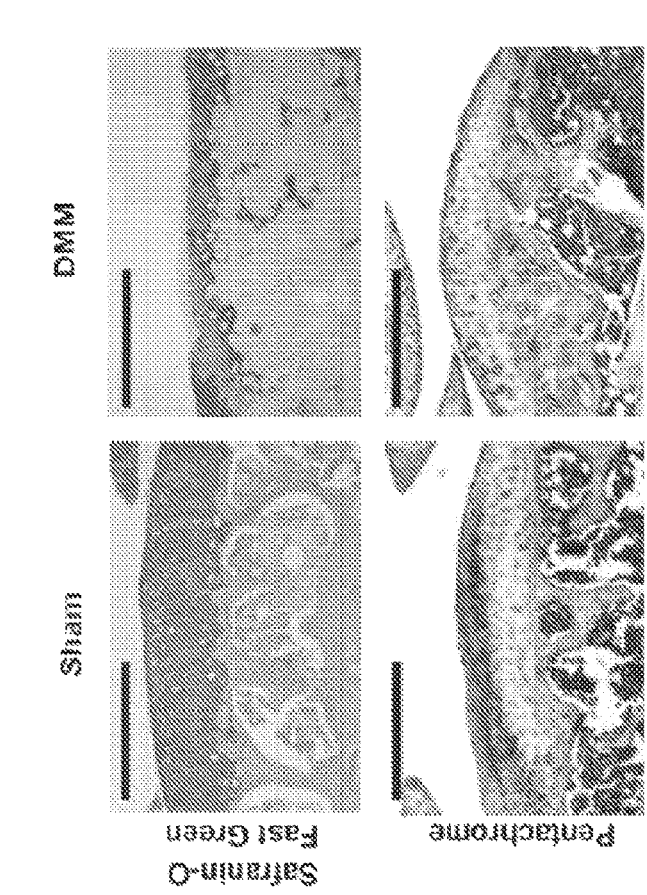
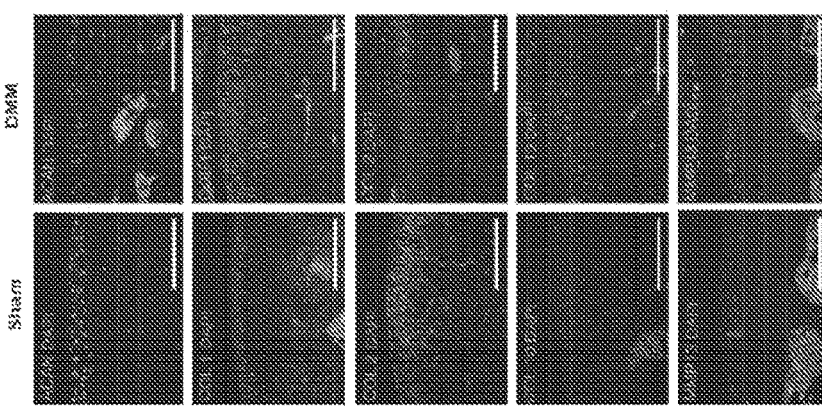
FIG. 9 A-B

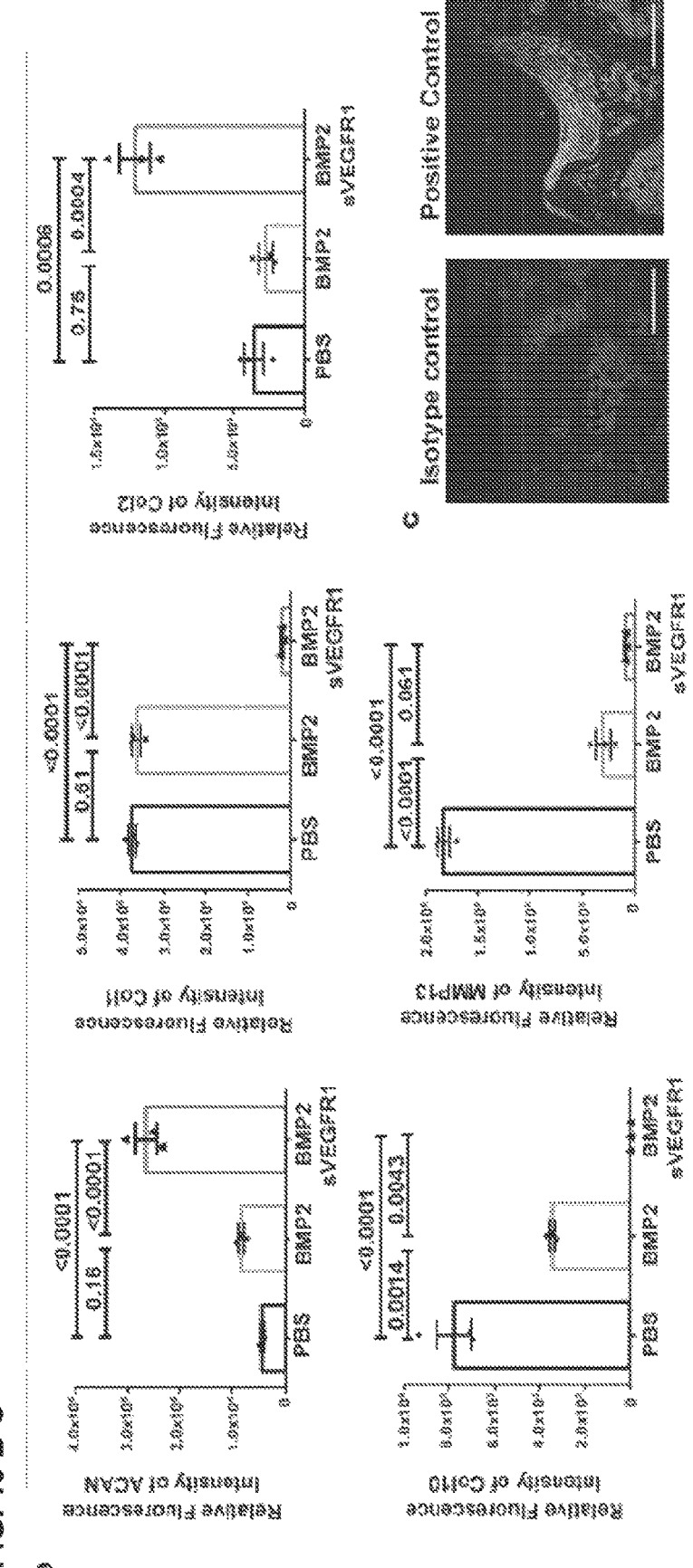

d Repeat examples of BMP2 + sVEGFR1 at 4 weeks

FIG. 11 A

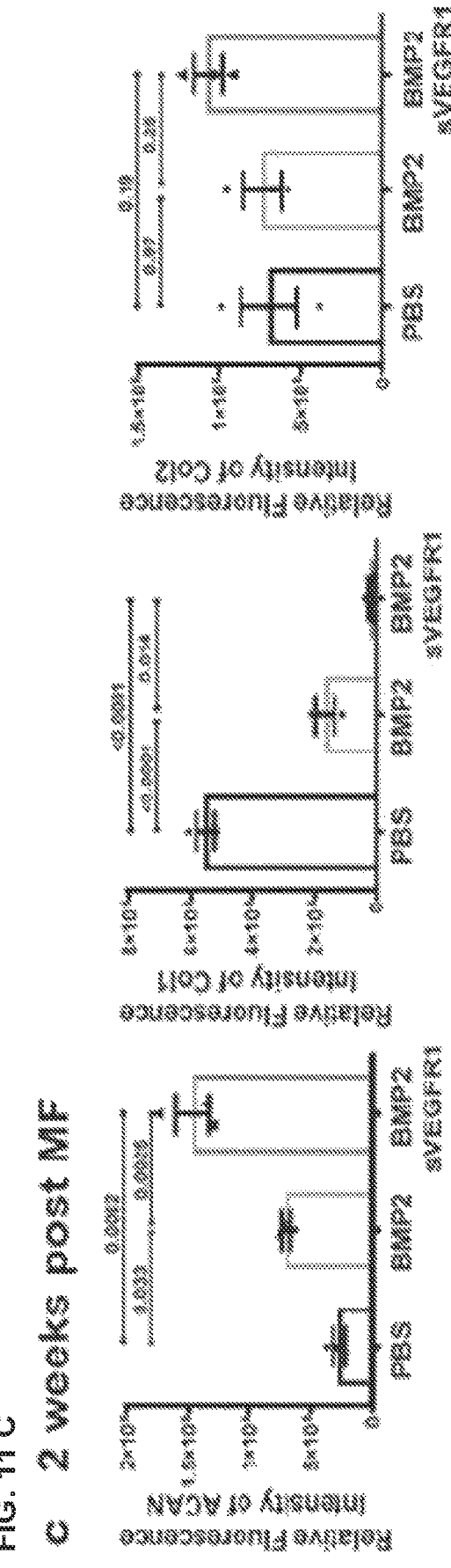
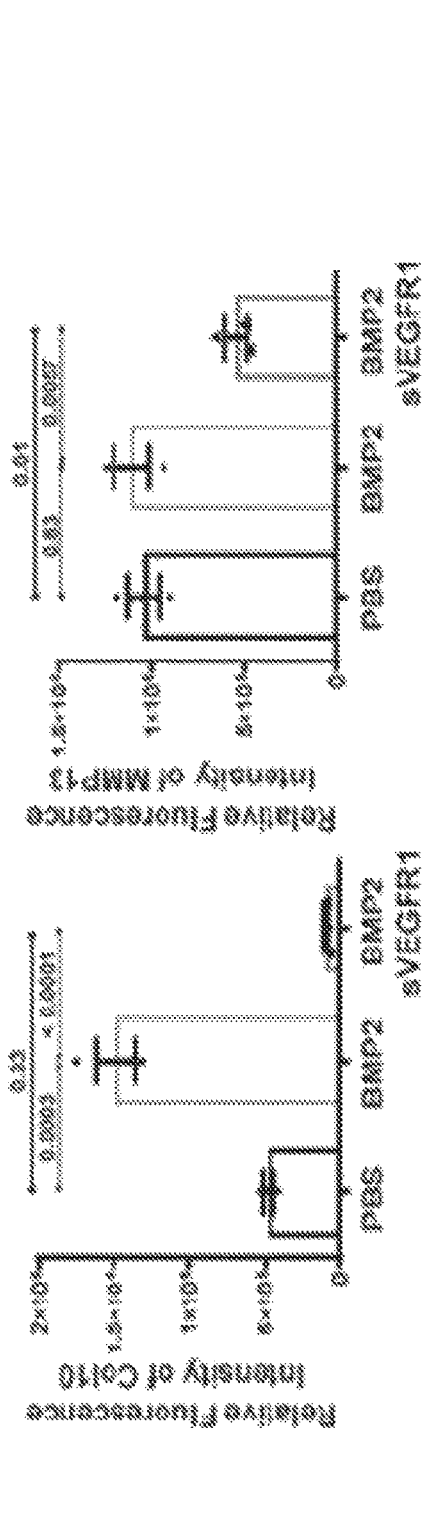
FIG. 11 C
c 2 weeks post MF

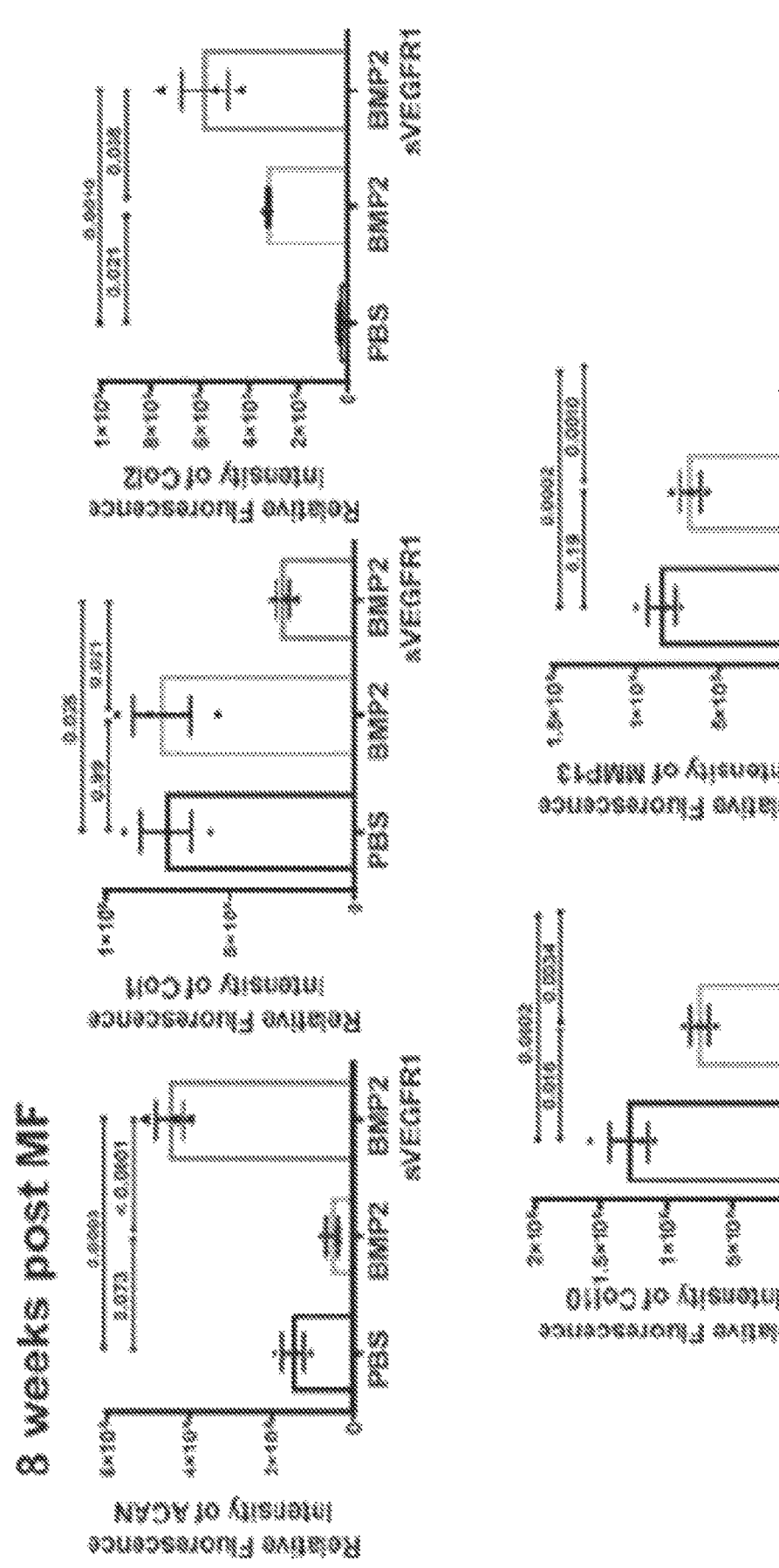
FIG. 11C CON'T
8 weeks post MF

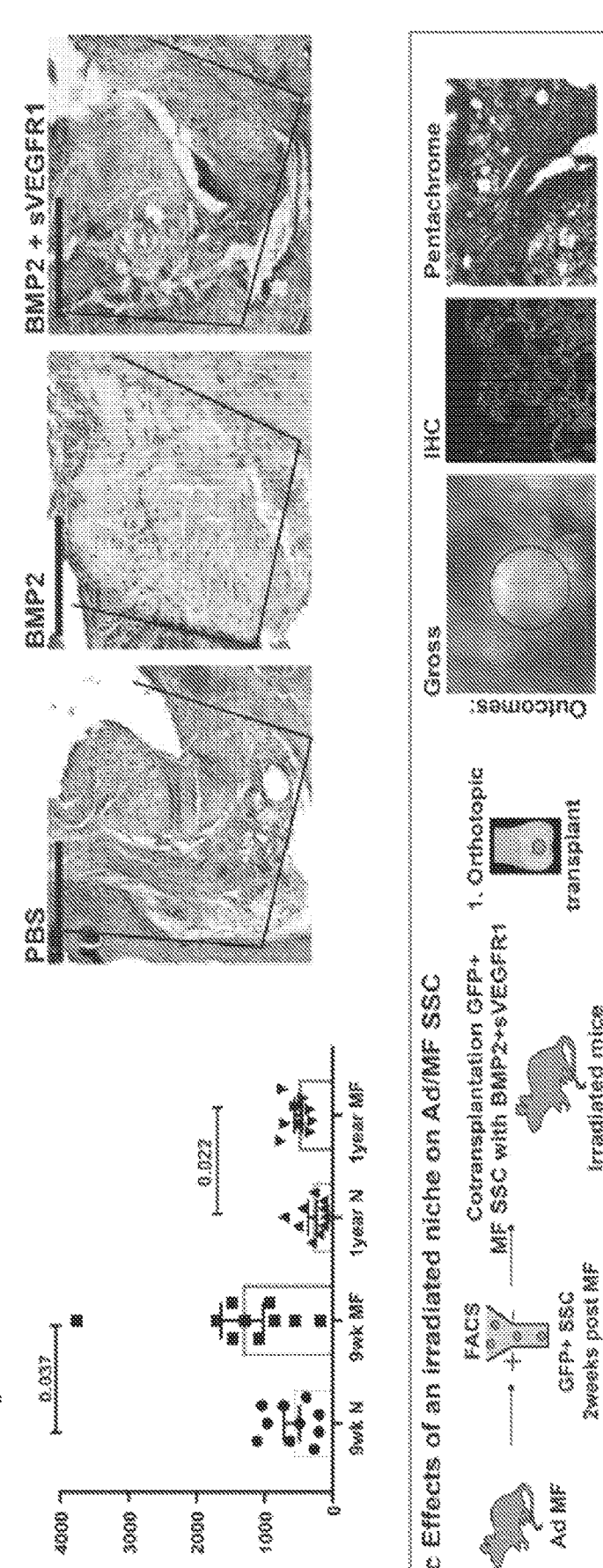
FIG. 13 A-C

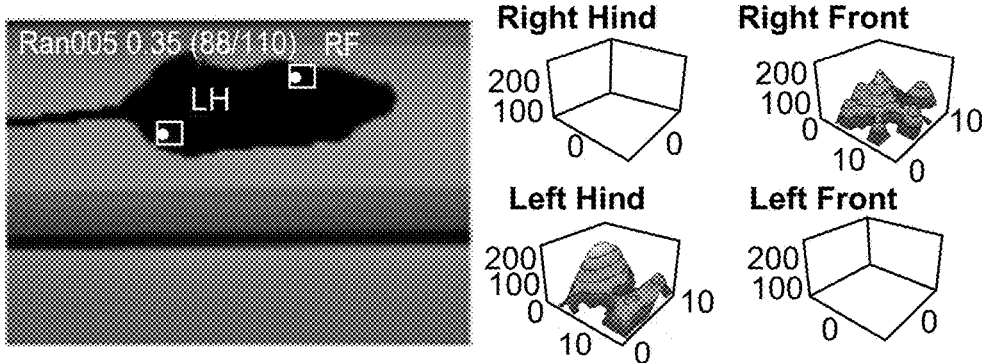
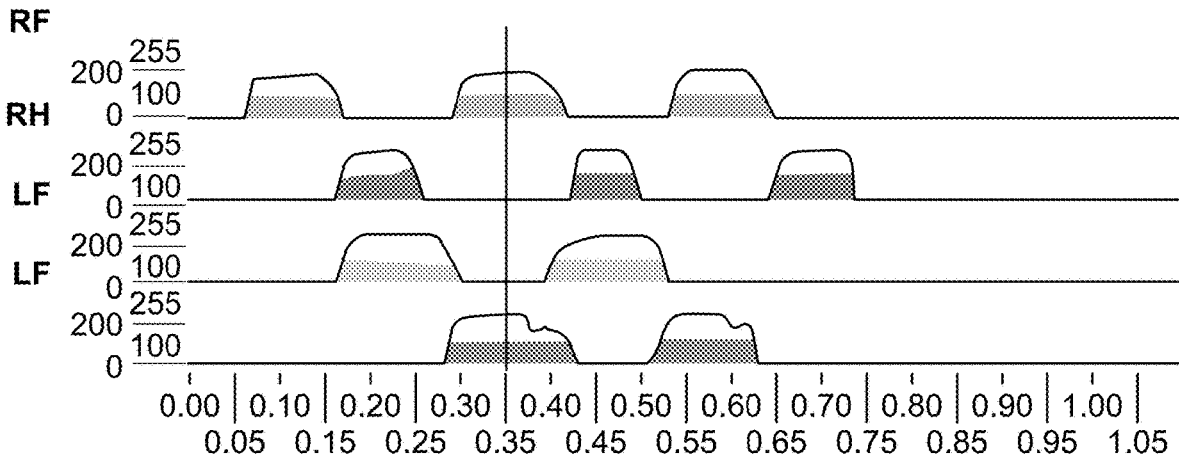
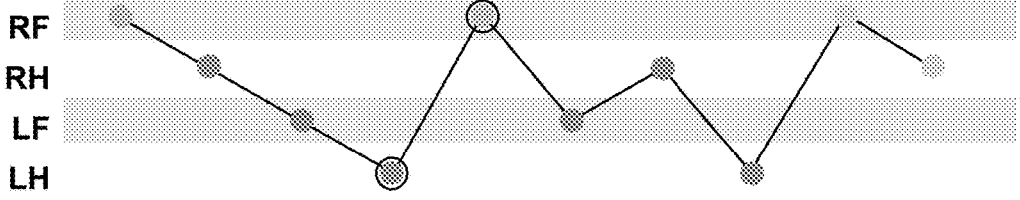
Not taken into account
Start of a pattern
Part of a pattern
Not part of a pattern
FIG. 15A

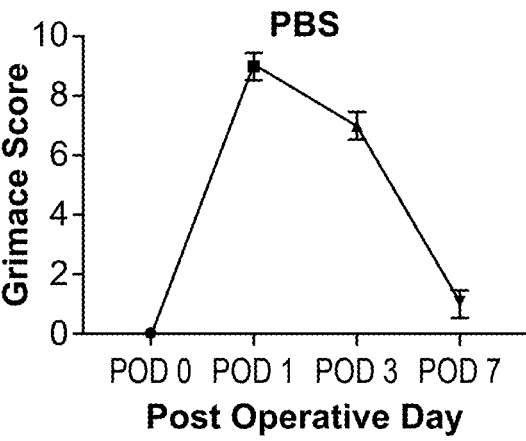
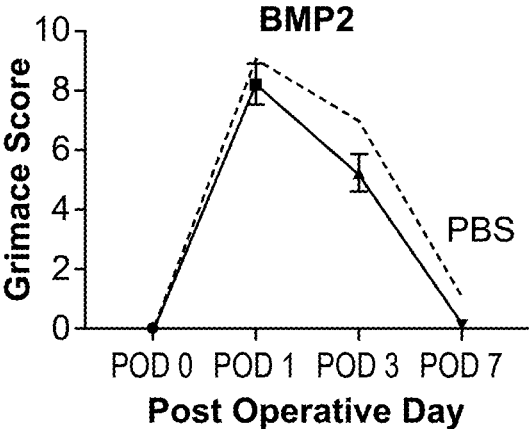
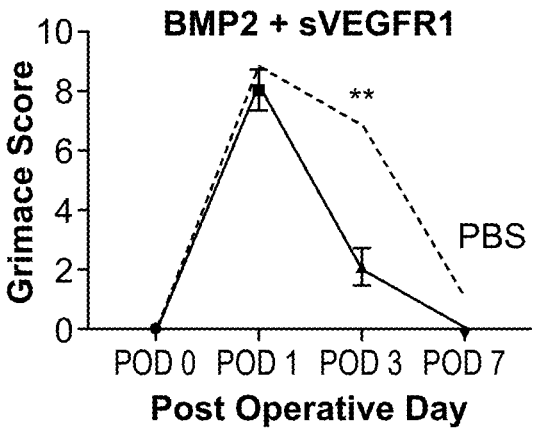
FIG. 15B

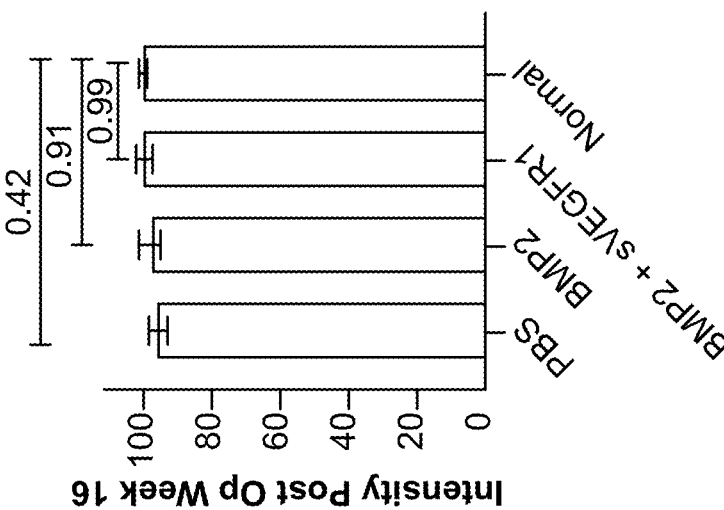
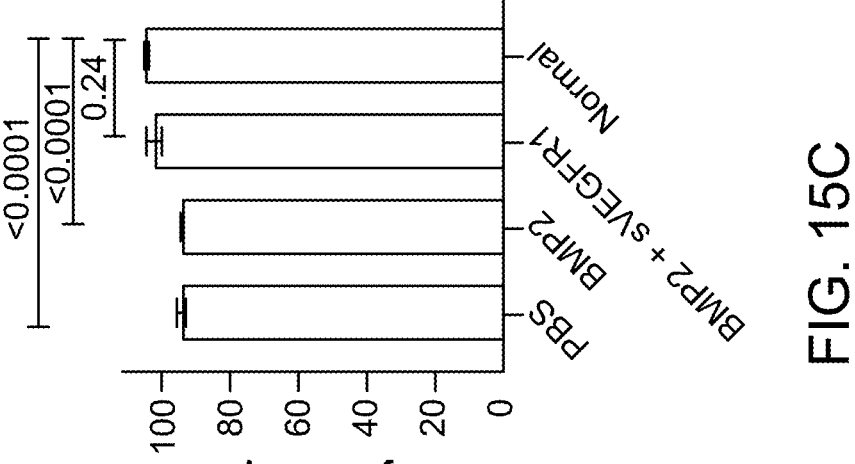
FIG. 15C

MECHANICAL AND BIOCHEMICAL ACTIVATION AND CONTROL OF SKELETAL STEM CELLS FOR CARTILAGE REGENERATION

CROSS-REFERENCE TO RELATED APPLICATION

The present application is a U.S. National Stage of PCT Application No. PCT/US2021/029459, filed Apr. 27, 2021, which claims the benefit of and priority to U.S. Provisional Patent Application No. 63/017,373, filed Apr. 29, 2020, the entire disclosure of which is hereby incorporated by reference herein in their entireties for all purposes.

BACKGROUND

Musculoskeletal disorders are a significant global health burden. Currently 52.2M Americans are diagnosed with arthritis and by 2040 this is estimated to rise to 78.4M. Of these disorders, the most common type is osteoarthritis (OA) which has a lifetime risk of 40%. With no effective treatments yet approved to prevent OA disease progression, symptomatic relief and eventual joint replacement are the standards of care. In an attempt to regenerate cartilage in OA, surgeons perform microfracture (MF) surgery, a technique developed in the 1950's and widely used today. During MF surgery, the surgeon drills into the debrided chondral bone until the marrow cavity is accessed. A hematoma forms at the MF site that is resorbed and replaced with fibrous tissues. The resulting "fibrocartilage" provides some symptomatic relief but has significantly reduced mechanical properties compared to normal articular cartilage 6. Little is known about the mechanism through which MF causes fibrocartilage formation, the effect of this technique on resident stem cell populations, or how this can be leveraged for tissue regeneration.

The limitations of current approaches for addressing OA, including MF, have led to widespread interest in the potential of stem cell therapy for regenerating cartilage. Numerous clinical trials explore the use of autologous stem cell transplantation as alternative therapies for OA of the hip, knee, and thumb. The majority of stem cell-specific trials treating OA of the hip and knee are pilot or feasibility studies investigating the use of plastic-adherent, culture-expanded "mesenchymal stem cells" (MSC). These MSC are derived from bone marrow or adipose tissue. However, these MSC do not constitute validated stem cell populations and it is difficult to ascertain the degree of engraftment by the transplanted cells and their contribution to changes in functional outcomes. The trials also did not reveal specific mechanisms of action behind cases of apparent symptomatic improvement.

More recently, several groups have made progress in identifying skeletal stem cells (SSC) in mice (mSSC) and humans (hSSC). Purified SSC are defined by their ability to self-renew and their multi-lineage contribution to bone, cartilage, and stroma but not fat, however it is important to consider that SSCs using different sorting strategies may be similar but not necessarily the same for instance in their ability to make adipocytes. Furthermore, SSC in the bones of mice and humans are stimulated to proliferate following injury and injury-activated progenitor populations also demonstrate enhanced skeletogenic potential relative to homeostatic populations. However, whether activation of resident SSC can be utilized to regenerate cartilage as a means to treat OA has yet to be determined.

SUMMARY

Compositions and methods are provided for the regeneration of cartilage, e.g. articular cartilage, through mechanical and biochemical activation of skeletal stem cells (SSC). It is shown herein that in adult individuals, mature articular cartilage tissues contain reservoirs of SSC, although in reduced numbers relative to neonates and juveniles. These resident pools of SSC can be activated in response to local acute injury, e.g. injury at bone tissue adjacent to articular cartilage, and once activated can be guided to form cartilage by contact with appropriate growth factors. Appropriate growth factors enhance proliferation of SSC; and repress osteogenic and fibroblastic as the SSC differentiate, resulting in a chondrogenic fate and regeneration of cartilage.

In some embodiments the local acute injury, which provides mechanical activation of endogenous SSC, is provided by a microfracture/drilling procedure to bone tissue at the desired site for cartilage regeneration. Microfracture (MF) is a minimally invasive surgery that promotes bleeding from a bone to create a clot in a cartilage defect. Following MF, there is a therapeutic window of to skew MF-activated SSC differentiation fate towards robust formation of cartilage, e.g. immediately following the injury, within 1 hour, within 2 hours, within 4 hours, within 6 hours, within 12 hours, within 1 day, within 2 days, within 3 days. Combining microfracture with the provision of suitable growth factors for SSC proliferation and differentiation to cartilage within the therapeutic window provides for regeneration of stable articular cartilage at the site. The cartilage thus formed has substantially reduced levels of fibrocartilage, relative to the levels seen in the absence of the growth factors.

In some embodiments, activated SSC at a site of local acute injury are contacted with an effective dose of a BMP2 activating agent and a VEGF inhibitor. In some embodiments activated SSC at a site of local acute injury are contacted with an effective dose of a BMP2 activating agent and a VEGF inhibitor as the sole active agents in a drug delivery device. In some embodiments a drug delivery device comprising as the sole active agents BMP2 and a VEGF inhibitor, is implanted at a site of local acute injury.

In some embodiments a drug delivery device for use in the methods described herein is provided. In some embodiments the drug delivery device comprises a dose of a BMP2 activating agent and a VEGF inhibitor effective for regeneration of cartilage at a site of local acute injury, the drug delivery device comprises a dose of a BMP2 activating agent and a VEGF inhibitor as the sole active agents, effective for regeneration of cartilage at a site of local acute injury. In some embodiments the drug delivery device is a biocompatible hydrogel. In some embodiments the drug delivery device is a biodegradable hydrogel.

In some embodiments the effective dose of BMP2 protein in a single drug delivery device, e.g. an implant, is from about 1 μg to about 50 mg. For delivery to a human, the dose may be from about 10 μg, from about 25 μg, from about 50 μg, from about 100 μg, up to about 50 mg, up to about 25 mg, up to about 10 mg, up to about 5 mg, up to about 1 mg.

The dose of VEGF inhibitor may vary with the specific agent, e.g. small molecule, antibody, soluble VEGFR1, etc. Examples of useful VEGF inhibitors include, without limitation, ziv-aflibercept; bevacizumab; pazopanib; cabozantinib; sunitinib; sorafenib; axitinib; lenvatinib; regorafenib; ponatinib; cabozantinib; vandetanib; ramucirumab; bevacizumab; bevacizumab; and the like. In some embodiments the effective dose of VEGF inhibitor in a single drug delivery device, e.g. an implant, is from about 0.1 µg to about 50 mg. For delivery to a human, the dose may be from about 0.1 µg, from about 0.5 µg, from about 1 µg, from about 25 µg, up to about 10 mg, up to about 5 mg, up to about 2.5 mg, up to about 1 mg.

In some embodiments the drug delivery device is implanted at the site of local acute injury in the absence of exogenous cells. In other embodiments, particularly in the treatment of aged individuals, for example humans over the age of 50, over the age of 60, over the age of 70, etc., an effective dose of skeletal or non-skeletal stem cells are provided with the active agents, where the skeletal or non-skeletal stem cells are optionally allogeneic.

In embodiments, methods are provided for regeneration of articular cartilage at a targeted site in a subject in need thereof. In a first step, a local acute injury is applied to a targeted site for articular cartilage regeneration. In some embodiments the injury is caused by a microfracture procedure, e.g. with an awl, drill, etc. as known in the art. Following the acute local injury, a drug delivery device is implanted at the site of the acute local injury, the device configured to release an effective dose of a BMP2 agent, and a VEGF inhibitor. The device may be implanted immediately following the injury, within 1 hour, within 2 hours, within 4 hours, within 6 hours, within 12 hours, within 1 day, within 2 days, within 3 days. The drug delivery device is optionally a biodegradable matrix, e.g. a hydrogel, that does not need to be removed following cartilage regeneration. The surgical site is closed, and function may be assessed after about 1 week, after about 2 weeks, after about 3 weeks, after about 4 week, after about 6 weeks, after about 8 weeks, or more, as needed, and may be assessed at multiple time points.

In some cell transplantation embodiments, factors and cocktails of factors are provided for directing skeletal stem cells to a chondrogenic fate, which factor(s) may be provided in vitro or in vivo. It is shown that inhibiting VEGF signaling drives SSCs to undergo differentiation into cartilage tissues. In some embodiments an effective dose of a VEGF inhibitor is provided to an individual in combination with an effective dose of SSC for regeneration of cartilage at the site of an acute local injury. In other embodiments, an effective dose of a VEGF inhibitor is provided to an individual with combination with an effective dose of adipose stem cells and BMP2 for regeneration of cartilage at the site of an acute local injury.

BRIEF DESCRIPTION OF THE DRAWINGS

FIG. 3. Manipulating the adult articular microenvironment to facilitate mSSC-derived chondrogenesis. a, Schematic showing the experimental outline to assess cell intrinsic changes following Adult (Ad) vs. Ad/MF. b, Four panels showing the histological differences after transplantation of Ad and Ad/MF GFP+mSSC into renal capsule. Brightfield (Top left) and IF (Lower left) show gross images of 2 grafts confirming the presence of GFP+ cells. Right panels (Top: Ad; Lower: Ad/MF) show pentachrome of sections. Scale bar 100 μm. N=4. c, Four panels showing the histological differences after transplantation of Ad and Ad/MF GFP+ mSSC orthotopically. Brightfield (Top left) and IF (Lower left) show gross images confirming the presence of GFP+ cells. Right panels (Top: Ad; Lower: Ad/MF) show pentachrome images of sections. Scale bar 500 μm. N=4. d, Panels showing the abundance of GFP+Ad/MF mSSC (Left panels) compared to GFP+Ad mSSC (Right panels) within the regenerate. Fibrocartilage confirmed by IF with COL 1 (Panel 1), COL 2 (Panel 2), COL10 (Panel 3), and MMP 13 (Panel 4). Scale bar 500 μm. e, Schematic showing the experimental design to assess cell extrinsic effects of the niche. f, Movat's pentachrome staining of Ad/MF renal capsule transplants. Left panels show low magnification (scale bar 1 mm) with region of interest (ROI) denoted by a black single arrow. Right panels show higher magnification of ROI. Scale bar 500 μm. Left panels: BMP2, Right panels: BMP2+sVEGFR1. N=4. g, OA/MF with factors. Top row: PBS, middle row: BMP2, Lower row: BMP2+sVEGFR1. (L-R: Gross images, Movat's pentachrome, higher magnification of corresponding sections.) Scale bar 500 μm. N=8. h, Tissue regeneration. Top panel: a schematic of defect outlined in dotted orange line and an outline of the regenerate in blue line. Percentage regeneration calculated 18 as 100(A/A+B). Middle panel: Graph showing a significant increase in percentage regeneration with BMP2 and BMP2+ sVEGFR1 compared to PBS. Graph shows Mean+/−SEM. Ordinary one-way ANOVA test (p=<0.0001) with post-hoc analysis using Šidák method to compare between specific means. Exact P values to 2 significant figures shown. Lower panel: Schematic graph showing the tissue composition changes with PBS, BMP2 and BMP2+sVEGFR1. Yellow signifies bone and blue signifies cartilage within the regenerate.

FIG. 15. Functional assessment. a, Schematic of the experimental assessment. b, Grimace assessment scores for adult mice following MF surgery of the distal femur with 3 conditions (Upper-lower: PBS, BMP2, BMP2+sVEGFR1). Graphs show Mean+/−23 SEM. Ordinary one-way ANOVA test (p=<0.0001) with post-hoc analysis using Šidák method to compare between specific means. Exact P values to 2 significant figures. c, Gait assessment scores for maximum contact mean intensity (Left) and mean intensity (Right) of the right hind (RH) (Upper) and the left hind (LH) (Lower) limbs with 4 conditions (PBS, BMP2, BMP2+sVEGFR1, and Uninjured).

DETAILED DESCRIPTION OF THE EMBODIMENTS OF THE INVENTION

Figures 1A, 1B, 1C:
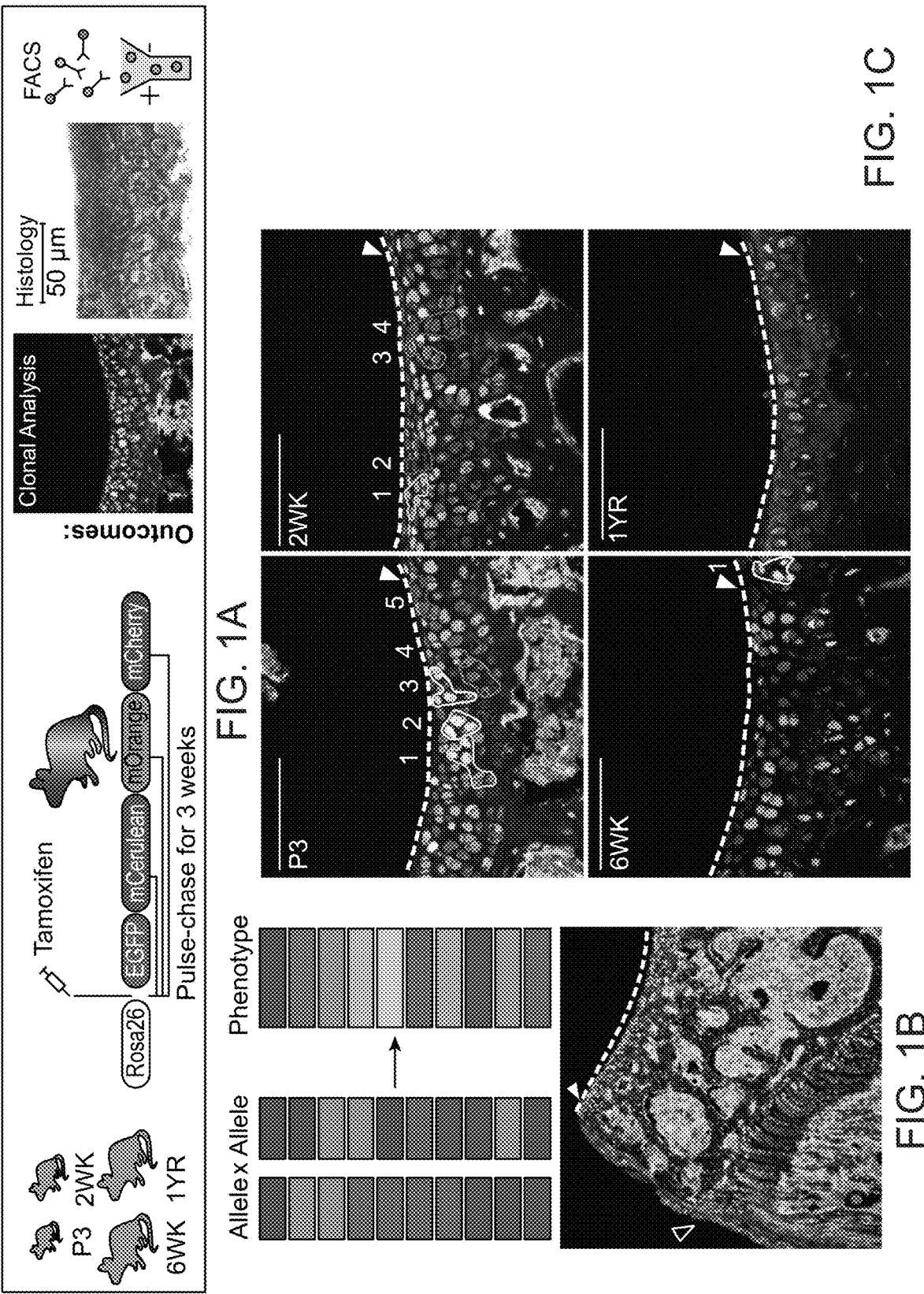
FIG. 1. Maturity leads to a reduction in articular mouse skeletal stem cells (mSSC). a, Schematic showing the experimental outline. b, Top panel: Schematic of the potential colors following recombination of the Actin-CreER rainbow mouse model with a stochastic labelling of 10 potential colors. Lower panel: Low magnification of the distal femur showing clonality at the growth plate (white outline arrow) and articular surface (white solid arrow) of a P3 pup. c, Four panels showing confocal images of articular surfaces (white solid arrow and dotted white line) with clones outlined in respective colors. (Top left: P3, Top right: 2 WK, Lower left: 6 WK, Lower right: 1 YR). Scale bar 20 µm. d, Graph showing a decline in the number of clones per high power field (HPF) with age. Ordinary one-way ANOVA test (p=<0.0001) with post-hoc analysis using Šidák method to compare between specific means. N=5. e, Schematic showing the mSSC hierarchy. f, Pentachrome images showing the changes in morphology of articular cartilage with maturity. (Left-Right: P3, 2 WK, 6 WK, 1 YR). Scale bar 100 µm. Schematic graph representing the change in composition of the articular surface with age (yellow=bone, blue=cartilage). g, Flow cytometry showing the gating of our mSSC populations. Top panel: P3. Lower panel: Adult. Populations of mSSC are higher within the P3 mice as Thy1-6C3-populations are much higher at 95.9% vs. 57.6% in the aged mice. h, Top panel: Graph showing the reduction in mSSC per million events after FACS from P3 vs. Adult (Ad) mice. N=10. Lower panel: Graph showing a significant reduction in colony forming ability in Adult mice. N=6. Graphs unless otherwise stated show Mean+/− SEM. Student T-test. Exact P values to 2 significant figures shown.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, compositions and kits for regenerating articular cartilage at a targeted site in vivo are provided. In some embodiments, compositions and methods are provided for directing differentiation of mammalian skeletal stem cells into articular cartilage through mechanical and biochemical stimulation. The biochemical factors can be provided systemically or as a localized implant. In some embodiments the factors are BMP2 and a VEGF inhibitor. In some embodiments BMP2 and a VEGF inhibitor are provided in the absence of other factors. In some embodiments BMP2 and a VEGF inhibitor are provided at the site of a microfracture. In some embodiments no exogenous cells are provided, i.e. only the resident SSC are activated. Optionally the resident SSC may be augmented with provision of exogenous cells, e.g. SSC or non-skeletal stem cells. In some embodiments the BMP2 and VEGF inhibitor are provided in a unit dose of a drug delivery implant, which is positioned at the targeted site.

These and other objects, advantages, and features of the invention will become apparent to those persons skilled in the art upon reading the details of the subject methods and compositions as more fully described below.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Microfracture. Microfracture is a surgical technique that has been developed to treat chondral defects, which are damaged areas of articular cartilage of the knee. It is a common procedure used to treat patients with full thickness damage to the articular cartilage that goes all the way down to the bone. Microfracture has been used in joints including, without limitation, shoulder, hip, ankle and knee.

A microfracture is performed as part of arthroscopic surgery. The area undergoing microfracture is prepared by removing any loose or damaged cartilage. Ideally, the area undergoing microfracture will be less than about 2 centimeters in diameter and have good, healthy surrounding cartilage. Then, a small, sharp pick (awl) or drill is used to create the small microfracture holes in the bone. The number of microfractures created depends on the size of the joint are being treated. Most patients with a 1- to 2-centimeter area of damage require five to 15 small microfracture holes in the bone. The penetration of the outer layers of bone allows blood and stem cells to form a clot in the area of the cartilage defect.

Articular cartilage. Articular cartilage is the highly specialized connective tissue of diarthrodial joints. Its principal function is to provide a smooth, lubricated surface for articulation and to facilitate the transmission of loads with a low frictional coefficient. Articular cartilage is devoid of blood vessels, lymphatics, and nerves and is subject to a harsh biomechanical environment. Most important, articular cartilage has a limited capacity for intrinsic healing and repair. In this regard, the preservation and health of articular cartilage are paramount to joint health.

The surfaces of articulating bones in mammalian joints are covered with articular cartilage. The articular cartilage prevents direct contact of the opposing bone surfaces and permits the near frictionless movement of the articulating bones relative to one another. Two types of articular cartilage defects are commonly observed in mammals and include full-thickness and partial-thickness defects. The two-types of defects differ not only in the extent of physical damage but also in the nature of repair response each type of lesion elicits.

Full-thickness articular cartilage defects include damage to the articular cartilage, the underlying subchondral bone tissue, and the calcified layer of cartilage located between the articular cartilage and the subchondral bone. Full-thickness defects typically arise during severe trauma of the joint or during the late stages of degenerative joint diseases, for example, during osteoarthritis. Since the subchondral bone tissue is both innervated and vascularized, damage to this tissue is often painful. The repair reaction induced by damage to the subchondral bone usually results in the formation of fibrocartilage at the site of the full-thickness defect. Fibrocartilage, however, lacks the biomechanical properties of articular cartilage and fails to persist in the joint on a long term basis.

Partial-thickness articular cartilage defects are restricted to the cartilage tissue itself. These defects usually include fissures or clefts in the articulating surface of the cartilage. Partial-thickness defects are caused by mechanical arrangements of the joint which in turn induce wearing of the cartilage tissue within the joint. In the absence of innervation and vasculature, partial-thickness defects do not elicit repair responses and therefore tend not to heal. Although painless, partial-thickness defects often degenerate into full-thickness defects.

Articular cartilage is hyaline cartilage and is 2 to 4 mm thick. It is composed of a dense extracellular matrix (ECM) with a sparse distribution of chondrocytes. The ECM is principally composed of water, collagen, and proteoglycans, with other noncollagenous proteins and glycoproteins present in lesser amounts. Along with collagen fiber ultrastructure and ECM, chondrocytes contribute to the various zones of articular cartilage—the superficial zone, the middle zone, the deep zone, and the calcified zone. Within each zone, 3 regions can be identified—the pericellular region, the territorial region, and the interterritorial region.

The thin superficial (tangential) zone protects deeper layers from shear stresses and makes up approximately 10% to 20% of articular cartilage thickness. The collagen fibers of this zone (primarily, type II and IX collagen) are packed tightly and aligned parallel to the articular surface. The superficial layer contains a relatively high number of flattened chondrocytes, and the integrity of this layer is imperative in the protection and maintenance of deeper layers. This zone is in contact with synovial fluid and is responsible for most of the tensile properties of cartilage, which enable it to resist the sheer, tensile, and compressive forces imposed by articulation.

Immediately deep to the superficial zone is the middle (transitional) zone, which provides an anatomic and functional bridge between the superficial and deep zones. The middle zone represents 40% to 60% of the total cartilage volume, and it contains proteoglycans and thicker collagen fibrils. In this layer, the collagen is organized obliquely, and the chondrocytes are spherical and at low density. Functionally, the middle zone is the first line of resistance to compressive forces.

The deep zone is responsible for providing the greatest resistance to compressive forces, given that collagen fibrils are arranged perpendicular to the articular surface. The deep zone contains the largest diameter collagen fibrils in a radial disposition, the highest proteoglycan content, and the lowest water concentration. The chondrocytes are typically arranged in columnar orientation, parallel to the collagen fibers and perpendicular to the joint line. The deep zone represents approximately 30% of articular cartilage volume.

The tide mark distinguishes the deep zone from the calcified cartilage. The deep zone is responsible for providing the greatest amount of resistance to compressive forces, given the high proteoglycan content. Of note, the collagen fibrils are arranged perpendicular to the articular cartilage. The calcified layer plays an integral role in securing the cartilage to bone, by anchoring the collagen fibrils of the deep zone to subchondral bone. In this zone, the cell population is scarce and chondrocytes are hypertrophic.

Collagen is the most abundant structural macromolecule in ECM, and it makes up about 60% of the dry weight of cartilage. Type II collagen represents 90% to 95% of the collagen in ECM and forms fibrils and fibers intertwined with proteoglycan aggregates. Collagen types I, IV, V, VI, IX, and XI are also present but contribute only a minor proportion. The minor collagens help to form and stabilize the type II collagen fibril network.

Proteoglycans account for 10% to 15% of the wet weight of cartilage. Articular cartilage contains a variety of proteoglycans that are essential for normal function, including aggrecan, decorin, biglycan, and fibromodulin. The largest in size and the most abundant by weight is aggrecan.

Chondrocytes are the resident cell type in articular cartilage. Chondrocytes are highly specialized, metabolically active cells that play a unique role in the development, maintenance, and repair of the ECM. Chondrocytes have limited potential for replication, a factor that contributes to the limited intrinsic healing capacity of cartilage in response to injury. Chondrocyte survival depends on an optimal chemical and mechanical environment. Biochemical markers of chondrocytes, include without limitation, collagen type II, chondroitin sulfate, keratin sulfate and characteristic morphologic markers of smooth muscle, including but not limited to the rounded morphology observed in culture, and able to secrete collagen type II, including but not limited to the generation of tissue or matrices with hemodynamic properties of cartilage in vitro.

Fibrocartilage. Fibrocartilage is formed by acute local injury at a bone site in the absence of biochemical factors to direct cartilage formation. The mechanical properties are inferior to articular cartilage. For example, indicia of fibrocartilage include proteoglycan-producing chondrocytes and fibrotic cells, which stain positive for collagen (COL) 1 and matrix metalloproteinase (MMP) 13 and negative for COL 2.

Microfracture is a surgical technique that produces "microfractures" in subchondral bone perpendicular to the surface. This technique may use various angled awls or "pics.", or small drills. A rough, raw surface that could hold the clot may also be formed. The pic was ideal for this, as it produced fracture fragments that attracted and held the clot. In order for tissue to regenerate, cells must be present. In this procedure, the controlled "microfractures" through the subchondral bone allow access to marrow-based progenitor cells and growth factors. A marrow clot is formed at the base of a prepared chondral lesion. The pluripotent cells proliferate and differentiate.

General indications for microfracture include full-thickness defects, unstable cartilage that overlies the subchondral bone, and a partial-thickness lesion that, when probed, the cartilage simply scrapes off down to bone. Patient age is not a specific contraindication. While patients under 35 years of age have greater improvement, older patients still show improvement. The size of the lesion is also not a contraindication for microfracture. Lesions may less than 400 mm$^2$ or more than 400 mm$^2$. The height of the cartilage rim surrounding the lesion may be adequate to hold the clot in place.

MRI can be used to assess the thickness of the cartilage and determine other associated injuries. The MRI enables imaging of morphological changes such as chondral fibrillation, fissuring, focal defects and corresponding fragments, and more diffuse thinning and wear, all manifesting as changes of the chondral thickness and surface at the cartilage interface to joint fluid and synovium. Earlier chondral degenerative changes, such as softening or blistering, to later fibrotic change can also be visible as intrasubstance areas of MRI signal change and heterogeneity, although such evaluation is still qualitative in standard clinical practice.

A thorough diagnostic arthroscopic examination of the joint can be performed through 3 portals (inflow cannula, arthroscope, and working instruments). Particular attention is paid to anterior interval scarring, plicae, and the lateral retinaculum, which have the potential to increase compression between cartilage surfaces. Microfracture is the final intra-articular procedure performed. This allows the initial clot in the microfracture site to be preserved. This can also prevent loss of visualization with blood and fat droplets entering the knee from the microfracture.

After identification of the full-thickness articular cartilage lesion, all remaining unstable cartilage is removed. A handheld curved curette and a full radius resector can be used to remove the loose or marginally attached cartilage back to a stable rim of cartilage. The calcified cartilage layer that remains as a cap to many lesions is removed, preferably by using a curette. Thorough and complete removal of the calcified cartilage layer is extremely important based on animal studies we have completed.[11] The integrity of the subchondral plate should be maintained. It is important that the defect is debrided deep enough to remove calcified cartilage layer but not so deep that the subchondral plate is damaged. This prepared lesion, with a stable perpendicular edge of healthy well-attached viable cartilage surrounding the defect provides a pool that helps hold the marrow clot as it forms.

Arthroscopic awls are used to make multiple holes, or "microfractures." An angled awl, typically 30° or 45°, permits the tip to be perpendicular to the bone as it is advanced. A 90° awl is used for the patella or other soft bone; however, it should only be advanced manually, not with a mallet. Starting at the periphery, microfracture holes are made, ending with holes toward the center of the defect. These are made far enough apart so they do not break into each other, and the subchondral plate between them is protected. Fat droplets from the marrow cavity are seen when the appropriate depth (approximately 2 to 4 mm) has been reached. When completed, the irrigation fluid pump pressure is reduced to observe the release of marrow fat droplets and blood from the microfracture holes. During microfracture, a rough surface has been created in the defect. This surface should not be debrided or shaved further to make it smooth. This rough surface allows for the marrow clot to adhere more easily, yet the integrity of the subchondral plate is maintained for joint surface shape.

As used herein, the term "BMP-2" refers to the family of bone morphogenetic proteins of the type 2, derived from any species, and may include mimetics and variants thereof. Reference to BMP-2 herein is understood to be a reference to any one of the currently identified forms, including BMP-2A and BMP-2B, as well as to BMP-2 species identified in the future. The term "BMP-2" also includes polypeptides derived from the sequence of any known BMP-2 whose mature sequence is at least about 75% homologous with the sequence of a mature human BMP-, which reference sequence may be found in Genbank, accession number NP_001191.

BMP-2 signals via two types of receptors (BRI and BRII) that are expressed at the cell surface as homomeric as well as heteromeric complexes. Prior to ligand binding, a low but measurable level of BMP-receptors is found in preformed hetero-oligomeric complexes. The major fraction of the receptors is recruited into hetero-oligomeric complexes only after ligand addition. For this, BMP-2 binds first to the high affinity receptor BRI and then recruits BRII into the signaling complex. However, ligand binding to the preformed complex composed of BRII and BRI is still required for signaling, suggesting that it may mediate activating conformational changes. Signals induced by binding of BMP-2 to preformed receptor complexes activate the Smad pathway, whereas BMP-2-induced recruitment of receptors activates a different, Smad-independent pathway resulting in the induction of alkaline phosphatase activity via p38 MAPK.

"BMP2 agents" include molecules that function similarly to BMP2 by binding and activating its receptors as described above. Molecules useful as BMP2 agents include derivatives, variants, and biologically active fragments of naturally occurring BMP2. A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active variant will have an amino acid sequence having at least about 90% amino acid sequence identity with a native sequence polypeptide, preferably at least about 95%, more preferably at least about 99%. The variant polypeptides can be naturally or non-naturally glycosylated, i.e., the polypeptide has a glycosylation pattern that differs from the glycosylation pattern found in the corresponding naturally occurring protein. The variant polypeptides can have post-translational modifications not found on the natural BMP2 protein.

Fragments and fusion proteins of soluble BMP2, particularly biologically active fragments and/or fragments corresponding to functional domains, are of interest. Fragments of interest will typically be at least about 10 aa to at least about 15 aa in length, usually at least about 50 aa in length, but will usually not exceed about 142 aa in length, where the fragment will have a stretch of amino acids that is identical to BMP2. A fragment "at least 20 aa in length," for example, is intended to include 20 or more contiguous amino acids from, for example, the polypeptide encoded by a cDNA for BMP2. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods.

In some embodiments, a dose of BMP2 is provided in an implant, e.g. a matrix or scaffold for localized delivery of the factor, where the BMP2 is provided as a BMP2 protein or active fragment thereof. The effective dose may be determined based on the specific tissue, rate of release from the implant, size of the implant, and the like, and may be empirically determined by one of skill in the art. The dose may provide for biological activity equivalent to 1 μg BMP2 protein, 10 μg, 100 μg, 1 mg, 5 mg, 10 mg, 25 mg, 50 mg, 75 mg, 100 mg, 250 mg, 500 mg, 750 mg, 1 g of BMP2 protein. The dose may be administered at a single time point, e.g. as a single implant; or may be fractionated, e.g. delivered in a microneedle configuration. The dose may be administered, once, two, three time, 4 times, 5 times, 10 times, or mare as required to achieve the desired effect, and administration may be daily, every 2 days, every 3 days, every 4 days, weekly, bi-weekly, monthly, or more.

VEGF is a dimeric, disulfide-linked 46-kDa glycoprotein related to Platelet-Derived Growth Factor ("PDGF"). It is produced by normal cell lines and tumor cell lines; is an endothelial cell-selective mitogen; shows angiogenic activity in in vivo test systems (e.g., rabbit cornea); is chemotactic for endothelial cells and monocytes; and induces plasminogen activators in endothelial cells, which are involved in the proteolytic degradation of the extracellular matrix during the formation of capillaries.

"VEGF inhibitor" as used herein is any substance that decreases signaling by the VEGF-VEGFR pathway. VEGF inhibitors can be, to name just a few examples, small molecules, peptides, polypeptides, proteins, including more specifically antibodies, including anti-VEGF antibodies, anti-VEGFR antibodies, intrabodies, maxibodies, minibodies, diabodies, Fc fusion proteins such as peptibodies, receptibodies, soluble VEGF receptor proteins and fragments, and a variety of others. Many VEGF inhibitors work by binding to VEGF or to a VEGF receptor. Others work more indirectly by binding to factors that bind to VEGF or to a VEGF receptor or to other components of the VEGF signaling pathway. Still other VEGF inhibitors act by altering regulatory posttranslational modifications that modulate VEGF pathway signaling. VEGF inhibitors in accordance with the invention also may act through more indirect mechanisms. Whatever the mechanism involved, as used herein, a VEGF inhibitor decreases the effective activity of the VEGF signaling pathway in a given circumstance over what it would be in the same circumstance in the absence of the inhibitor.

In some embodiments, a dose of VEGF inhibitor is provided in an implant, e.g. a matrix or scaffold for localized delivery of the facto. The effective dose may be determined based on the specific tissue, rate of release from the implant, size of the implant, and the like, and may be empirically determined by one of skill in the art. The dose may provide for biological activity equivalent to 1 µg soluble VEGF receptor, 10 µg, 100 µg, 1 mg, 5 mg, 10 mg, 25 mg, 50 mg, 75 mg, 100 mg, 250 mg, 500 mg, 750 mg, 1 g of soluble VEGF receptor. The dose may be administered at a single time point, e.g. as a single implant; or may be fractionated, e.g. delivered in a microneedle configuration. The dose may be administered, once, two, three time, 4 times, 5 times, 10 times, or mare as required to achieve the desired effect, and administration may be daily, every 2 days, every 3 days, every 4 days, weekly, bi-weekly, monthly, or more.

A great many VEGF inhibitors have been described in the literature. In addition to those described in further detail below, VEGF inhibitors are described in the following patent documents: US 2003/0105091, US2006/0241115, U.S. Pat. Nos. 5,521,184, 5,770,599, 5,990,141, 6,235,764, 6,258,812, 6,515,004, 6,630,500, 6,713,485, WO2005/070891, WO 01/32651, WO 02/68406, WO 02/66470, WO 02/55501, WO 04/05279, WO 04/07481, WO 04/07458, WO 04/09784, WO 02/59110, WO 99/450029, WO 00/59509, WO 99/61422, WO 00/12089, WO 00/02871, and WO 01/37820, particularly in parts pertinent to VEGF inhibitors.

The following are among specific VEGF inhibitors: ABT-869 (Abbott) including formulations for oral administration and closely related VEGF inhibitors; AEE-788 (Novartis) (also called AE-788 and NVP-AEE-788, among others) including formulations for oral administration and closely related VEGF inhibitors; AG-13736 (Pfizer) (also called AG-013736) including formulations for oral administration and closely related VEGF inhibitors; AG-028262 (Pfizer) and closely related VEGF inhibitors; Angiostatin (EntreMed) (also called CAS Registry Number 86090-08-6, K1-4, and rhuAngiostatin, among others) and closely related inhibitors as described in, among others, U.S. Pat. Nos. 5,792,825 and 6,025,688, particularly in parts pertaining to Angiostatin and closely related VEGF inhibitors, their structures and properties, and methods for making and using them; Avastin™ (Genentech) (also called bevacizumab, R-435, rhuMAB-VEGF, and CAS Registry Number 216974-75-3, among others) and closely related VEGF inhibitors; AVE-8062 (Ajinomoto Co. and Sanofi-aventis) (also called AC-7700 and combretastatin A4 analog, among others), and closely related VEGF inhibitors; AZD-2171 (AstraZeneca) and closely related VEGF inhibitors; Nexavar® (Bayer AG and Onyx) (also called CAS Registry Number 284461-73-0, BAY-43-9006, raf kinase inhibitor, sorafenib, sorafenib analogs, and IDDBCP150446, among others) and closely related VEGF inhibitors; BMS-387032 (Sunesis and Bristol-Myers Squibb) (also called SNS-032 and CAS Registry Number 345627-80-7, among others) and closely related VEGF inhibitors; CEP-7055 (Cephalon and Sanofi-aventis) (also called CEP-11981 and SSR-106462, among others) and closely related VEGF inhibitors; CHIR-258 (Chiron) (also called CAS Registry Number 405169-16-6, GFKI, and GFKI-258, among others) and closely related VEGF inhibitors; CP-547632 (OSI Pharmaceuticals and Pfizer) (also called CAS Registry Number 252003-65-9, among others) and closely related VEGF inhibitors such as, for instance, CP-564959; E-7080 (Eisai Co.) (also called CAS Registry Number 417716-92-8 and ER-203492-00, among others) and closely related VEGF inhibitors; 786034 (GlaxoSmithKline) and closely related VEGF inhibitors; GW-654652 (GlaxoSmithKline) and closely related indazolylpyrimidine Kdr inhibitors; IMC-1C11 (ImClone) (also called DC-101 and c-p1C11, among others) and closely related VEGF inhibitors; KRN-951 (Kirin Brewery Co.) and other closely related quinoline-urea VEGF inhibitors; PKC-412 (Novartis) (also called CAS Registry Number 120685-11-2, benzoylstaurosporine, CGP-41251, midostaurin, and STI-412, among others) and closely related VEGF inhibitors; PTK-787 (Novartis and Schering) (also called CAS Registry Numbers 212141-54-3 and 212142-18-2, PTK/ZK, PTK-787/ZK-222584, ZK-22584, VEGF-TKI, VEGF-RKI, PTK-787A, DE-00268, CGP-79787, CGP-79787D, vatalanib, ZK-222584, among others) and closely related anilinophthalazine derivative VEGF inhibitors; SU11248 (Sugen and Pfizer) (also called SU-11248, SU-011248, SU-11248J, Sutent®, and sunitinib malate, among others) and closely related VEGF inhibitors; SU-5416 (Sugen and Pfizer/Pharmacia) (also called CAS Registry Number 194413-58-6, semaxanib, 204005-46-9, among others) and closely related VEGF inhibitors; SU-6668 (Sugen and Taiho) (also called CAS Registry Number 252916-29-3, SU-006668, and TSU-68, among others) and closely related VEGF inhibitors as described in, among others, WO-09948868, WO-09961422, and WO-00038519, particularly in parts pertaining to SU-6668 and closely related VEGF inhibitors, their structures and properties, and methods for making and using them; VEGF Trap (Regeneron and Sanofi-aventis) (also called AVE-0005 and Systemic VEGF Trap, among others) and closely related VEGF inhibitors as described in, among others, WO-2004110490, particularly in parts pertaining to VEGF Trap and closely related VEGF inhibitors, their structures and properties, and methods for making and using them; Thalidomide (Celgene) (also called CAS Registry Number 50-35-1, Synovir, Thalidomide Pharmion, and Thalomid, among others) and closely related VEGF inhibitors; XL-647 (Exelixis) (also called EXEL-7647, among others) and closely related VEGF inhibitors; XL-999 (Exelixis) (also called EXEL-0999, among others) and closely related VEGF inhibitors; XL-880 (Exelixis) (also called EXEL-2880, among others) and closely related VEGF inhibitors; ZD-6474 (AstraZeneca) (also called CAS Registry Number 443913-73-3, Zactima, and AZD-6474, among others) and closely related anilinoquinazoline VEGF inhibitors; and ZK-304709 (Schering) (also called CDK inhibitors (indirubin derivatives), ZK-CDK, MTGI, and multi-target tumor growth inhibitor, among others) and other closely related compounds including the indirubin derivative VEGF inhibitors described in WO-00234717, WO-02074742, WO-02100401, WO-00244148, WO-02096888, WO-03029223, WO-02092079, and WO-02094814, particularly in parts pertinent to these and closely related VEGF inhibitors, their structures and properties, and methods for making and using them.

VEGF inhibitors may be delivered in a manner appropriate to the nature of the inhibitor, e.g. as a protein, small molecule, nucleic acid, etc., including without limitation appropriate vehicles and vectors as required.

Drug delivery devices include structures that can be implanted and that release the active agents, e.g. BM P2 and VEGF inhibitor, at the targeted site. Implantable drug delivery devices can be broadly classified in two main groups: passive implants and active implants. The first group includes two main types of implants: biodegradable and non-biodegradable implants. Active systems rely on energy dependent methods that provide the driving force to control drug release. The second group includes devices such as osmotic pressure gradients and electromechanical drives.

Passive Polymeric Implants are normally relatively simple devices with no moving parts, they rely on passive diffusion for drug release. They are generally made of drugs packed within a biocompatible polymer molecule. Several parameters such as: drug type/concentration, polymer type, implant design and surface properties can be modified to control the release profile. Passive implants can be classified in two main categories: non-biodegradable and biodegradable systems.

Non-biodegradable implants are commonly prepared using polymers such as silicones, poly(urethanes), poly(acrylates) or copolymers such as poly(ethylene vinyl acetate). Poly(ethylene-vinyl acetate) (PEVA) is a thermoplastic copolymer of ethylene and vinyl acetate. Poly(siloxanes) or silicones are organosilicon polymeric materials composed of silicon and oxygen atoms. Lateral groups can be methyl, vinyl or phenyl groups. These groups will influence the properties of the polymer. Poly(siloxanes) have been extensively used in medicine due to the unique combination of thermal stability, biocompatibility, chemical inertness and elastomeric properties. The silicones commonly used for medical devices are vulcanised at room temperature. They are prepared using a two-component poly(dimethylsiloxanes) (PDMS) in the presence of a catalyst (platinum based compound). The final material is formed via an addition hydrosilation reaction. An alternative method to obtain silicones for medical applications is the using linear PDMS with hydroxyl terminal groups. This linear polymer is cross-linked with low molecular weight tetra(alkyloxysilane) using stannous octoate catalyst.

This type of device can be monolithic or reservoir type implant. Monolithic type implants are made from a polymer matrix in which the drug is homogeneously dispersed. On the other hand, reservoir-type implants contain a compact drug core covered by a permeable non-biodegradable membrane. The membrane thickness and the permeability of the drug through the membrane will govern the release kinetics.

Biodegradable implants are made using polymers or block copolymers that can be broken down into smaller fragments that will be subsequently excreted or absorbed by the body. Normally they are made using polymers such as collagen, PEG, chitin, poly(caprolactone) (PCL), poly(lactic acid) (PLA) or poly(lactic-co-glycolic acid) (PLGA). Numerous other biodegradable polymers for drug delivery exist including: poly(amides), poly(anhydrides), poly(phosphazenes) and poly(dioxanone). Poly(anhydrides) have a low hydrolytic stability resulting in rapid degradation rates, making them suitable for use in short-term controlled delivery systems. Poly(phosphazenes) have a degradation rate that can be finely tuned by appropriate substitution with specific chemical groups and use of these polymers has been investigated for skeletal tissue regeneration and drug delivery. Poly(dioxanone), like PCL, is a polylactone that has been used for purposes such as drug delivery, and tissue engineering They do not need to be extracted after implantation, as they will be degraded by the body of the patient. They can be manufactured as monolithic implants and reservoir-type implants. In addition to the biopolymers, such as the above-mentioned PLA, there a few natural polymers which also represent a promising class of materials with a wide range of applications, including use in implantable devices. These natural polymers include, collagen, hyaluronic acid, cellulose, chitosan, silk and others naturally derived proteins, as well as collagen, gelatin, albumin, elastin and milk proteins. These materials present certain advantages compared to the traditional materials (metals and ceramics) or synthetic polymers, such as biocompatibility, biodegradation and non-cytotoxicity, which make them ideal to be used in implantable drug delivery devices.

Dynamic or Active Polymeric Implants have a positive driving force to control the release of drugs from the device. The majority of the implants in this category are electronic systems made of metallic materials. Dynamic drug delivery implants are mainly pump type implants. The main type of polymeric active implants are osmotic pumps. This type of device is formed mainly by a semipermeable membrane that surrounds a drug reservoir. The membrane should have an orifice that will allow drug release. Osmotic gradients will allow a steady inflow of fluid within the implant. This process will lead to an increase in the pressure within the implant that will force drug release trough the orifice. This design allows constant drug release (zero order kinetics). This type of device allows a favorable release rate but the drug loading is limited.

In some embodiments, the factors are prepared as an injectable paste. The paste can be injected into the implant site. In some embodiments, the paste can be prepared prior to implantation and/or store the paste in the syringe at sub-ambient temperatures until needed. In some embodiments, application of the composite by injection can resemble a bone cement that can be used to join and hold bone fragments in place or to improve adhesion of, for example, a hip prosthesis, for replacement of damaged cartilage in joints, and the like. Implantation in a non-open surgical setting can also be performed.

In other embodiments the factors are prepared as formable putty. The hydrated graft putty can be prepared and molded to approximate any implant shape. The putty can then be pressed into place to fill a void in the cartilage, bone, tooth socket or other site. In some embodiments, graft putty can be used to repair defects in non-union bone or in other situations where the fracture, hole or void to be filled is large and requires a degree of mechanical integrity in the implant material to both fill the gap and retain its shape.

A system for pharmaceutical use, i.e. a drug delivery device with factors, can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the NR pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical composition, i.e. combinations of factors and/or cells, can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxin, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

By "proliferate" it is meant to divide by mitosis, i.e. undergo mitosis. An "expanded population" is a population of cells that has proliferated, i.e. undergone mitosis, such that the expanded population has an increase in cell number, that is, a greater number of cells, than the population at the outset.

The term "tissue" refers to a group or layer of similarly specialized cells which together perform certain special functions.

The term "organ" refers to two or more adjacent layers of tissue, which layers of tissue maintain some form of cell-cell and/or cell-matrix interaction to form a microarchitecture.

The terms "individual," "subject," "host," and "patient," are used interchangeably herein and refer to any mammalian subject for whom diagnosis, treatment, or therapy is desired, particularly humans.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

"Co-administer" means to administer in conjunction with one another, together, coordinately, including simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning. The methods of the invention also include the use of factor combinations that consist, or consist essentially of the desired factors, for example an implant may consist of a matrix and protein factors consisting of BMP2 and a VEGF inhibitor.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

The term "skeletal stem cell" refers to a multipotent and self-renewing cell capable of generating bone marrow stromal cells, skeletal cells, and chondrogenic cells. By self-renewing, it is meant that when they undergo mitosis, they produce at least one daughter cell that is a skeletal stem cell. By multipotent it is meant that it is capable of giving rise to progenitor cell (skeletal progenitors) that give rise to all cell types of the skeletal system. They are not pluripotent, that is, they are not capable of giving rise to cells of other organs in vivo.

Skeletal stem cells can be reprogrammed from non-skeletal cells, including without limitation mesenchymal stem cells, and adipose tissue containing such cells, such as human adipose stem cells (hAASC). Induced skeletal cells have characteristics of functional SSCs derived from nature, that is, they can give rise to the same lineages.

Human SSC cell populations may be characterized by their cell surface markers, although it will be understood by one of skill in the art that endogenous populations of SSC need not be characterized for effective stimulation. Human SSC are negative for expression of CD45, CD235, Tie2, and CD31; and positively express podoplanin (PDPN). A population of cells, e.g. cells isolated from bone tissue, having this combination of markers may be referred to as [PDPN$^+$/146$^-$] cells. The [PDPN$^+$/146$^-$] population can be further subdivided into three populations: a unipotent subset capable of chondrogenesis [PDPN$^+$CD146$^-$CD73$^-$CD164$^-$], a unipotent cellular subpopulation capable of osteogenesis [PDPN$^+$CD146$^-$CD73$^-$CD164$^-$] and a multipotent [PDPN$^+$CD146$^-$CD73$^+$CD164$^-$] cell capable of endochondral (bone and cartilage) ossification. A population of cells of interest for use in the methods of the invention may be isolated from bone with respect to CD45, CD235, Tie2, and CD31 and PDPN. Other cell populations of interest are [PDPN$^+$CD146$^-$CD73$^-$CD164$^-$] cells; [PDPN$^+$CD146$^-$CD73$^-$CD164$^-$] cells; and [PDPN$^+$CD146$^-$CD73$^+$CD164$^-$] cells.

The mouse skeletal lineage is characterized as CD45–, Ter119–, Tie2–, αv integrin+. The SSC is further characterized as Thy1– 6C3– CD105– CD200+.

Adipose-Derived Stem Cells. Adipose-derived stem cells or "adipose-derived stromal cells" refer to cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may be provided as a primary cell culture or an immortalized cell line. The adipose tissue may be from any organism having fat tissue. Preferably, the adipose tissue is mammalian, most preferably the adipose tissue is human. A convenient source of adipose tissue is from liposuction surgery, however, the source of adipose tissue or the method of isolation of adipose tissue is not critical to the invention.

Adipose tissue is abundant and accessible to harvest methods with minimal risk to the patient. It is estimated that there are more than 10$^4$ stem cells per gram of adipose tissue (Sen et al 2001, Journal of Cellular Biochemistry 81:312-319), which cells can be used immediately or cryopreserved for future autologous or allogeneic applications.

Methods for the isolation, expansion, and differentiation of human adipose tissue-derived cells have been reported. See for example, Burris et al 1999, Mol Endocrinol 13:410-7; Erickson et al 2002, Biochem Biophys Res Commun. Jan. 18, 2002; 290(2):763-9; Gronthos et al 2001, Journal of Cellular Physiology, 189:54-63; Halvorsen et al 2001, Metabolism 50:407-413; Halvorsen et al 2001, Tissue Eng. 7(6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517. Adipose tissue-derived stromal cells may be obtained from minced human adipose tissue by collagenase digestion and differential centrifugation [Halvorsen et al 2001, Metabolism 50:407-413; Hauner et al 1989, J Clin Invest 84:1663-1670; Rodbell et al 1966, J Biol Chem 241:130-139].

Adipose tissue derived stem cells have been reported to express markers including: CD13, CD29, CD44, CD63, CD73, CD90, CD166, aldehyde dehydrogenase (ALDH), and ABCG2. The adipose tissue derived stem cells may be a population of purified mononuclear cells extracted from adipose tissue capable of proliferating in culture for more than 1 month.

For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The cell population may be used immediately. Alternatively, the cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The adipose cells may be cultured in vitro under various culture conditions. Culture medium may be liquid or semisolid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin. In one embodiment of the invention, the adipose cells are maintained in culture in the absence of feeder layer cells, i.e. in the absence of serum, etc. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

The terms "efficiency of reprogramming", "reprogramming efficiency", "efficiency of conversion", or "conversion efficiency" are used interchangeably herein to refer to the ability of cells of one cell lineage to give rise to an induced cell of another cell lineage when contacted with the appropriate reprogramming system, for example, the ability of adipose tissue cells to give rise to iSSC when contacted with high doses of BMP2. In other words, the cells produce about 1.5-fold, about 2-fold, about 3-fold, about 4-fold, about 6-fold, about 8-fold, about 10-fold, about 20-fold, about 30-fold, about 50-fold, about 100-fold, about 200-fold the number of induced cells (e.g. iSSC) as the uncontacted population, or more.

Mammalian species that may be treated with the present methods include canines and felines; equines; bovines; ovines; etc. and primates, particularly humans. Animal models, particularly small mammals, e.g. murine, lagomorpha, etc. may be used for experimental investigations.

More particularly, the present invention finds use in the treatment of subjects, such as human patients, in need of bone or cartilage replacement therapy. Examples of such subjects would be subjects suffering from conditions associated with the loss of cartilage from osteoarthritis, genetic defects, disease, etc. Patients having diseases and disorders characterized by such conditions will benefit greatly by a treatment protocol of the pending claimed invention.

An effective amount of a pharmaceutical composition of the invention is the amount that will result in an increase the cartilage regeneration at the site of implant. For example, an effective amount of a pharmaceutical composition will increase cartilage mass by at least about 5%, at least about 10%, at least about 20%, preferably from about 20% to about 50%, and even more preferably, by greater than 50% (e.g., from about 50% to about 100%) as compared to the appropriate control, the control typically being a subject not treated with the composition.

The methods of the present invention also find use in combined therapies, e.g. in with therapies that are already known in the art to provide relief from symptoms associated with the aforementioned diseases, disorders and conditions. The combined use of a pharmaceutical composition of the present invention and these other agents may have the advantages that the required dosages for the individual drugs is lower, and the effect of the different drugs complementary.

In some embodiments an effective dose of adipose stromal cells, preferably adipose derived stem cells, are optionally provided in an implant or scaffold for the regeneration of cartilaginous tissue. An effective cell dose may depend on the purity of the population. In some embodiments an effective dose delivers a dose of adipose derived stem cells of at least about $10^2$, about $10^3$, about $10^4$, about $10^5$, about $10^6$, about $10^7$, about $10^8$, about $10^9$ or more cells, which stem cells may be present in the cell population at a concentration of about 1%, about 5%, about 10%, about 20%, about 30%, about 40%, about 50%, about 60%, about 70%, about 80%, about 90% or more.

Conditions for Treatment

Osteoarthritis (OA) affects nearly 27 million people in the United States, accounting for 25% of visits to primary care physicians, and half of all NSAID prescriptions. OA is a chronic arthropathy characterized by disruption and potential loss of joint cartilage along with other joint changes, including bone remodeling that may include bone hypertrophy (osteophyte formation), subchondral sclerosis, and formation of subchondral cysts. OA is viewed as failure of the synovial joint. OA results in the degradation of joints, including articular cartilage and subchondral bone, resulting in mechanical abnormalities and impaired joint function. Symptoms may include joint pain, tenderness, stiffness, sometimes an effusion, and impaired joint function. A variety of causes can initiate processes leading to loss of cartilage.

OA may begin with joint damage from trauma to the joint; mechanical injury to the meniscus, articular cartilage, a joint ligament, or another joint structure; defects in cartilage matrix components; and the like. Mechanical stress on joints may underlie the development of OA in many individuals, with many and varied sources of mechanical stress, including misalignments of bones caused by congenital or pathogenic causes; mechanical injury; overweight; loss of strength in muscles supporting joints; and impairment of peripheral nerves, leading to sudden or dyscoordinated movements that overstress joints.

In synovial joints there are at least two movable bony surfaces that surrounded by the synovial membrane, which secretes synovial fluid, a transparent alkaline viscid fluid which fills the joint cavity, and articular cartilage, which is interposed between the articulating bony surfaces. The earliest gross pathologic finding in osteoarthritis is softening of the articular cartilage in habitually loaded areas of the joint surface. This softening or swelling of the articular cartilage is frequently accompanied by loss of proteoglycans from the cartilage matrix. With progression of osteoarthritis the integrity of the cartilage surface is lost and the articular cartilage thins, with vertical clefts extending into the depth of the cartilage in a process called fibrillation. Joint motion may cause fibrillated cartilage to shed segments that expose the bone underneath (subchondral bone). The subchondral bone is remodeled in OA, including the development of subchondral sclerosis, development of subchondral cysts, and the formation of ectopic bone termed osteophytes. Subchondral cysts also develop which may be filled with synovial fluid. At the joint margins osteophytes (bone spurs) form. The remodeling of subchondral bone increases the mechanical strain and stresses on both the overlying articular cartilage and subchondral bone, leading to further damage of both the cartilage and subchondral bone.

The tissue damage stimulates chondrocytes to attempt repair, which increases production of proteoglycans and collagen. However, efforts at repair also stimulate the enzymes that degrade cartilage, as well as inflammatory cytokines, which are normally present in small amounts. Inflammatory mediators trigger an inflammatory cycle that further stimulates the chondrocytes and synovial lining cells, eventually breaking down the cartilage. Chondrocytes undergo programmed cell death (apoptosis).

OA should be suspected in patients with gradual onset of symptoms and signs, particularly in older adults, usually beginning with one or a few joints. Pain can be the earliest symptom, sometimes described as a deep ache. Pain is usually worsened by weight bearing and relieved by rest but can eventually become constant. Stiffness follows awakening or inactivity. If OA is suspected, plain x-rays should be taken of the most symptomatic joints. X-rays generally reveal marginal osteophytes, narrowing of the joint space, increased density of the subchondral bone, subchondral cyst formation, bony remodeling, and joint effusions. Standing x-rays of knees are more sensitive in detecting joint space narrowing. Magnetic resonance imaging (MRI) can be used to detect cartilage degeneration, and several MRI-based based scoring systems have been developed to characterize the severity of OA.

OA commonly affects the hands, feet, spine, and the large weight bearing joints, such as the hips and knees, although in theory, any joint in the body can be affected. As OA progresses, the affected joints appear larger, are stiff and painful, and usually feel better with gentle use but worse with excessive or prolonged use. Treatment generally involves a combination of exercise, lifestyle modification, and analgesics. If pain becomes debilitating, joint replacement surgery may be used to improve the quality of life.

Among the agents that have demonstrated partial efficacy in control of pain associated with OA are analgesics such as acetaminophen and anti-inflammatories including non-steroidal anti-inflammatory agents (NSAIDs), opiates, intraarticular corticosteroids, and hyaluronic acid derivatives injected into the joint. These agents have not been demonstrated to prevent cartilage loss or slow the loss of joint function.

Methods of Treatment

The present invention provides methods of treating a cartilage lesion, or injury, in a human or other animal subject, comprising applying to the site a composition factors of the invention, which may be provided in combinations with cements, gels, etc. As referred to herein such lesions include any condition involving cartilaginous tissue which is inadequate for physiological or cosmetic purposes. Such defects include those that are congenital, the result from disease or trauma, and consequent to surgical or other medical procedures. Such defects include for example, defect brought about during the course of surgery, osteoarthritis, osteoporosis, infection, malignancy, developmental malformation, etc.

An individual in need of cartilage regeneration can be treated with the methods described herein. An individual for treatment may have osteoarthritis. Various sites for articular cartilage regeneration can be treated, including without limitation knee joint, elbow joint, joints in the phalanges and phalanxes, shoulder joints, hip joints, wrist joints, ankle joints, etc. The individual may be an adult, e.g. past adolescence, and may be an aged adult, e.g. a human over 55 years of age, over 65 years of age, over 70 years of age, etc.

Methods of treatment first comprise an acute local injury. Typically the acute local injury is surgically performed through a microfracture process as described herein, and may be performed with awl, drill, etc.

In some embodiments an individual that presents with an acute local injury, e.g. from accidents, sports injuries, etc., may be beneficially treated with the provision of growth factors in order to reduce development of fibrocartilage and to enhance regeneration of articular cartilage.

At the time of microfracture, or shortly after local acute injury, a drug delivery device is implanted or otherwise positioned to provide an effective dose of BMP2 and a VEGF inhibitor. The factors may be provided individually or as a single composition, that is, as a premixed composition of factors. The factors may be provided at the same molar ratio or at different molar ratios. The factors may be provided once or multiple times in the course of treatment. For example, an implant comprising factors may be provided to an individual, and additional factors and/or cells provided during the course of treatment.

While in many cases the endogenous SSC are sufficient for regeneration, optionally exogenous cells are provided at the site of local acute injury. The cells may be SSC, or non-SSC, e.g. adipose stem cells. The cells may be autologous or allogeneic. The cells may be provided concomitant with the provision of growth factors, e.g. simultaneously, shortly before, shortly, after, etc. and may be in a single implant with the growth factors, as a separate implant or injection, etc.

The features and advantages of the present invention will be more clearly understood by reference to the following examples, which are not to be construed as limiting the invention.

EXPERIMENTAL

Example 1

Osteoarthritis (OA) is a degenerative disease resulting in irreversible, progressive destruction of hyaline cartilage lining articular joints 1. The etiology of OA is complex and involves a variety of factors, including genetic predisposition, acute injury, and chronic inflammation. Here we investigate the ability of resident skeletal stem cell (SSC) populations to regenerate cartilage in relation to age, a possible contributor to the development of osteoarthritis. We demonstrate that with greater maturity, the frequency of SSC in joints progressively decreased in both mice and humans corresponding to diminished chondrogenesis in mature adult tissue. However, a local expansion of SSC could still be triggered in the chondral surface of adult limb joints by stimulating a regenerative response following microfracture (MF) surgery. While MF-activated SSC tend to form fibrous tissues, we found that localized co-delivery of BMP2 and soluble VEGFR1 (sVEGFR1), a VEGF receptor antagonist, in a biochemical hydrogel can drive the differentiation of MF-activated SSC towards generation of articular cartilage. These data demonstrate that following MF, there is a therapeutic window to skew MF-activated SSC differentiation fate towards robust formation of de novo cartilage for treating localized chondral disease in OA. Our findings provide a new stem cell paradigm for regenerating cartilage that is validated in both mouse and human tissues. To our knowledge this is the first time that stable articular cartilage has been successfully regenerated in vivo by activation and fate control of autologous tissue-resident SSC populations.

Maturity leads to a reduction in articular clonality and mSSC. To test the hypothesis that alterations in SSC activity underlie age-related susceptibility to OA, we first assessed changes in clonal skeletogenesis in the articular surfaces of distal femurs of different aged Rainbow reporter mice in situ. We crossed Rainbow reporter mice with a transgenic mouse which ubiquitously-expressed β Actin-Cre$^{ERT}$ to include the possibility that genetic drivers (other than Lepr1) may be active in SSC populations within articular cartilage. To induce random colorimetric labeling of cells systemically in β Actin-Cre$^{ERT}$/Rainbow mice, we injected tamoxifen into newborn (P3), juvenile (2 week), adult (6 week), and aged (1 year) mice, then isolated limb tissue one month after treatment to measure the frequency of uniquely-colored clones in chondral tissues by histological analysis. The presence of Rainbow labeled areas is consistent with the presence of mSSC which has the ability to form multipotent colonies of cartilage and osteoblast lineage cells. We observed that skeletal maturity corresponds to a substantial reduction in the clonality of chondral tissues (FIGS. 1a-d). In addition, there was also a striking reduction in proteoglycan secretion with age in clonally marked chondral areas as detected by staining with Movat's Pentachrome and by H&E (FIG. 1f and FIG. 6).

Figures 1G, 1H:
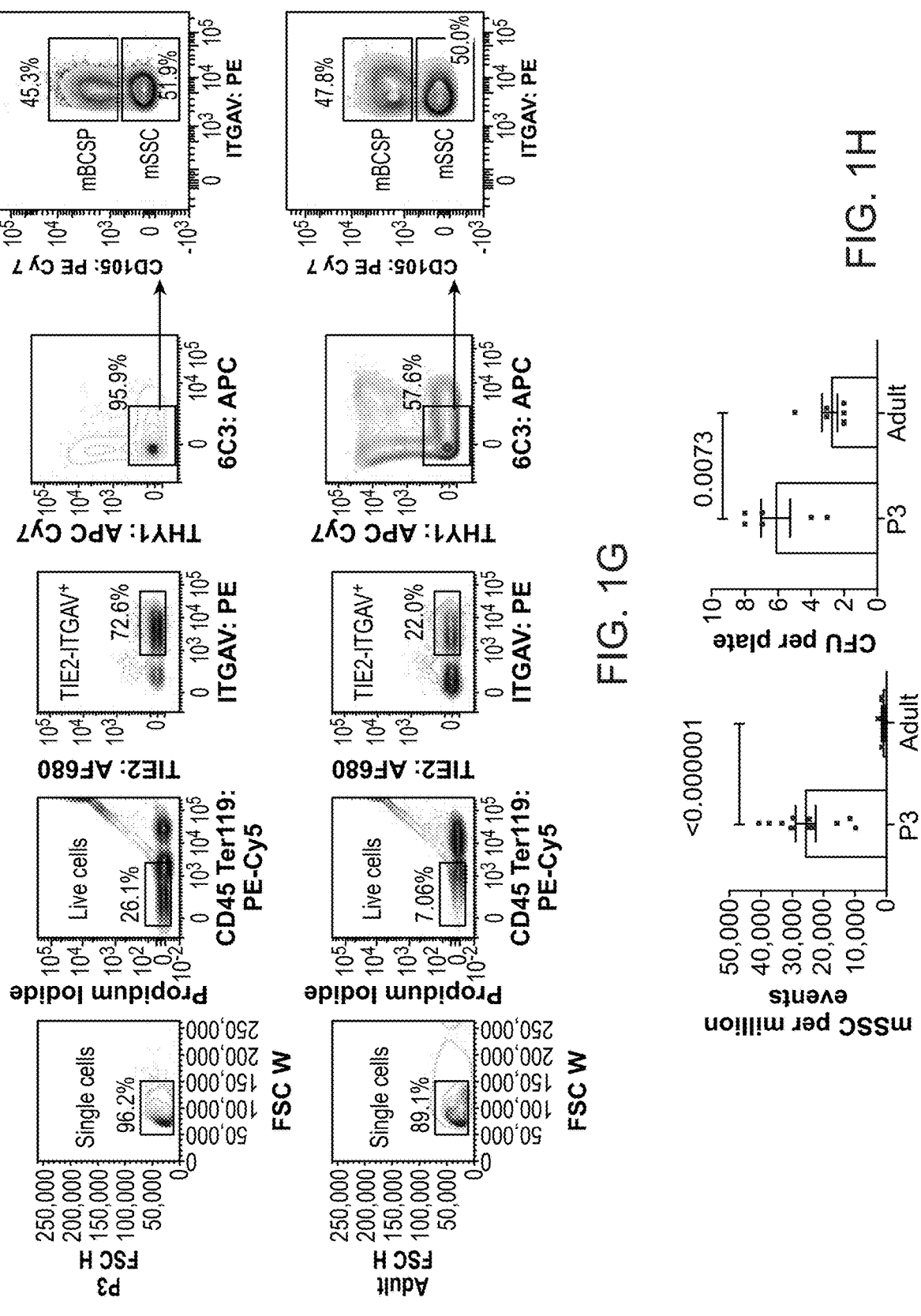

Since we had previously observed that clonal areas in mouse skeletal tissues are highly enriched for skeletal stem cells (SSCs) (FIG. 1e), we micro-dissected chondral regions from limb joints of young (P3) and adult C57/BL6 male mice to analyze their constituting cell populations by FACS. The chondral cells were isolated by mechanical and chemical dissociation of the distal femoral tissues then stained for SSC and mature skeletal lineage populations for FACS analysis using a previously published protocol. These analyses revealed that SSC and downstream bone cartilage and stromal progenitors (BCSP) were significantly diminished (95.9% vs. 57.6%) between P3 and adult mice (FIGS. 1g,h). Following FACS, we evaluated the SSCs for their clonogenic potential in vitro. Consistent with our observations of reduced clonality in mature chondral tissues of Rainbow mice, we also found that SSC isolated from adult mice have a reduced capacity to form colonies in vitro compared to chondral SSC isolated from P3 mice (FIG. 1h).

Figures 2A, 2B:
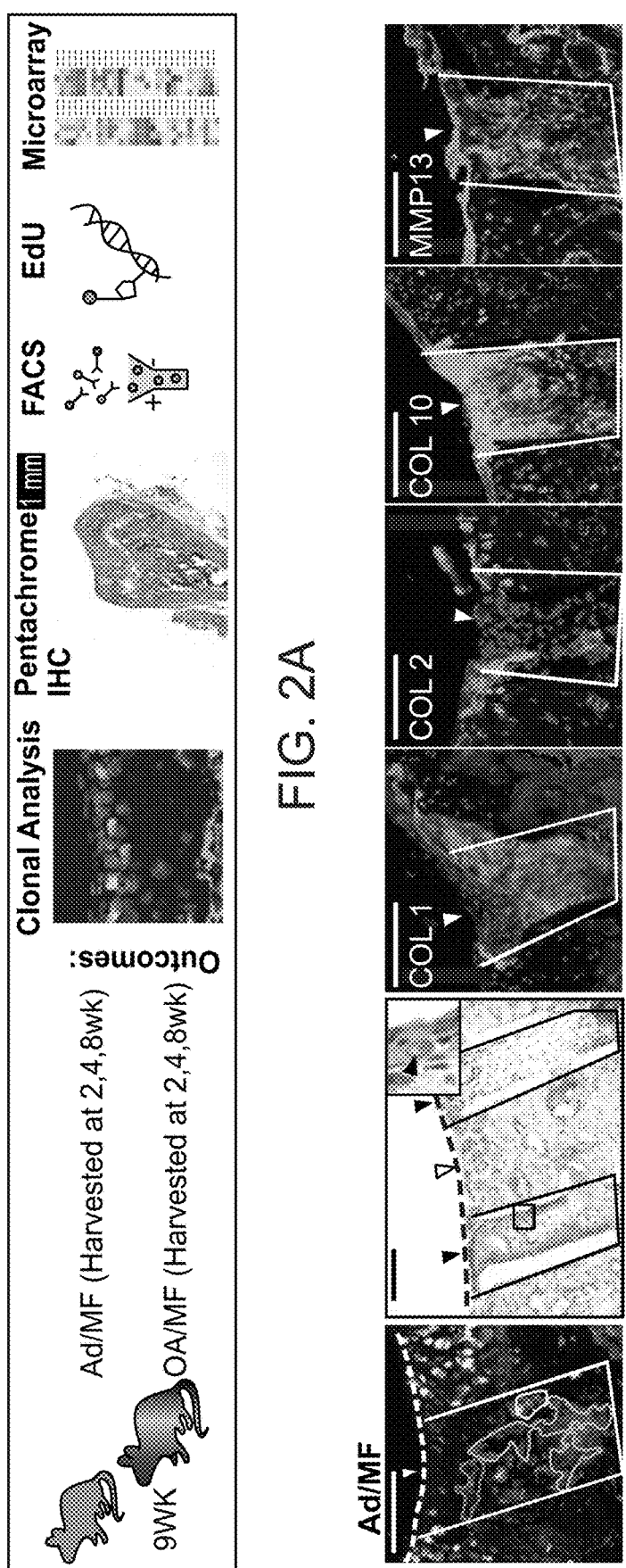
FIG. 2. Focal microfracture (MF) leads to a local amplification of mSSC at the articular surface. a, Schematic showing the experimental outline. b, (Panels left-right) Areas of Adult MF surgery showing clonal expansion within the defect (Panel 1: Actin-CreER), fibrocartilage formation within the defect (Panel 2: Pentachrome with higher magnification of chondrocytes marked by the black arrow in top right corner), confirmation of fibrocartilage by immunohistochemistry (Panels 3-6 showing presence of collagen (COL) 1 and matrix metallopeptidase (MMP) 13 and absence of COL 2). The presence of Col10 stain also suggests the existence of hypertrophic chondrocytes in the regenerate. This has been reported in osteoarthritic fibrocartilage in the knee (PMID: 25680653). Defect is outlined in solid lines with solid arrows demarcating the surface of the regenerate. Outlined arrow demarcates uninjured tissue. Dotted line denotes the articular surface. Scale bars 100 µm. c, Graph showing a transient increase in mSSC and mouse bone cartilage and stromal progenitors (mBCSP) after MF surgery (MF) over 4 weeks. Ordinary one-way ANOVA test (p=<0.0001) with post-hoc analysis using Šidák method to compare between specific means. N=10 per timepoint. d, Left panel: Pentachrome of fibrocartilage formation. Higher magnification of chondrocytes marked by black arrows in the top right corner. Solid arrows demarcate the surface of the regenerate. Outlined arrow demarcates uninjured tissue. Right panel: adjacent section with an increase in EdU+GFP cells within the regenerate outlined in solid lines and marked with solid arrows and white outline arrow shows the absence of proliferating cells in uninjured articular cartilage. Dotted line represents articular cartilage surface. Scale bars 100 µm. e, Graph showing an increase in EdU+mSSC and mBCSP 1-week post MF surgery (isolated by intracellular FACS). N=3. f, Schematic showing the parabiosis model with MF performed on non-GFP mice. g, Left panel shows GFP+ cells within the circulation of non-GFP parabiont confirming chimerism. Right panel shows an increase in mSSC and mBCSP but no GFP+ cells in either populations. h, (Left-right) OA/MF showing an increase in clones within the regenerate (Panel 1) and the presence of fibrocartilage within the regenerate on pentachrome formation with higher magnification of chondrocytes marked by white arrow (Panel 2). Immunofluorescence with COL 1, COL 2, COL 10, and MMP 13 demonstrates fibrocartilage (Panels 3-6). Dotted line denotes the articular surface. Solid arrows demarcate the surface of the regenerate. Scale bars 100 µm. i, Graph showing a nonsignificant increase in mSSC after OA with a significant increase in mSSC with OA/MF. Ordinary one-way ANOVA test (p=0.012) with post-hoc analysis using Šidák method to compare between specific means. N=10. j, Graph showing an insignificant decrease in proliferation of chronically injured mSSC contrasting with a significant increase in mSSC after OA/MF. Ordinary one-way ANOVA test (p=0.028) with post-hoc analysis using Šidák method to compare between specific means. N=3. k, (Left-right) PCA plot showing clustering of adult microarray data of adult (Ad) mice distinct from OA/MF and P3 microarray data. Pearson product-moment correlation coefficient of gene expression activity. N=3. Graphs unless otherwise stated show Mean+/−SEM. Student T-test. Exact P values to 2 significant figures shown.

Microfracture leads to an amplification of mSSC at the articular surface. The reduction in SSC that we observed with age led us to question how adult (Ad) SSCs respond to injury, including localized defects introduced by MF surgery. We had previously reported that mSSC and mBCSP are significantly amplified following bicortical fracture in adult mouse femurs. To assess how focal MF affected the resident SSC population at the articular surface, we introduced MF lesions with a dental drill on the distal femur articular surface of induced β Actin-Cre$^{ERT}$/Rainbow mice. We then followed MF-induced remodeling of the chondral tissue with a variety of techniques including morphometric analysis, immunostaining (IF), EdU labelling and FACS analysis (FIGS. 2a-e). Following MF surgery in adult mice (Ad/MF), we detected an increase in EdU-labeled proliferating cells in the vicinity of the MF site that corresponded to an increase in clonally derived tissues in the regenerate (FIGS. 2b,d). Compared to uninjured tissue, the regenerated tissues appeared to be morphologically heterogenous and contained proteoglycan-producing chondrocytes and fibrotic cells, which stained positive for collagen (COL) 1 and matrix metalloproteinase (MMP) 13 and negative for COL 2 (FIG. 2b). This MF-induced tissue was indicative of fibrocartilage, a form of scar cartilage. We also detected some Col10 stain that suggests the existence of hypertrophic chondrocytes in the regenerate. This has been reported in osteoarthritic fibrocartilage in the knee.

Figures 2C, 2D, 2F:
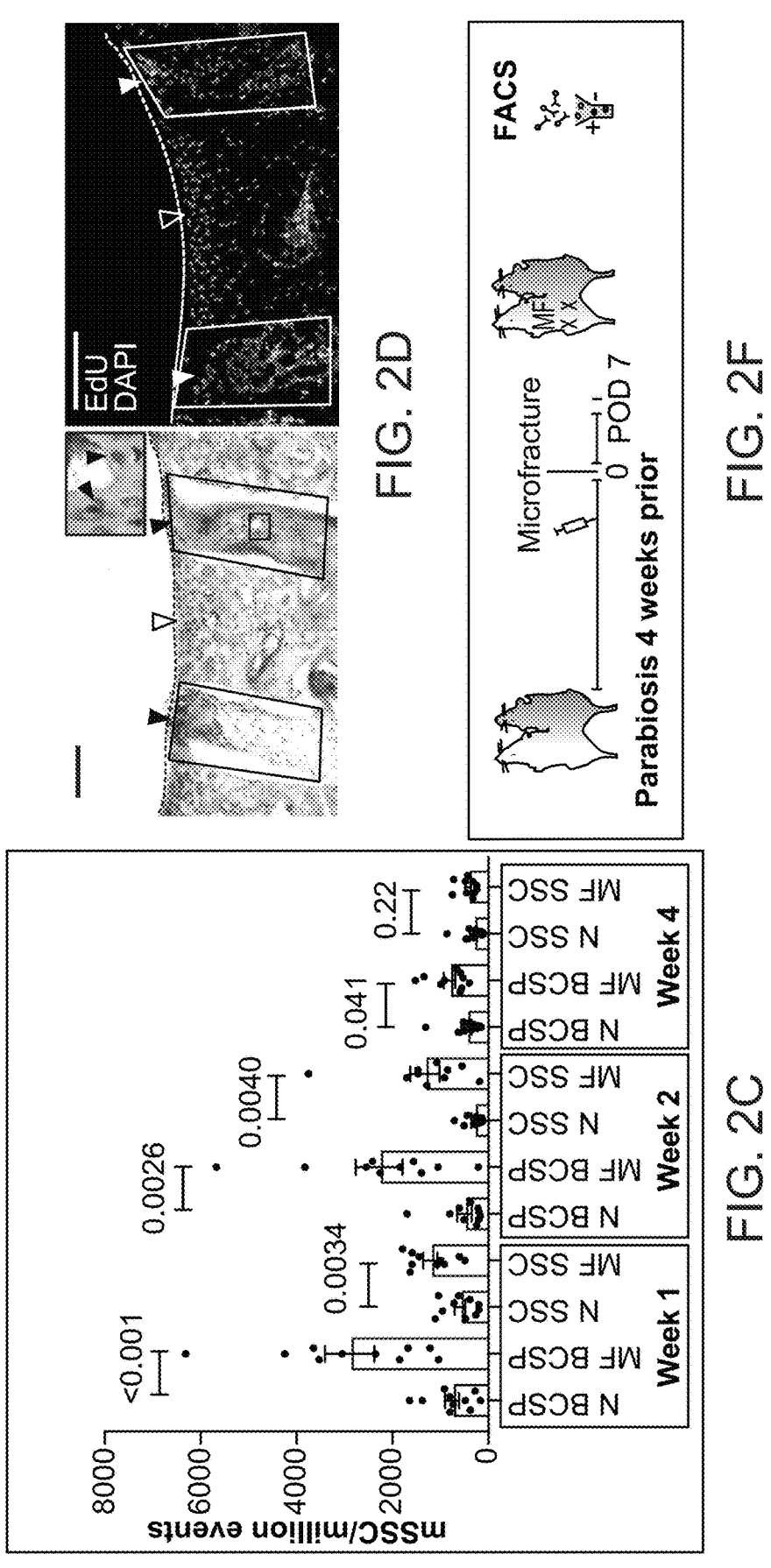

The local clonal expansion within the MF regenerate was suggestive of increased mSSC activity, confirmed by FACS analysis, which showed that following MF, there was a transient, but significant increase in mSSC and mBCSP populations at weeks 1 and 2 post-MF surgery. These mSSCs and mBCSP may be derived from populations that normally reside in the cartilage, bone marrow, and periosteum of the chondral tissues and the regenerate may also reflect differences in the relative contributions by each population. However, by week 4, the frequency of remaining mSSC was reduced (FIG. 2c). The MF-stimulated increase in SSC and BCSP populations appeared to be due to an expansion of skeletal stem/progenitors since the majority of expanded mSSC and mBCSP incorporated EdU as determined by intracellular FACS 1-week post MF (FIG. 2e).

We then asked whether the amplification of SSC numbers at the MF site could be due to recruitment of systemically-derived cells. To investigate potential contribution by circulating mSSC to the regenerate, we established heterochronic parabiont mice (FIG. 2f) by surgically fusing adult male GFP+ mice with non-GFP mice of the same C57/BL6 background. 4 weeks following parabiosis, we confirmed successful establishment of shared systemic circulation and detected a ratio of 50:50 GFP to non-GFP chimerism in the peripheral blood cells of conjoined parabionts (FIG. 2g). We then performed MF surgery on the distal femur of the non-GFP parabiont paired mouse. The non-GFP parabiont MF site had a significant increase in mSSC and mBCSP, however, none of the mSSC or mBCSP were derived from GFP+ circulating cells (FIG. 2g). We concluded that the increase in mSSC following MF is due to local expansion rather than recruitment of circulating mSSC at the injured mouse joint.

Microfracture leads to a local amplification of mSSC in a mouse OA model. While we have shown that MF can amplify regenerative mSSC in healthy adult mice, we hypothesized that MF could also stimulate mSSC expansion in osteoarthritic (OA) mouse joints. To evaluate the effects of MF in an OA setting, we employed a clinically-relevant mouse model of OA that is induced by destabilization of the medial meniscus. Following MF surgery in the OA joint (OA/MF), we observed a local increase in clonality within the defect, which resulted in fibrocartilage formation. Fibrocartilage was confirmed by immunofluorescence with the regenerating staining positive for COL 1 and MMP 13 and negative for COL 2 (FIG. 2h). Interestingly, chronic injury in OA without MF did not yield a significant increase in mSSC, however, MF surgery significantly increased the number of mSSC in OA (FIG. 2i). The MF-activated mSSC also demonstrated inherently greater proliferative potential as revealed by higher levels of EdU labeling in vitro, relative to mSSC isolated from adult mouse, and adult mouse OA joints (FIG. 2j).

Figure 6A:
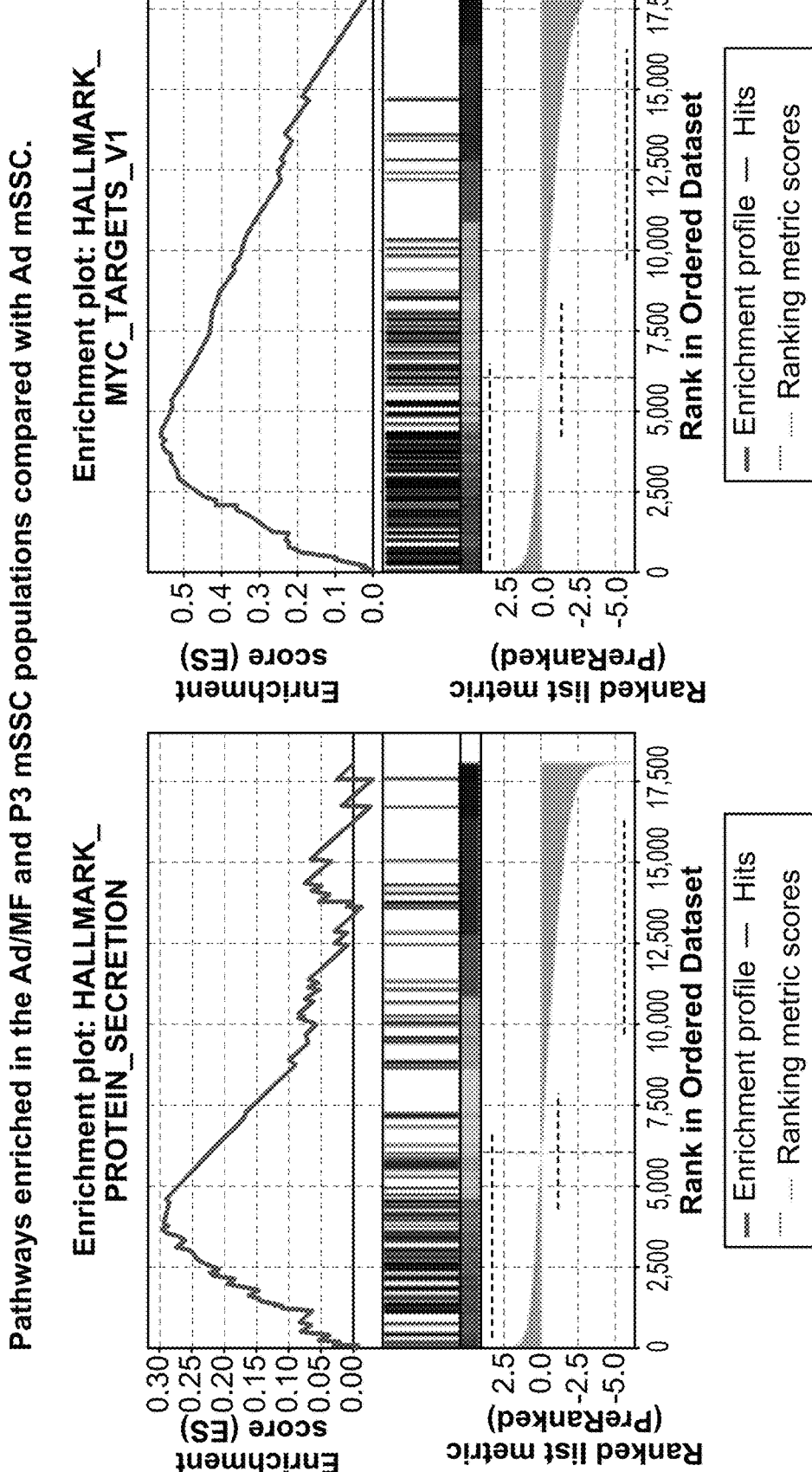
FIG. 6. Mouse microarray data analysis. a, Pathways significantly enriched in Ad/MF and P3 mSSC populations. Top row (Left-right): Protein secretion, MYC targets, E2F targets. Lower row (Left-right): G2M checkpoint, oxidative phosphorylation and TGFb signaling. b-c, 3 panels showing mSSC expression (b) and bulk tissue expression (c) of key genes involved in cartilage development, cell cycle and inflammation. d, Panel showing the direct effect of BMP2 and sVEGFR1 on in vitro mSSC gene expression.
Figures 6B, 6C:
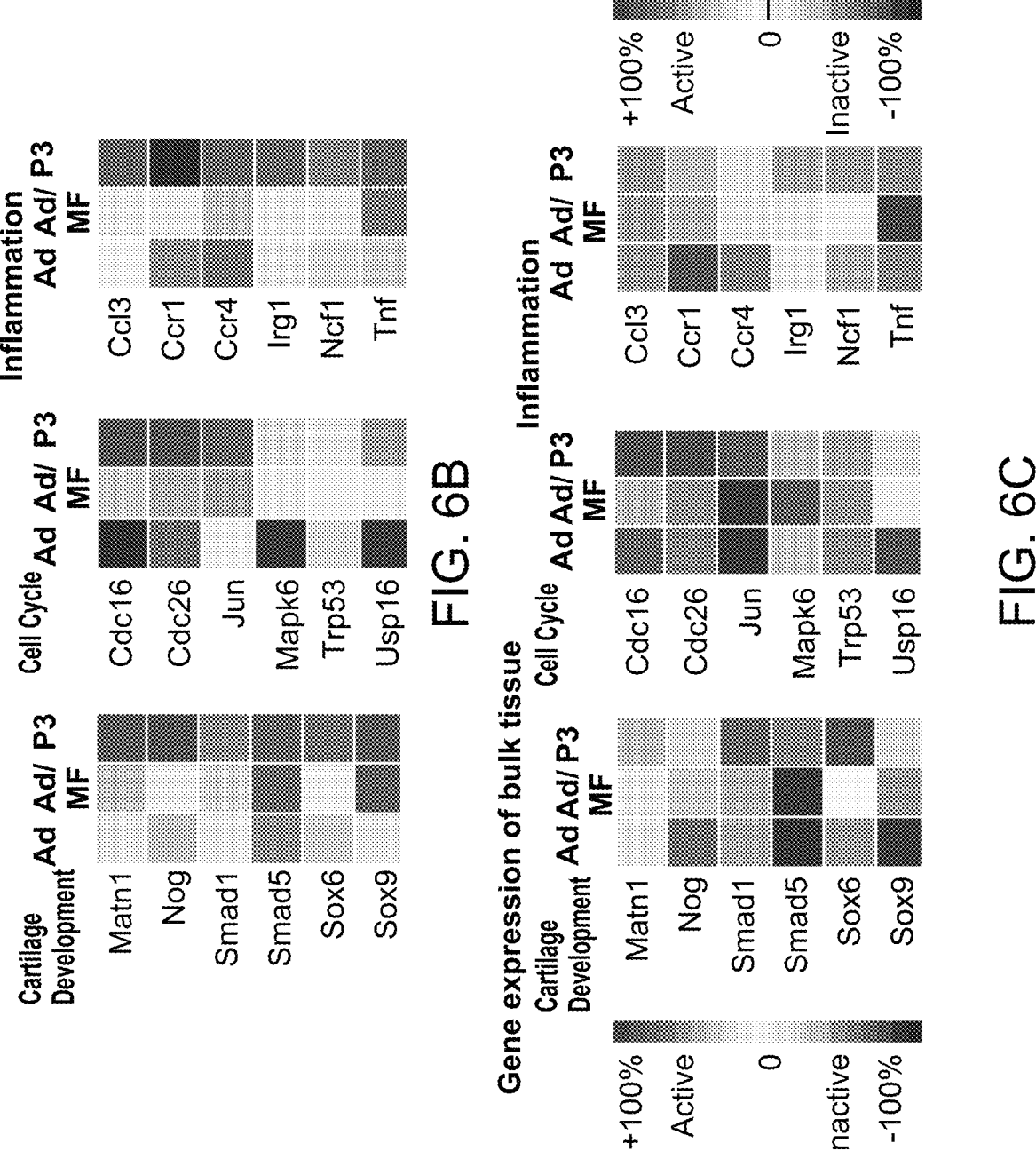

Microfracture reverts mSSC to a more juvenile expression profile. Since we had observed that fractures could induce re-expression of embryonic genes in the mandible that are silenced in adults, we asked whether MF induces similar changes in mSSC gene expression. We therefore isolated mSSC from adult mouse joints, adult mouse joints after MF (Ad/MF) and joints from newborn mice postnatal day 3 (P3) pups and compared their transcriptomes using microarray analysis. Using the Gene Expression Commons platform, we normalized the expression data and computed dynamic ranges across all probe sets and then performed Principle Component Analysis on the Adult, Ad/MF, and P3 mSSC transcriptomes. We found that the transcriptomes of adult uninjured mSSC (Ad) clustered separately from Ad/MF and P3 (FIG. 2k and FIG. 6ac). In particular Ad/MF mSSC showed greater overall transcriptomic similarity to P3 mSSC. Pathways enriched in Ad/MF and P3 mSSC also included those responsible for cell cycling and cartilage development (FIG. 6a-c), suggesting that MF reverts mSSC to a more juvenile gene expression (FIG. 6a-d).

Figure 3:
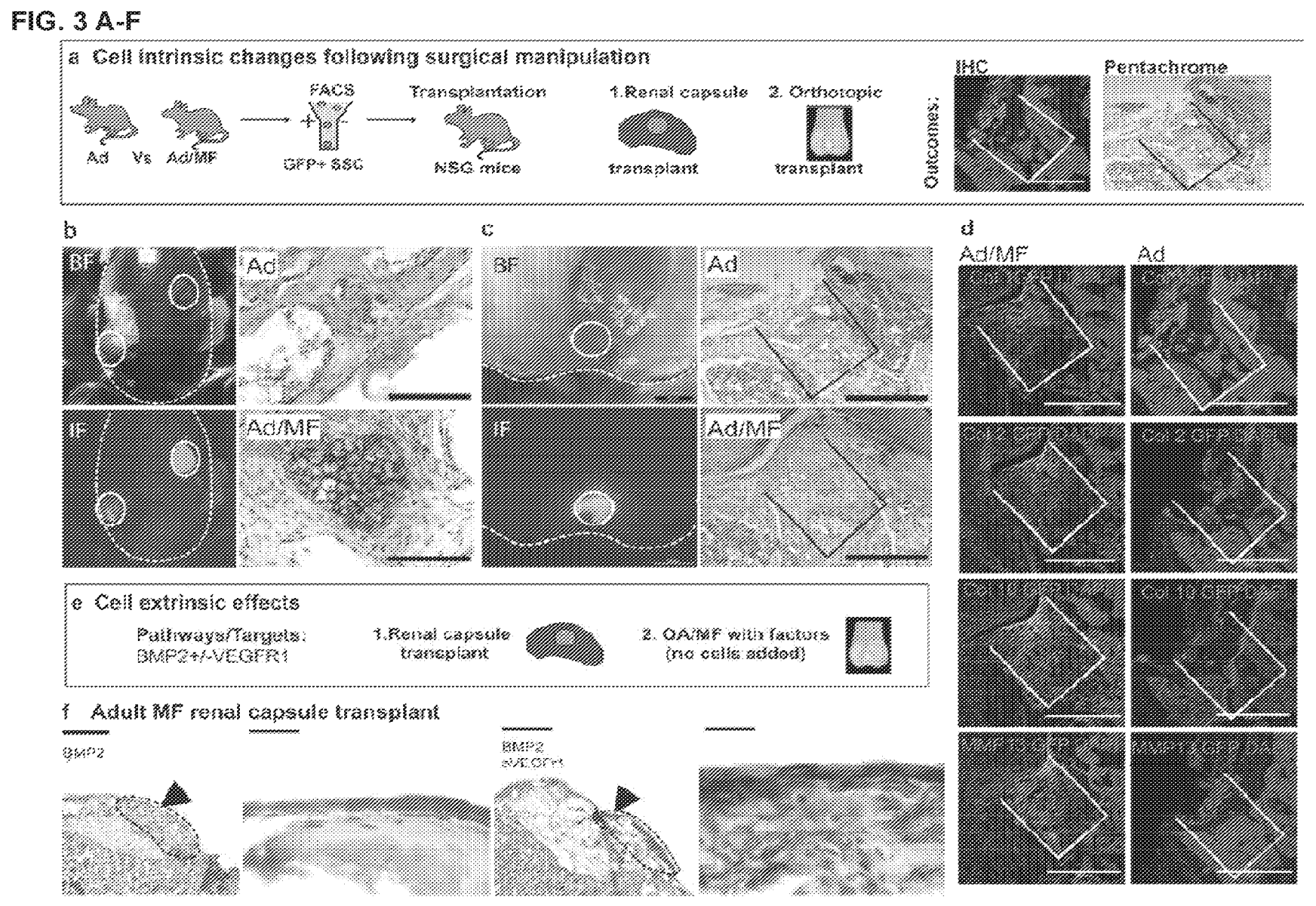
Figure 7A:
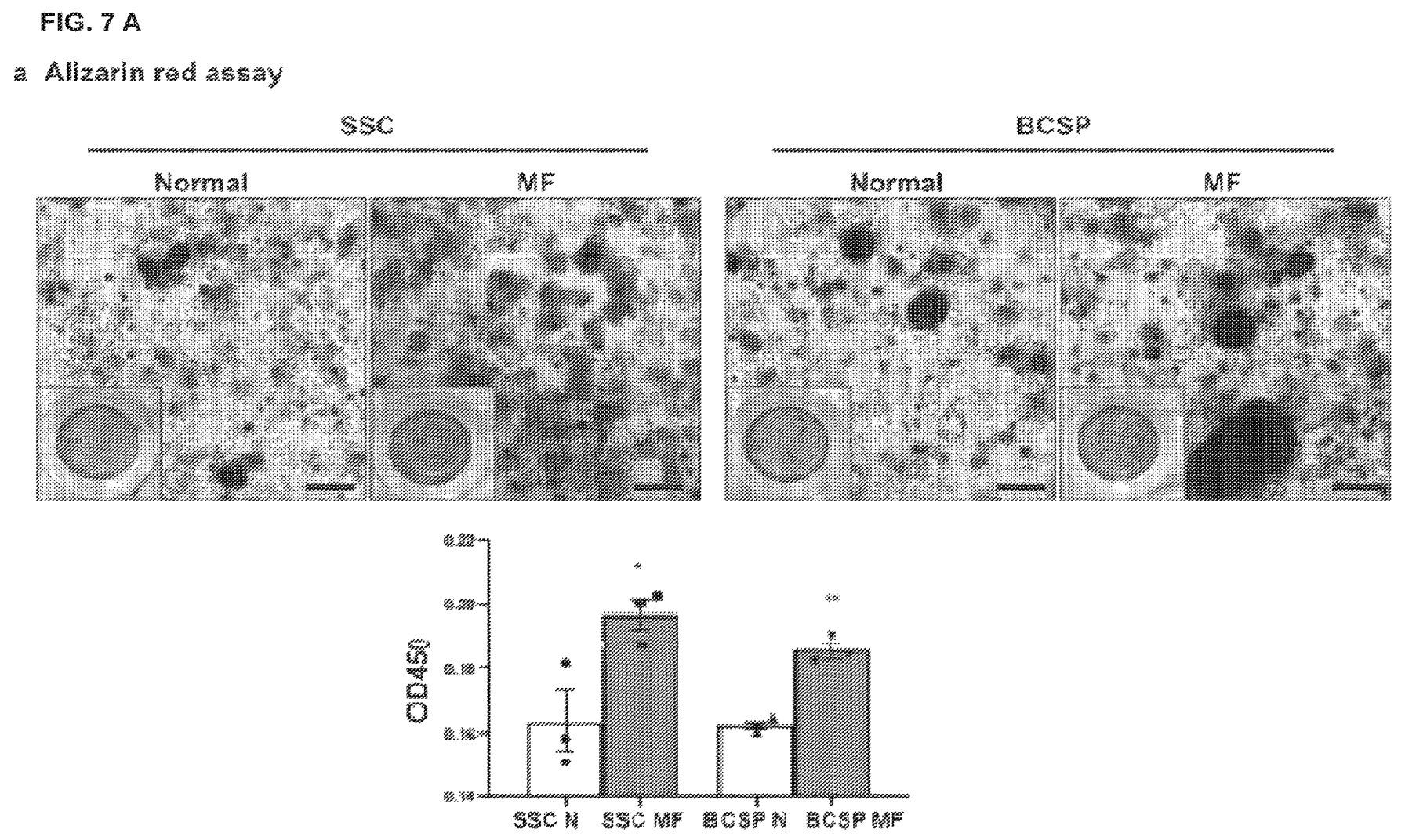
Figure 7B:
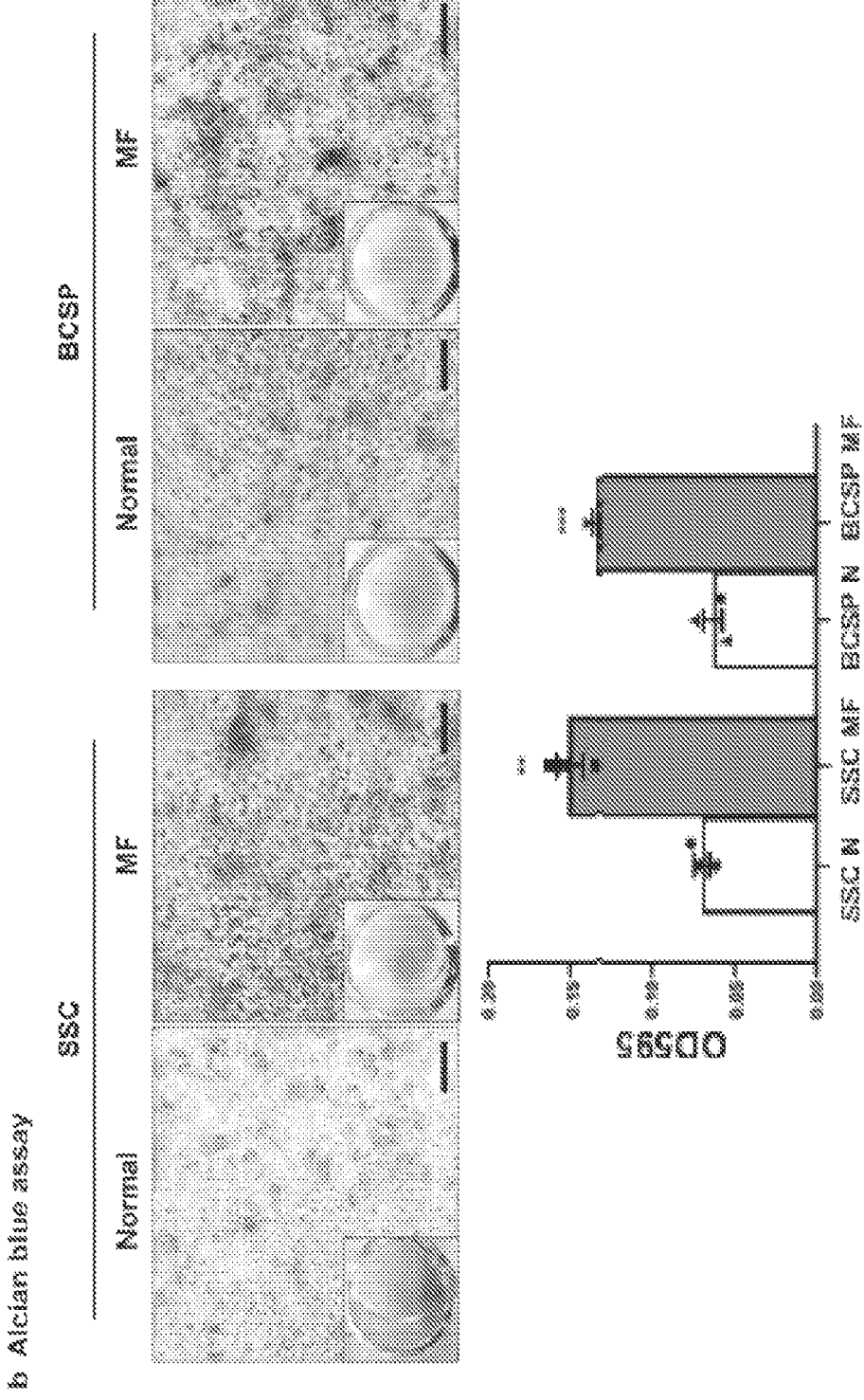
FIG. 7. In vitro assays for groups (Ad, Ad/MF). a, Alizarin red staining of Ad and Ad/MF mSSCs (Left) and mBCSPs (Right), and graph representing amount of alizarin stain detected (Bottom). b, Alcian blue staining of Ad and Ad/MF mSSCs (Left) and mBCSPs (Right), and graph representing amount of alcian blue stain detected (Bottom). c, Oil red 0 staining of Ad and Ad/MF mSSCs (Left) and mBCSPs (Right). Scale bar 100 μm.
Figure 7C:
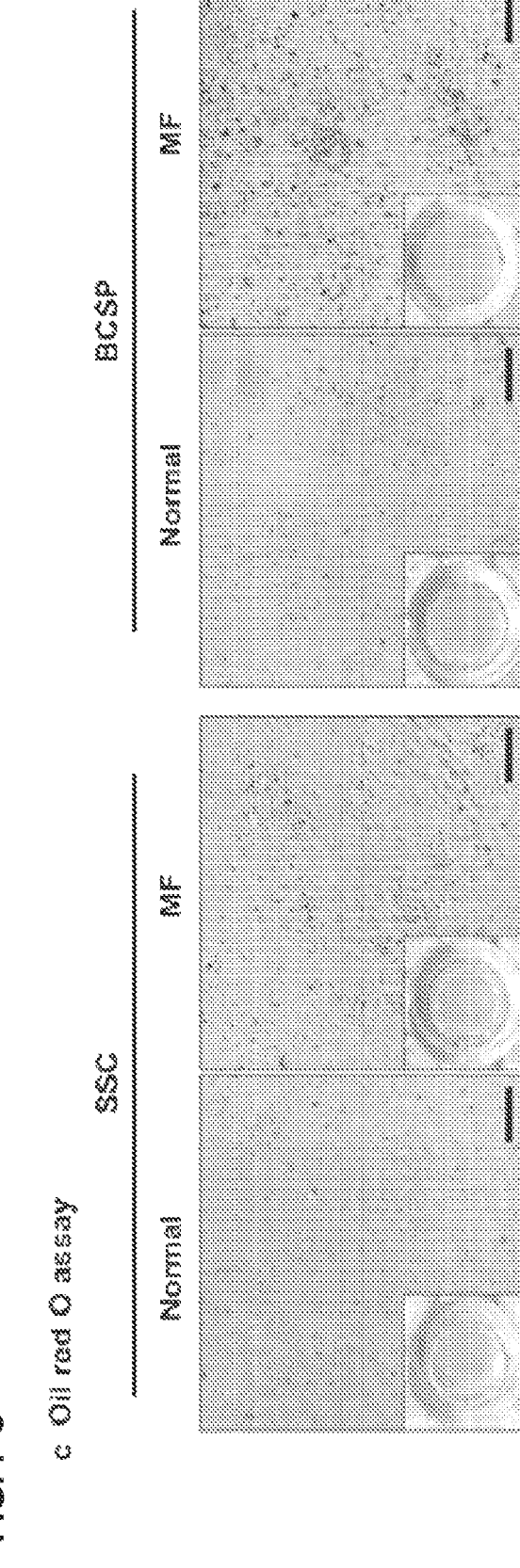
Figure 8B:
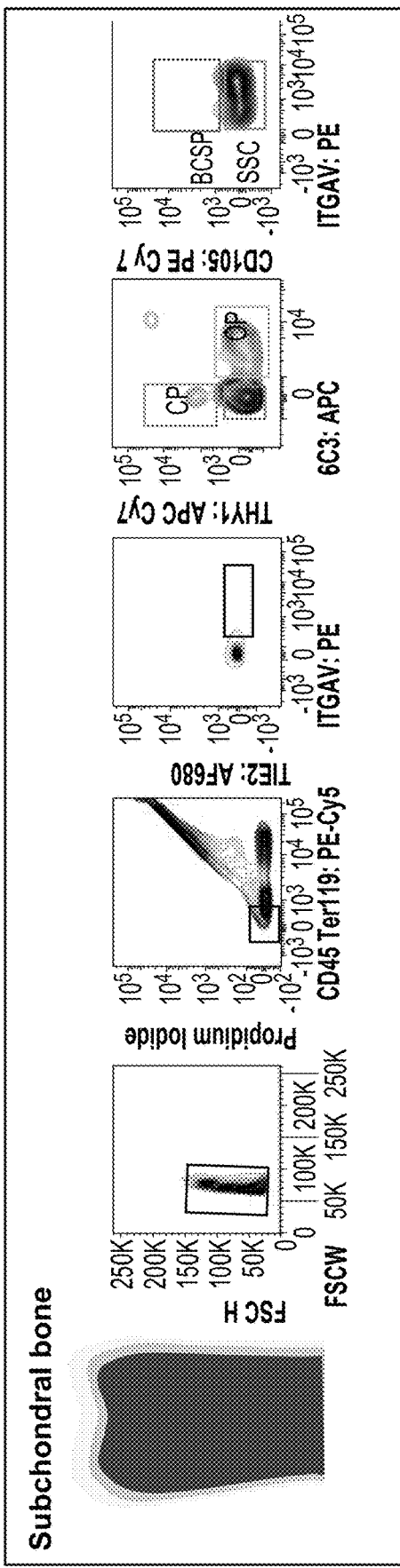
FIG. 8. Microdissection before and after MF surgery. a, Schematic depicting the distal femur of a mouse and its major tissue layers before and after MF surgery. b, FACS plots of the articular surface (Upper row), the periosteum (Middle row), and bone (Lower row) with relative populations of mOP, mCP, mBCSP, and mSSC. c, Graph of mSSC/million events in bone, cartilage, and periosteum. d, Graph of mSSC/million events comparing MF joints and joints with articular cartilage and periosteum removed prior to MF surgery (mMF). Graphs unless otherwise stated show Mean+/−SEM. Exact P values to 2 significant figures.
Figure 8D:
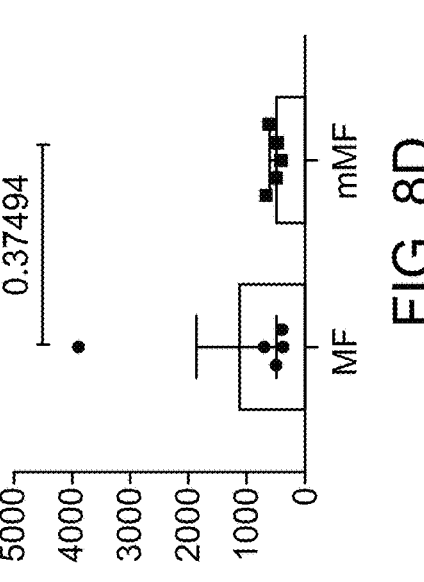
Figure 8C:
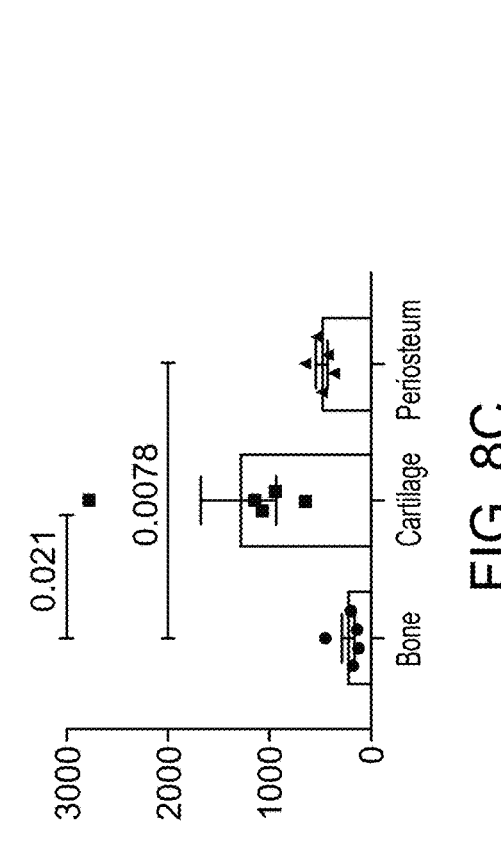

Microfracture reverts mSSC to a more juvenile phenotype. We previously observed that mBCSP isolated from fracture calluses display enhanced skeletogenic activity relative to mBCSP isolated from uninjured bone. To determine whether MF surgery alters mSSC on the articular surface, we transplanted GFP+mSSC collected from the distal femur including cartilage and bone (Ad) vs. adult MF (Ad/MF) into immunodeficient NSG mice in two different niches (FIG. 3a). Specifically, we transplanted 20,000 FACS isolated GFP+Ad or Ad/MF mSSC beneath the renal capsule or orthotopically into the distal femur following MF. Four weeks post-transplantation, we observed that Ad/MF mSSC formed both fibrous and cartilaginous tissue in both niches (FIG. 3b,c lower right panels). In contrast, Ad mSSC formed more bone tissue regardless of recipient site (kidney or knee) (FIG. 3b,c upper right panels). We also observed higher contribution by GFP-labeled Ad/MF mSSC in the regenerated tissue than Ad mSSC after transplantation to the knee (FIG. 3d), consistent with previous EdU assays indicating greater proliferative capacity by Ad/MF mSSC than Ad mSSC (FIG. 2d,e). GFP+Ad/MF mSSC also formed more fibrocartilage compared to Ad mSSC as seen by IF co-stain showing COL1 and MMP 13 positivity within the GFP+Ad/MF mSSC cellular matrix (FIG. 3d). Both in terms of their enhanced proliferation and increased cartilage formation, our data suggest that MF-activated SSC more closely resemble juvenile than adult uninjured mSSC. Consistent with the in vivo data, mSSC from MF also shows intrinsically enhanced osteogenic and cartilagenic potential in vitro with absent adipogenic potential (FIG. 7a-c). By carefully microdissecting out the articular surface, periosteum, and bone marrow after MF surgery for FACS analysis, we find that the mobilization of activated mSSC likely involves all three areas, although there were higher frequencies of activated mSSCs in the chondral areas (FIG. 4a-d).

Figure 6D:
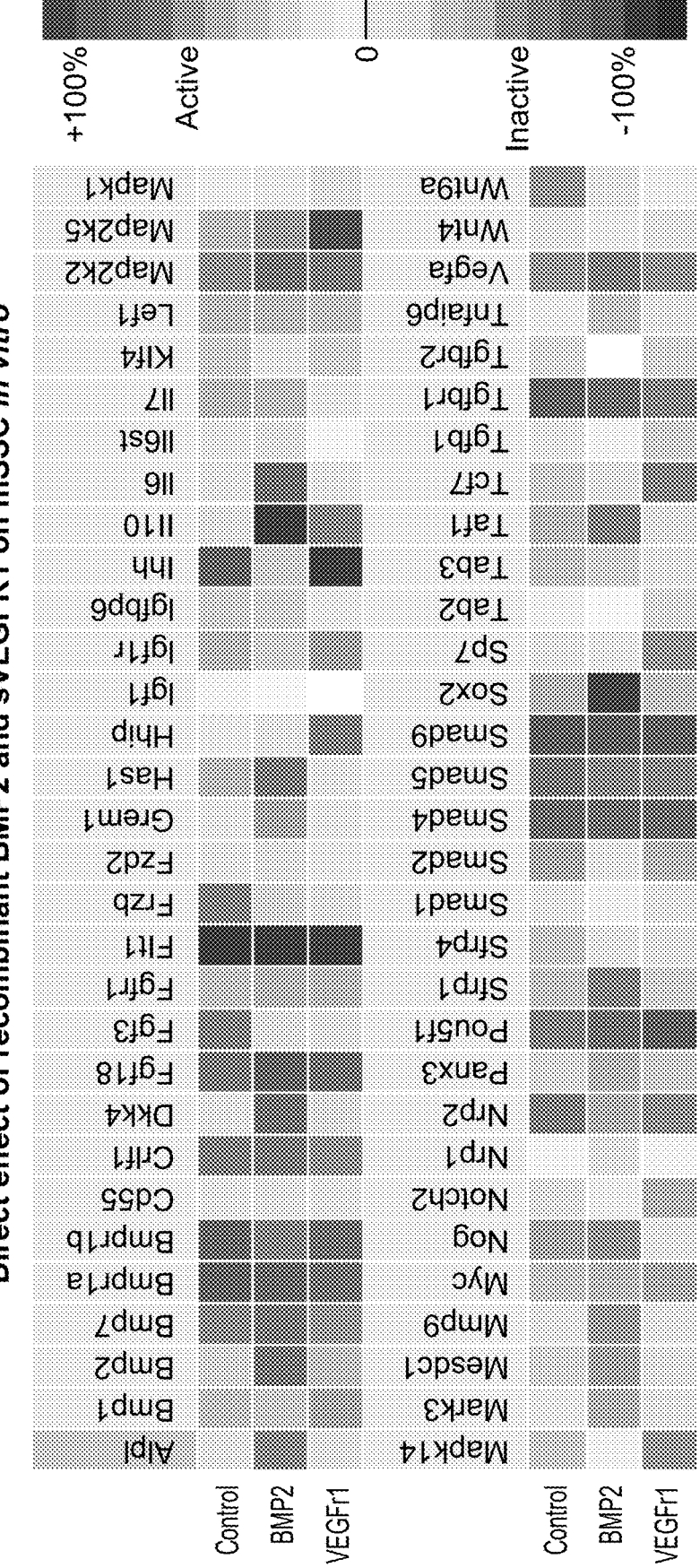

Guiding Microfracture-activated mSSC towards cartilage fates. While fibrocartilage is preferable to an exposed bone defect, its mechanical properties are inferior to articular cartilage. The ultimate goal of MF surgery is to produce articular cartilage, therefore, we asked if we could provide a niche promoting articular cartilage formation rather than fibrocartilage. Two key pathways, BMP2 and VEGF, play an important role in determining the fate of tissue remodeling and homeostasis of cartilage. BMP2 is well known as a potent osteogenic growth factor. Inhibiting VEGF signaling has been shown to reduce OA progression and fibrosis in vivo. In addition, we have also found that a combination of BMP2 with VEGF inhibition using soluble sVEGFR1 leads to cartilage formation in resting mSSC and hSSC. We also observe that BMP2 and VEGF inhibition promote expression of cartilaginous pathways on sorted mSSC in vitro, suggesting that these pathways regulate cartilage differentiation in mSSC directly (FIG. 6d). To determine how BMP2 and VEGF blockade could influence MF-activated mSSC differentiation in vivo, we co-transplanted Ad/MF mSSC with BMP2 with or without sVEGFR1. We FACS isolated and transplanted 20,000 adult MF mSSC beneath the renal capsule of NSG mice and placed a lyophilized collagen treated with combinations of BMP2 and sVEGFR1 sponge directly beside the transplanted cells then allowed the mSSC to differentiate for 4 weeks. Co9 transplantation of adult MF mSSC and BMP2 produced bone, while co-transplantation with BMP2+sVEGFR1 led to increased cartilage formation (FIG. 3e-f).

Figure 9C:
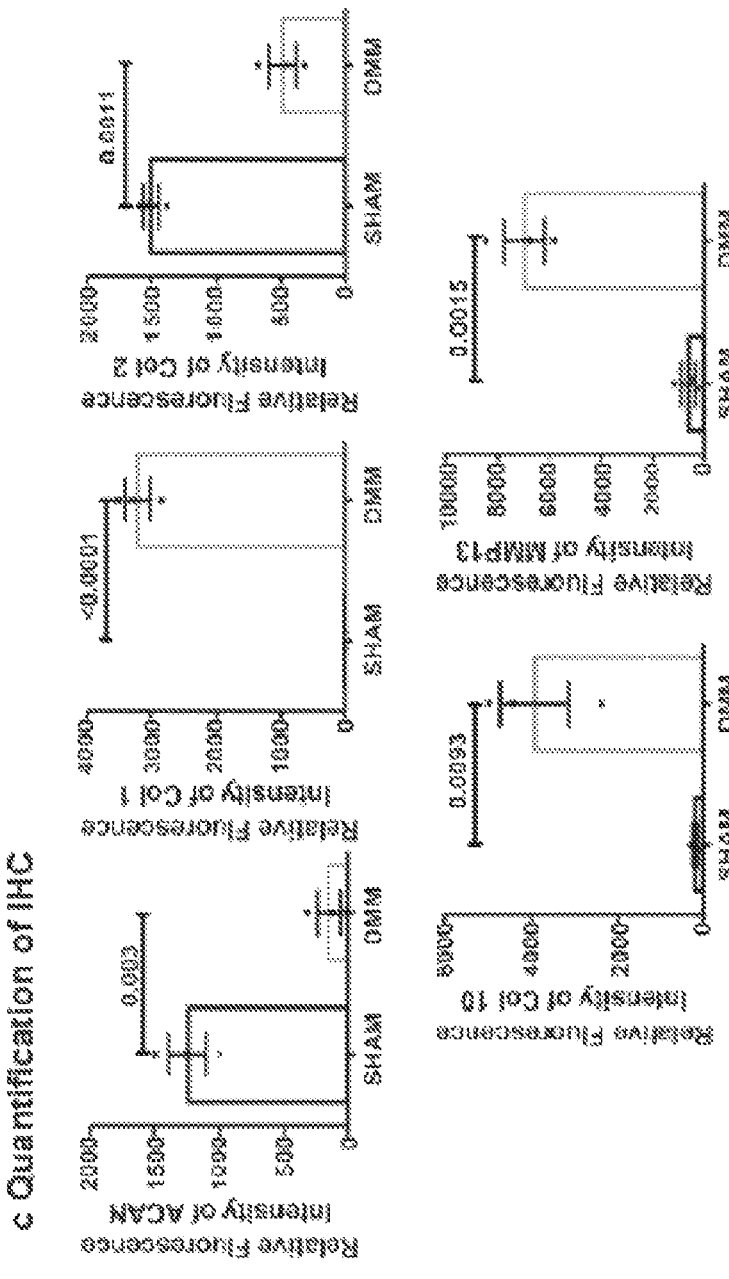
FIG. 9. OA progression. a, Schematic of the experimental outline. b, Left panels: IF of (Upper-lower) ACAN, COL 1, COL 2, COL 10, and MMP13 in sham (Left) and DMM joints (Right). Scale bars 100 μm. Right panels: Safranin 0 (upper) and pentachrome (lower) stains of sham (Left) and joints 8 weeks after destabilization of the medial meniscus (DMM) (Right) Scale bars 500 μm. N=3. c, Graphs showing quantification of IHC stains in sham versus DMM (ACAN, COL 1, COL 2, COL 10, and MMP13). Graphs show Mean+/−SEM. Student T-test. Exact P values to 2 significant figures.

Regenerating cartilage in OA joints by combining MF and niche modulating factors. Having determined that BMP2 and sVEGFR1 could guide MF-activated mSSC towards chondrogenic fates in vivo, we asked whether combining MF surgery and co-delivery of BMP2 and sVEGFR1 could stimulate cartilage regeneration in an immunocompetent, OA setting. Using our model of meniscectomy-induced OA (FIGS. 9a-c), we microfractured OA knee joints, then delivered previously validated PEG hydrogel constructs treated with combinations of BMP2 and sVEGFR1 to the MF site. We then allowed the recipient mice to heal for 4 weeks before re-isolating joints for histological analysis. We found that PEG hydrogels loaded with control PBS led to a fibrotic tissue defect with minimal cartilage or bone regeneration while PEG hydrogels loaded with BMP2 promoted significant bone formation at the MF site (FIG. 3g). In contrast, BMP2+sVEGFR1 stimulated robust formation of cartilage at the MF site that stained intensely blue for proteoglycan by Movat's Pentachrome and contained numerous morphologically distinct chondrocytes (FIG. 3g).

Figure 10:
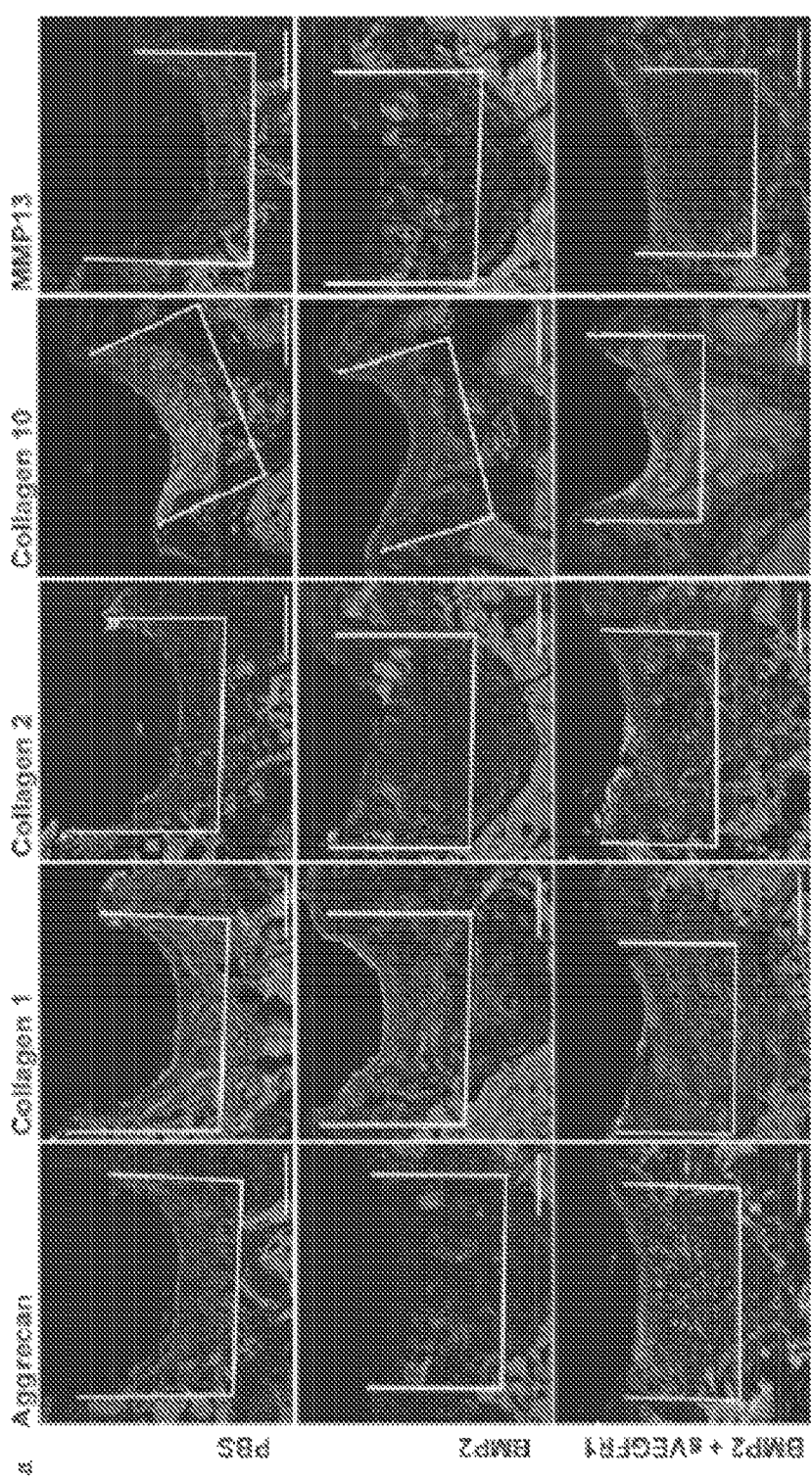
FIG. 10. IHC and quantification of OA/MF with factors at 4 weeks. a, 4-week timepoint showing respective IF of (Left-right) ACAN, COL 1, COL 2, COL 10 and 21 MMP 13 in 3 conditions (Upper row: PBS, Middle row: BMP2, Lower row: BMP2+sVEGFR1). Scale bars 250 μm. N=8. b, Graphs showing quantification of IHC stains of MF+factor (ACAN, COL 1, COL 2, COL 10 and MMP 13) at 4 weeks. Graphs show Mean+/−SEM. Ordinary one-way ANOVA test with post-hoc analysis using Šidák method to compare between specific means. Exact P values to 2 significant figures. c, IHC isotype (Left) and positive (Right) controls. d, Repeat examples of pentachrome staining of BMP2+ sVEGFR1 sections at low and high magnification. Scale bars 1 mm. N=8.
Figure 10:
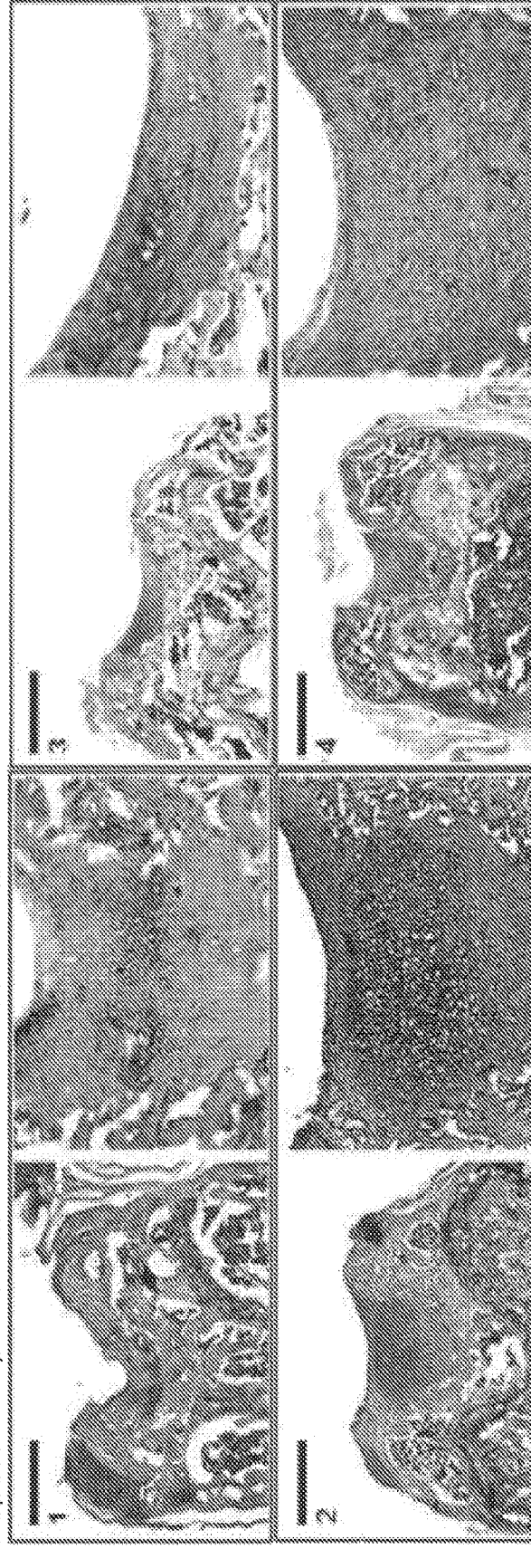
Figure 11A:
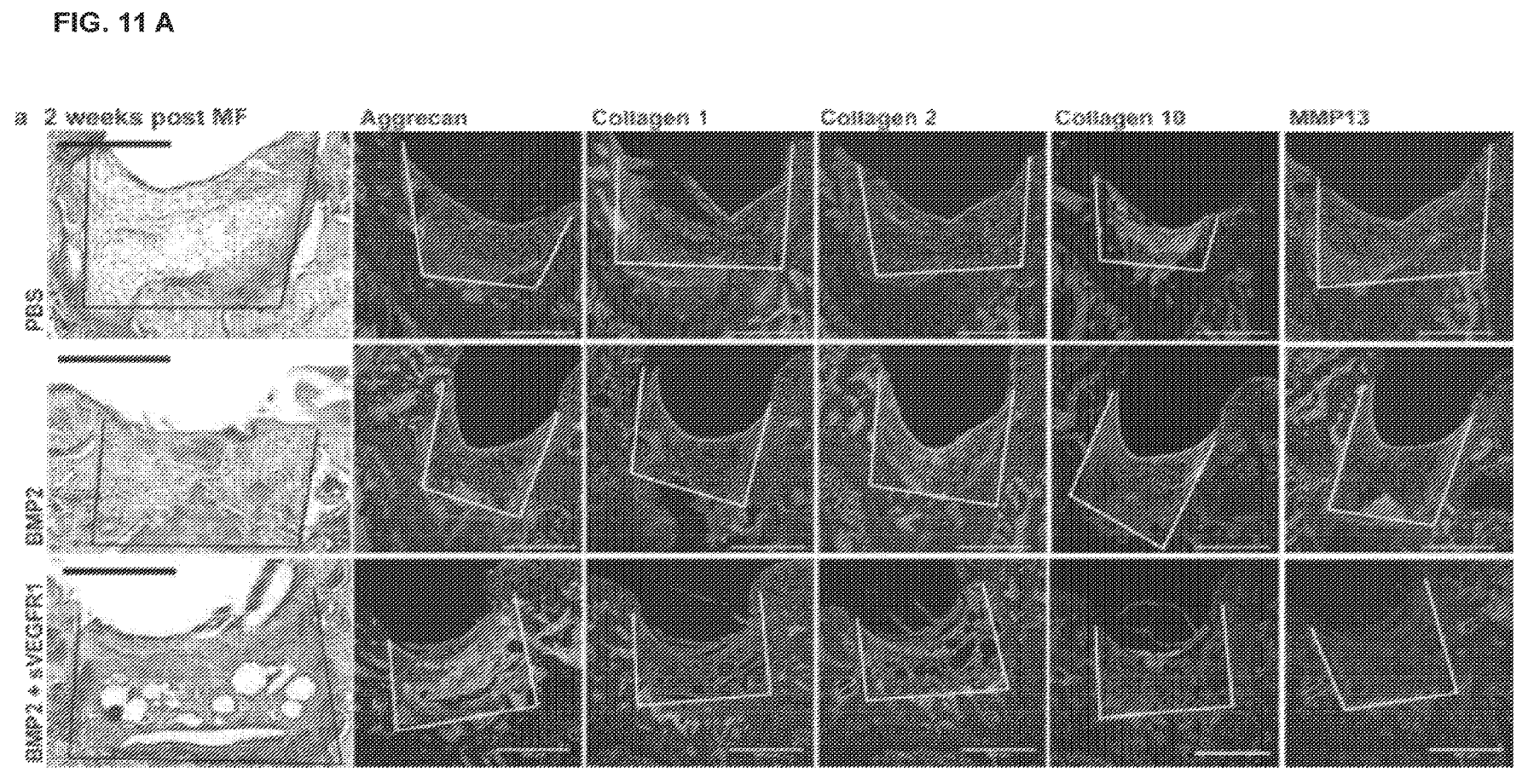
Figure 11:
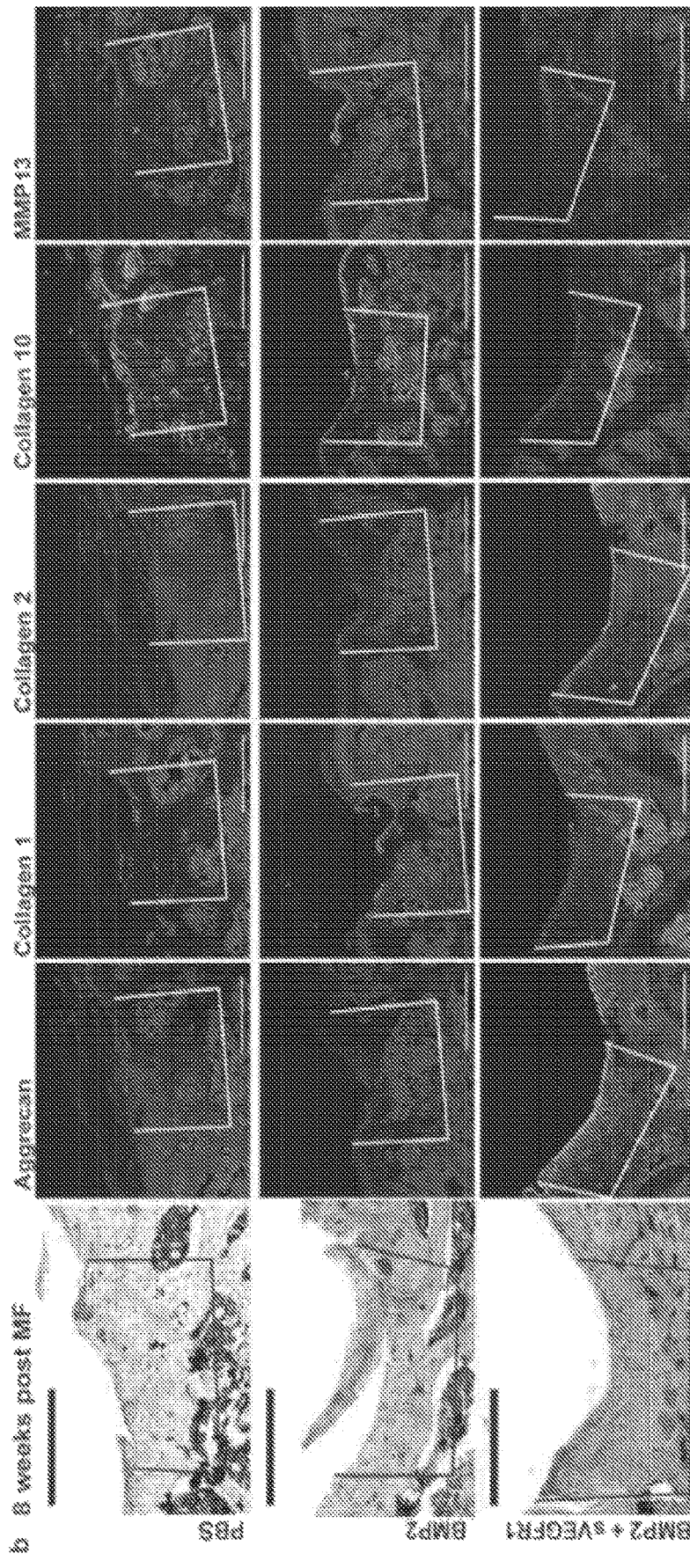
FIG. 11. Histology of OA/MF at 2 weeks and 8 weeks. a, 2-week timepoint showing pentachrome and respective IF of (Left-right) ACAN, COL 1, COL 2, COL 10 and MMP 13 in 3 conditions (Upper row: PBS; Middle row: BMP2; Lower row: BMP2+sVEGFR1). Scale bars 500 μm. N=4. b, 8-week timepoint showing pentachrome and respective IF of (Left-right) ACAN, COL 1, COL 2, COL 10 and MMP 13 in 3 conditions (upper row: PBS; middle row: BMP2; lower row: BMP2+sVEGFR1). Scale bars 500 μm. N=4 per time-point. c. Graphs showing quantification of IHC stains of MF+factor (ACAN, COL 1, COL 2, COL 10 and MMP 13). Graphs show Mean+/−SEM. Ordinary one-way ANOVA test with post-hoc analysis using Šidák method to compare between specific means. Exact P values to 2 significant figures. c, IHC isotype (Left) and positive (Right) controls.
Figure 12:
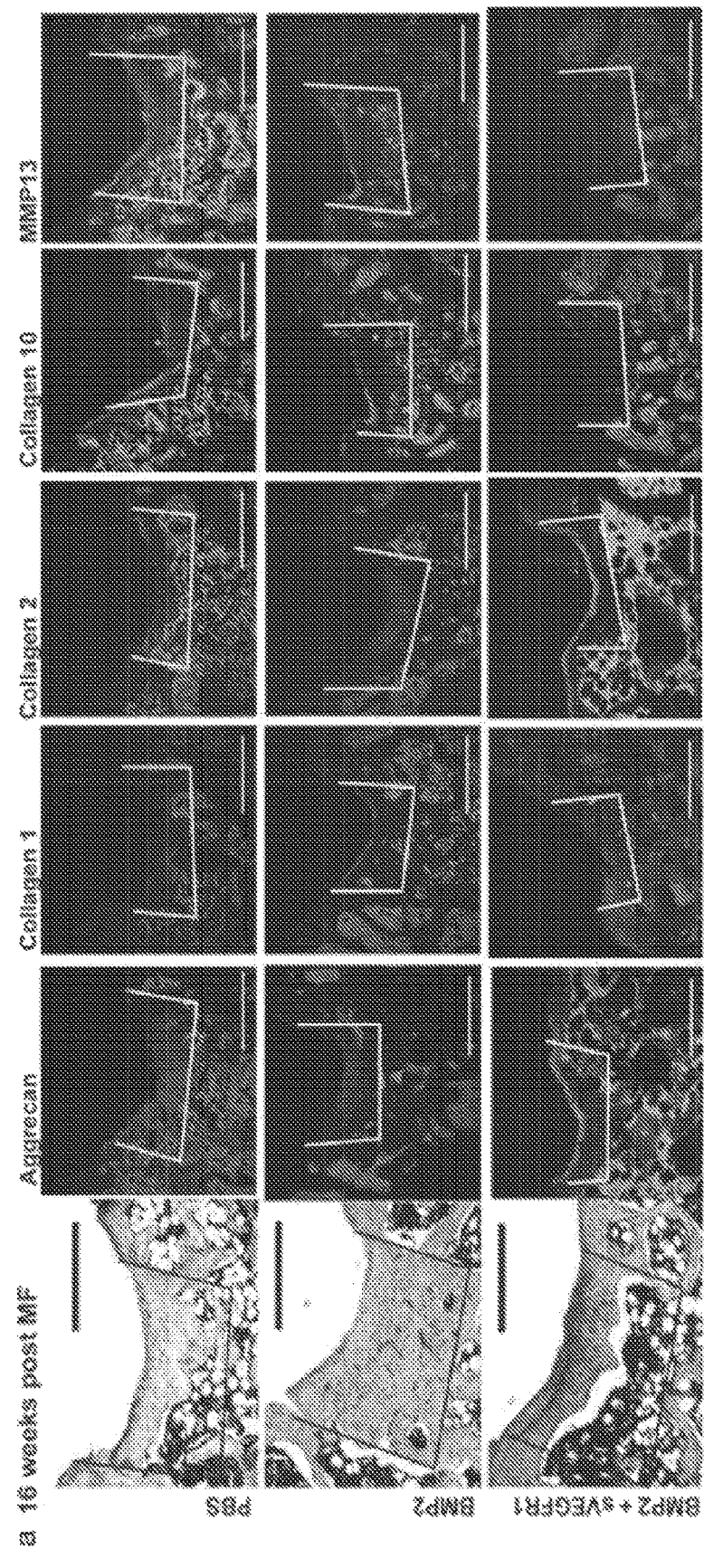
FIG. 12. Week 16 timepoint. a, 16-week timepoint showing pentachrome and respective IF of (Left-right) ACAN, COL 1, COL 2, COL 10 and MMP 13 in 3 conditions (Upper row: PBS, Middle row: BMP2, Lower row: BMP2+ sVEGFR1). Scale bars 500 μm. N=4. b, Graphs showing quantification of IHC stains of MF+factor (ACAN, COL 1, COL 2, COL 10 and MMP 13). Graphs show Mean+/−SEM. Ordinary one-way ANOVA test with post-hoc analysis using Šidák method to compare between specific means. Exact P values to 2 significant figures. c, IHC isotype (Left) and positive (Right) controls. c, (Left-right) Gross images of distal femur; respective pentachrome; 3D Peak Force Error; 3D Deformation; Force Volume 22 in 4 conditions (Upper row: PBS, Middle row: BMP2, Lower row: BMP2+ sVEGFR1, Bottom row: Uninjured) N=4. Scale bars 500 μm.
Figure 12:
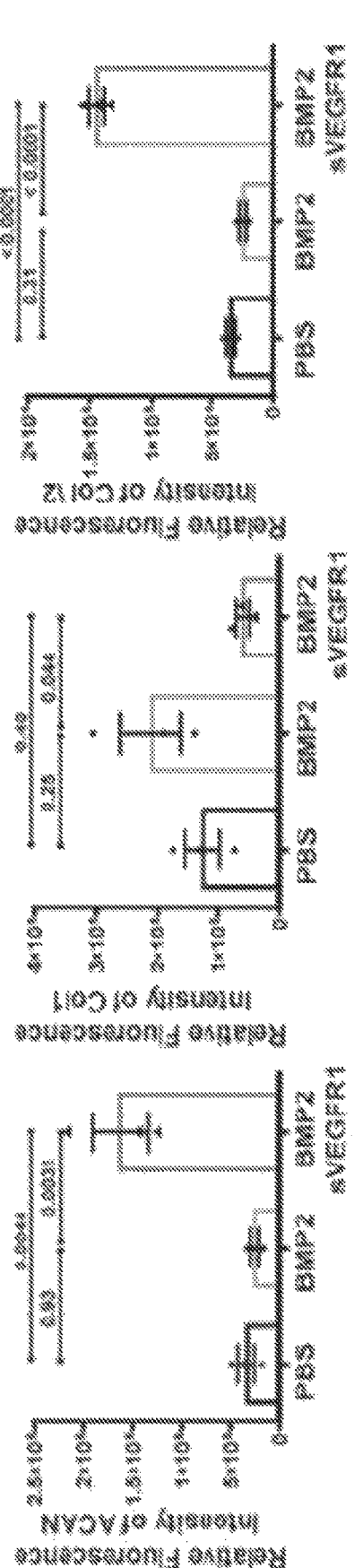
Figure 12:
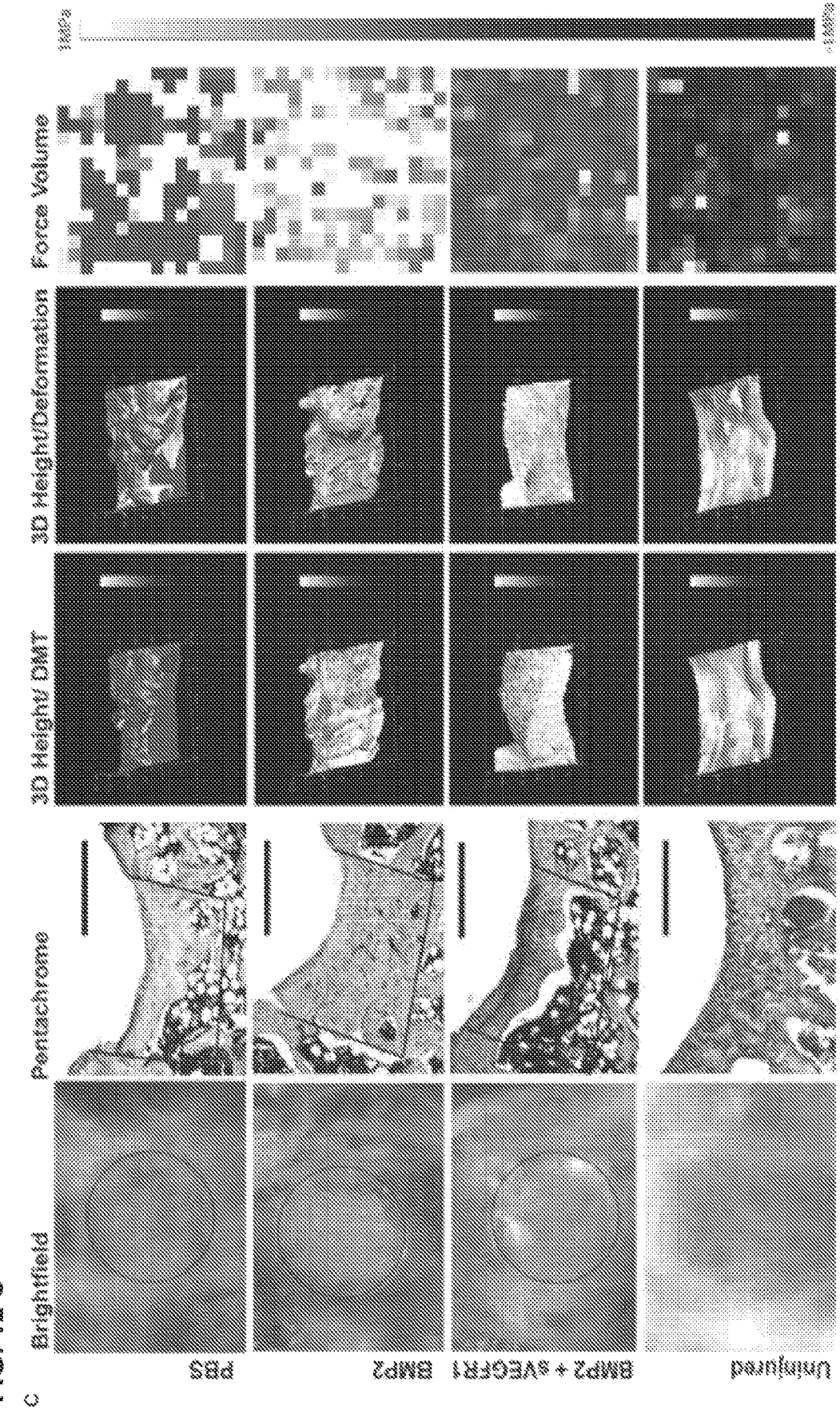

While regeneration was significantly enhanced in both the BMP2 and BMP2+sVEGFR1 groups, only the combination of sVEGFR1 with BMP2 resulted in significant cartilage formation (FIG. 3h). The regenerated cartilage also stained positive for aggrecan (ACAN) and COL 2 and negative for fibroblast markers such as COL 1 and MMP 13, suggesting that stable mature cartilage was formed (FIGS. 10a-c). Collagen10 expression, which is indicative of hypertrophic chondrocytes is also significantly diminished in the BMP2 and sVEGFR1 treatment group. The results consistently indicated that intra-articular use of BMP2 stimulates local bone formation, while BMP2+sVEGFR1 leads to stable aggrecan positive cartilage formation in a clinically relevant mouse OA model (FIG. 10d). To examine the rate and duration of cartilage formation and to exclude endochondral ossification in our BMP2+sVEGFR1-treated group, we harvested OA/MF mice at 2, 4, 8 and 10 16 weeks (FIG. 10, FIG. 11a-b, FIG. 12a-b). At 2 weeks we found that the regenerate with BMP2+sVEGFR1 already stained positive for ACAN and COL 2 on IHC. At 2 weeks PBS regenerate showed minor fibrosis and BMP2 showed some ossification suggesting some tissue remodeling at 2 weeks (FIG. 11a). We observed similar, persistent histological findings at 8 weeks (FIG. 11b) and even 16 weeks indicating stable and durable regeneration of lost cartilage (FIG. 12a-b).

Figure 13:
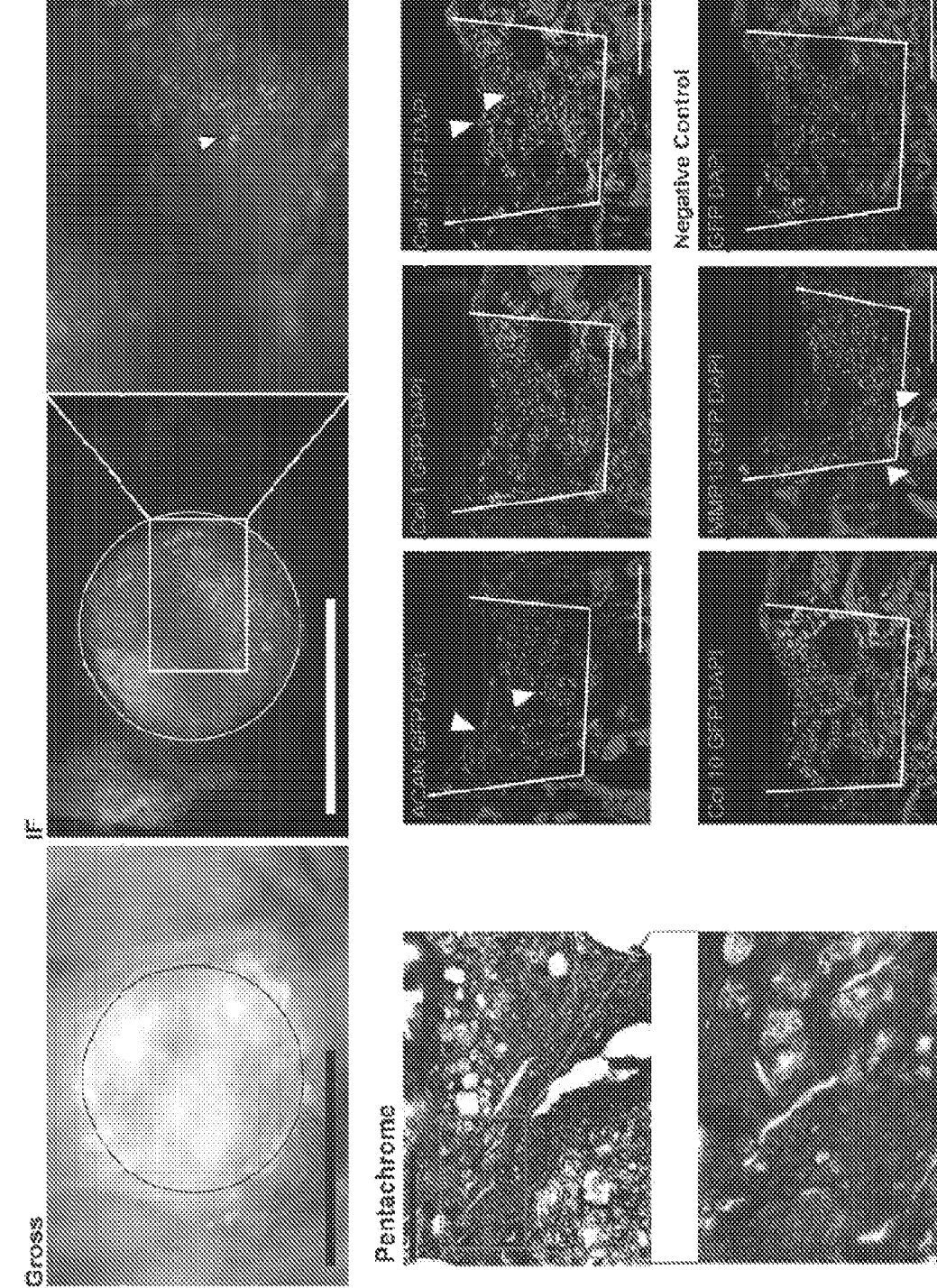
FIG. 13|Effects of aged and irradiated niches. a, Graph of mSSC/million events in normal and MF joints of adult (9 wks) and aged (1 yr) mice. b, Pentachrome stain of 2-weeks post MF surgery in aged joints with (Left-right) PBS, BMP2, and BMP2+sVEGFR1. Scale bar 500 μm. N=3. c, Schematic of the experimental outline. d, Upper panels: 4-week time-point showing gross image (Left) and IF (Right) of GFP+ Ad/MF mSSC into an irradiated joint following MF surgery. Lower panels: Pentachrome stain (Left) and respective IF of (Left-right) ACAN, COL 1, COL 2, COL 10, and MMP13 of GFP+Ad/MF mSSC into an irradiated joint following MF surgery. Positive staining marked by white arrows. A nega-tive control stain is included (Bottom right panel). Scale bars 500 μm. Graphs unless otherwise stated show Mean+/− SEM. Exact P values to 2 significant figures.

MF stimulated expansion of mSSC was significantly diminished in aged animals corresponding to reduced cartilage regeneration (FIG. 13a-b). MF-activated mSSC isolated from young adult GFP labeled mice robustly contributed to stable cartilage formation in the presence of BMP2 and sVEGFR1 when transplanted into irradiated joint tissues in which endogenous mSSCs are depleted. These data demonstrate both the potential of MF activated SSCs in generating new cartilage as well and the ability of BMP2 and sVEGFR1 in providing a cartilaginous niche (FIG. 13c,d). While we have shown histologically that the regenerate stained positive for ACAN and COL2, we wanted to further assess its mechanical qualities. Viscoelastic properties of the regenerate were assessed using Atomic Force Microscopy (AFM) 8 weeks post MF. While many groups have characterized mechanical properties of articular cartilage from larger animals with indentation techniques, given the scale of our defects, Atomic Force Microscopy was considered a more precise and delicate method to characterize the regenerate.

Figures 14A, 14B:
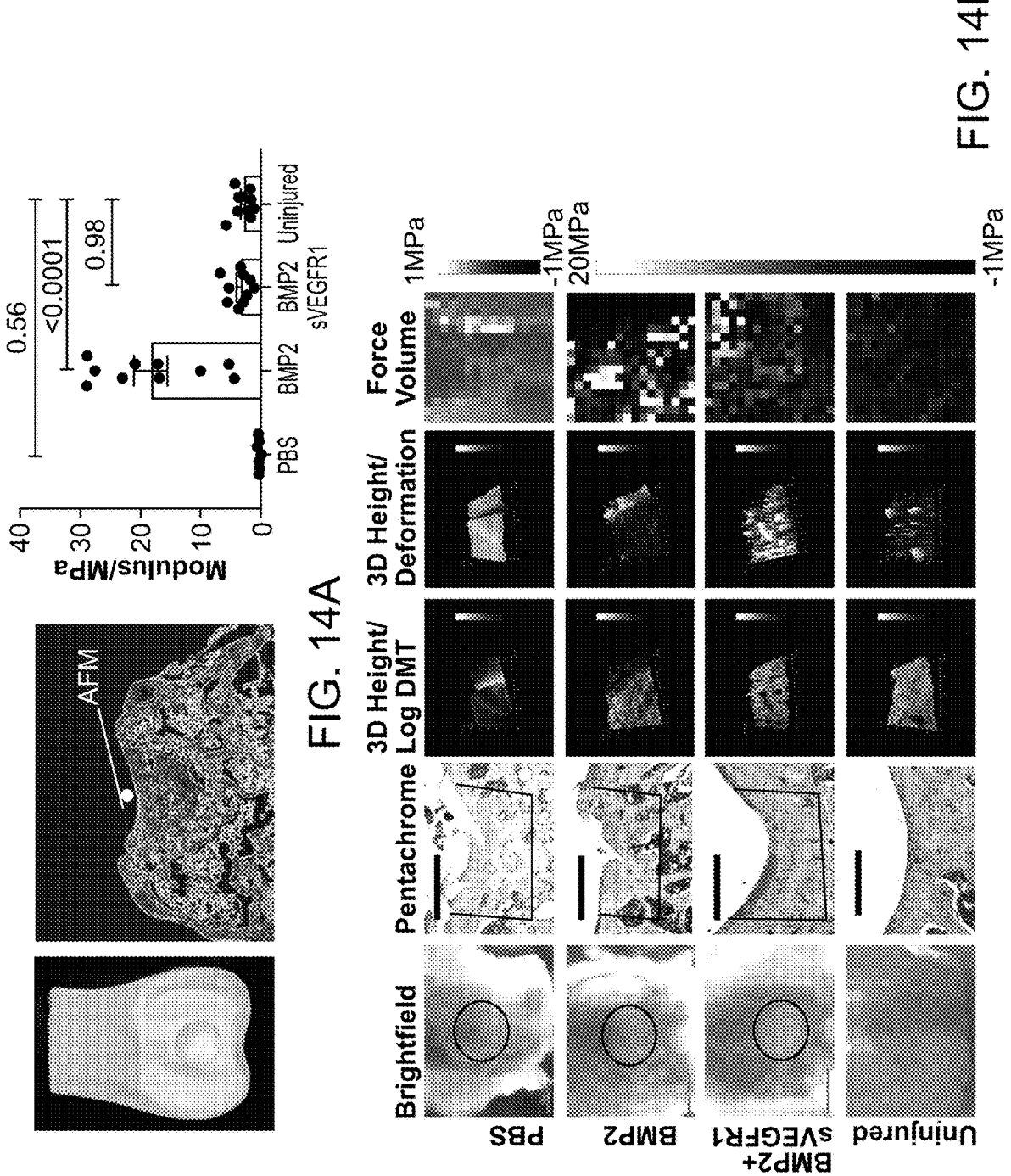
FIG. 14. Atomic Force Microscopy at 8 weeks post MF. a, (Left and middle) Schematic of Rheology experimental outline. (Right) Graph showing modulus of the regenerate (PBS, BMP2, BMP2+sVEGFR1.) Graph shows Mean+/− SEM. Ordinary oneway ANOVA test (p=<0.0001) with post-hoc analysis using Šidák method to compare between specific means. Exact P values to 2 significant figures. b, (Left-right) Gross images of distal femur; respective pen-tachrome; 3D Peak Force Error; 3D Deformation; Force Volume in 4 conditions (Upper row: PBS, Middle row: BMP2, Lower row: BMP2+sVEGFR1, Bottom row: Unin-jured) N=4. Scale bar 500 μm. c, Force graphs showing PBS (Upper left), BMP2 (Upper right), BMP2+sVEGFR1 (Lower left), and uninjured (Lower right). N=4.

Utilizing AFM with a spherical probe (FIG. 14a) we observed that the modulus of BMP2-treated regenerated was greater than that of both BMP2+sVEGFR1 regenerate and uninjured cartilage. The AFM measurements further indicated that the BMP2+sVEGFR1 regenerate had a log.DMT elastic modulus, deformation and force volume that are within the range of what is observed with uninjured cartilage (FIG. 14b). Examples of force height curves also demonstrated that BMP2+sVEGFR1 regenerates displayed similar characteristics as uninjured cartilage.

Figure 14C:
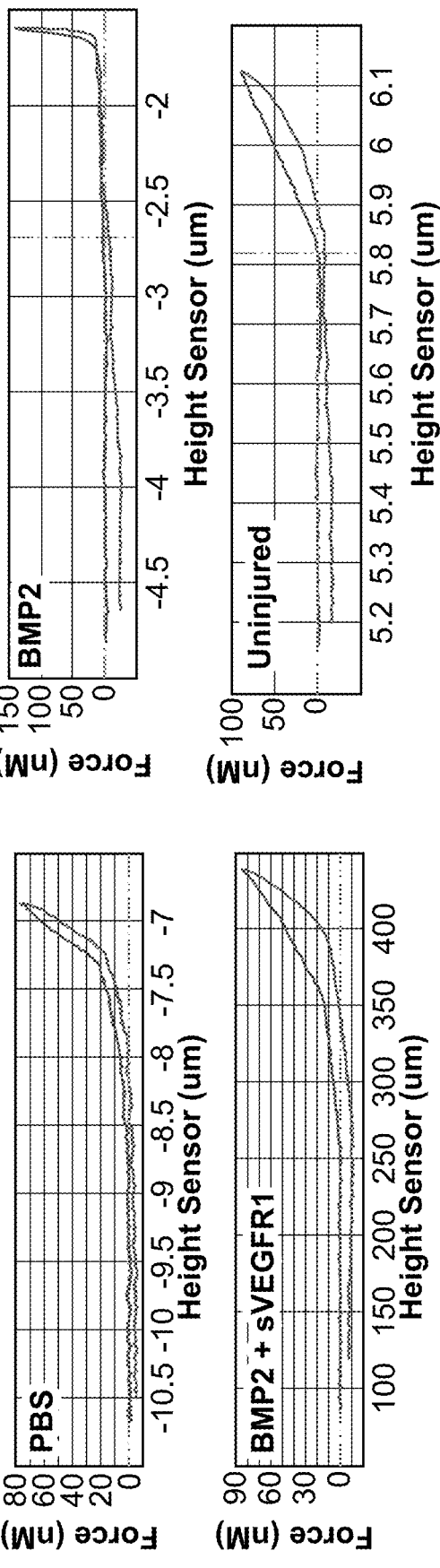

Taken together, our results indicated that combining MF activation with BMP2+sVEGFR1 induced resurfacing of OA joints with new cartilage that possessed similar biomechanical properties as uninjured cartilage (FIG. 14c). Encouragingly, the restoration of biomechanically similar cartilage in affected joints also corresponded with improved mobility parameters in the animal as measured by gait analysis (FIG. 15a) as well as enhanced pain relief (FIG. 15b,c).

Figures 4A, 4B:
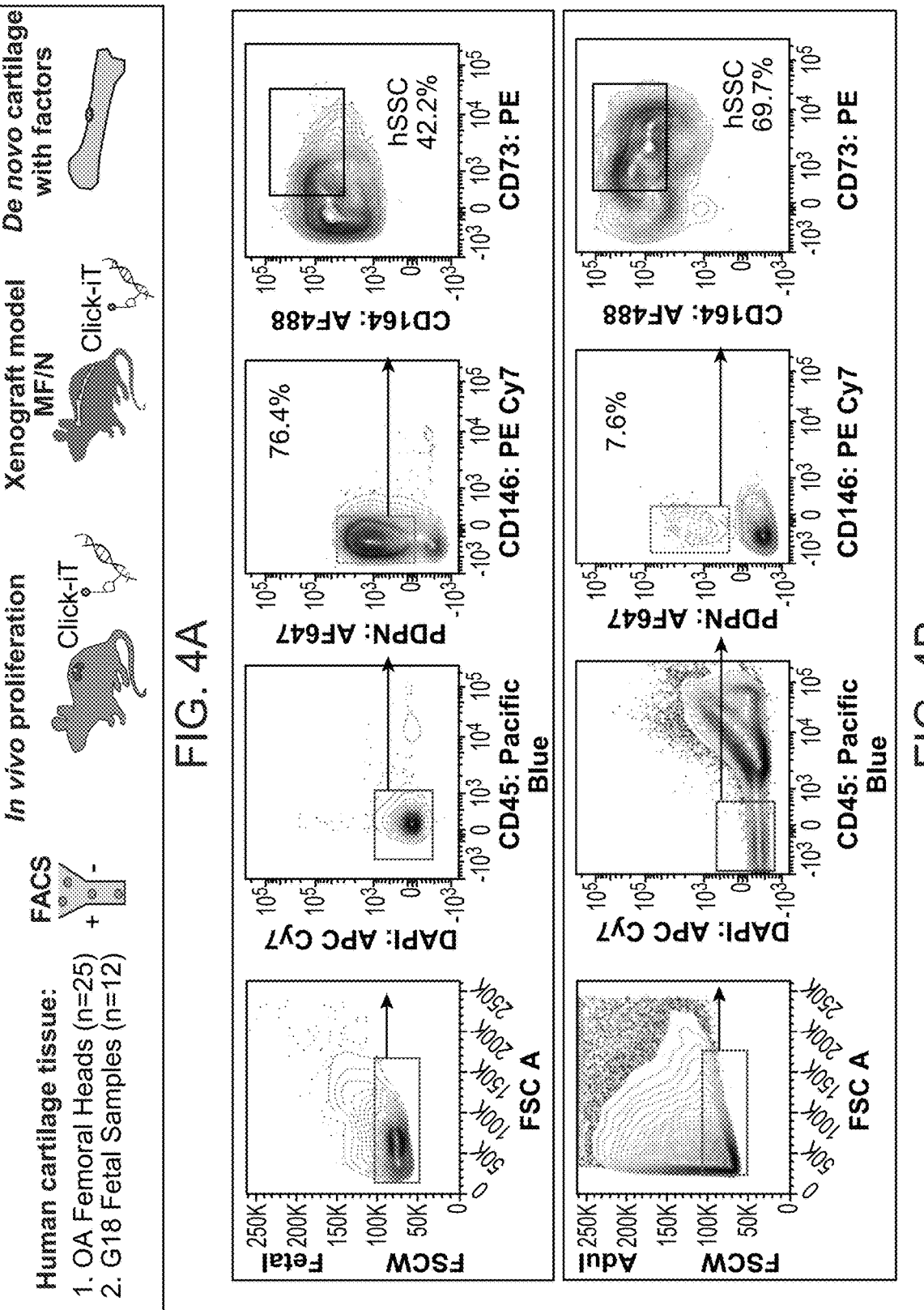
FIG. 4. Regeneration of human articular cartilage in a preclinical xenograft model. a, Schematic showing the experimental outline. In both the kidney capsule transplant model and the xenograft model Click-iT EdU assays were performed, which allows for detection of cell proliferation by EdU incorporation during DNA synthesis. b, FACS panels demonstrating the validated human articular SSC (hSSC) profile and marked difference in percentage of PDPN+CD146− cells between human fetal cartilage (Top row) and human adult cartilage (Lower row). c, Graph showing the significant reduction in hSSC with age. (Adult Cartilage N=25 20M:5F 48-90Y/O, Fetal Cartilage N=12 18 WK gestation) d, Pentachrome staining of human fetal (Top panel) and human adult (Lower panel) articular cartilage transplants into NSG mice. 4 weeks post-transplant. Scale bar 200 μm. N=8. e, Click-iT EdU assays in vivo in a renal capsule of NSG mice. Top row shows human fetal articular cartilage. Lower row shows human adult articular cartilage transplant. Scale bar 45 μm. N=8. f, Graph showing reduced cellularity of human adult transplanted cartilage. N=15. g, Left-right: Gestation week 18 human fetal phalanges transplanted subcutaneously into the dorsum of P3 RFP NSG mice; the same mouse 18 weeks post-transplant. h, (Panels left-right) GFP+ non-RFP human tissue proliferating in vivo. Scale bar 100 μm. MRI showing healthy human tissue and micro-CT showing evidence of ossification of the human diaphysis in vivo. Xenograft outlined in orange dotted line. i, Left panel: Evidence of healthy viable human fetal phalangeal tissue with schematic showing areas of MF. Right panel: 3 areas of MF on a human fetal phalangeal diaphysis as shown by white arrows. j, Graph showing an increase in hSSC post MF of human fetal phalangeal diaphyseal regions. N=15. k, Gross image of MF human fetal phalangeal diaphysis (white arrows) with hydrogels in place. Sutures mark the sites between MF. Dotted line marks the plane of sectioning. l, Schematic showing the regions of the human fetal phalangeal diaphysis that were MF and had topical factors applied. m, Top row: PBS control. Lower row: BMP2+sVEGFR1. Left panels are pentachrome stains showing cartilage (blue) within the regenerate of BMP2+ sVEGFR1. Right panels are corresponding immunofluorescence (IF) showing staining within the regenerate for (Left-right) HNA, mousespecific MHC, and COL 10. Scale bar 500 μm. N=8. n, Schematic graph showing the tissue composition changes with PBS and BMP2+sVEGFR1. Yellow signifies bone and blue signifies cartilage within the regenerate. o, Left panel: Further evidence of de novo cartilage formation on pentachrome of a MF defect with BMP2+ sVEGFR1. Scale bar 500 μm. Right panel: Effect of BMP2+ sVEGFR1 on diaphyseal de novo cartilage formation. N=8. Graphs unless otherwise stated show Mean+/−SEM. Student T-test. Exact P values to 2 significant figures.
Figures 4C, 4D, 4E, 4F, 4G:
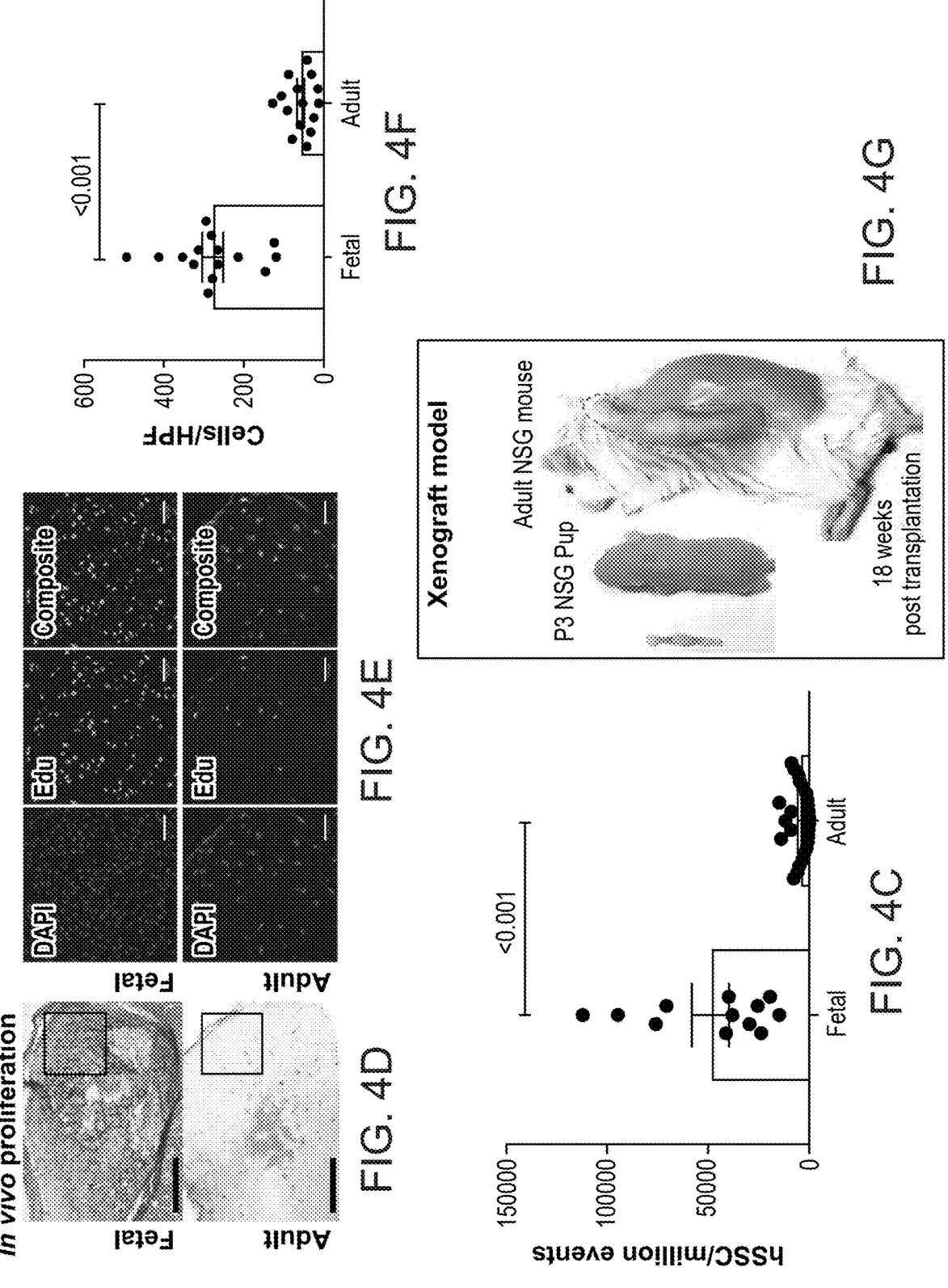

Regeneration of human articular cartilage in a human preclinical xenograft model. Thus far, we have observed that MF can induce a transient, localized expansion of mSSC in chondral tissues, despite maturity-related depletion of the resident stem cell pool. Furthermore, the MF-activated mSSC possess enhanced clonogenic activity and could be amplified and skewed towards cartilage differentiation by stimulating BMP2 signaling while antagonizing VEGF signaling. To determine if MF can elicit a similar regenerative response by hSSC we first asked if maturity also corresponds to reduced human SSC (hSSC) pools in human chondral tissues. We compared hSSC frequency in 18-week gestation human fetal distal femurs with human adult femoral heads using a validated human hSSC FACS gating strategy (FIG. 4a). We found that as with mice, there is a significant reduction in hSSC with age (FIG. 4b,c). When human fetal and adult articular cartilage were explanted into the renal capsule of NSG mice, we found that human fetal cartilage produced considerably more proteoglycan than human adult cartilage. In addition, human fetal tissue was significantly more cellular and proliferative at 4 weeks post-transplant (FIG. 4d-f). These data corroborate our findings in mice and suggest that human chondral hSSC are also depleted significantly by the onset of maturity.

Figures 4H, 4I, 4J:
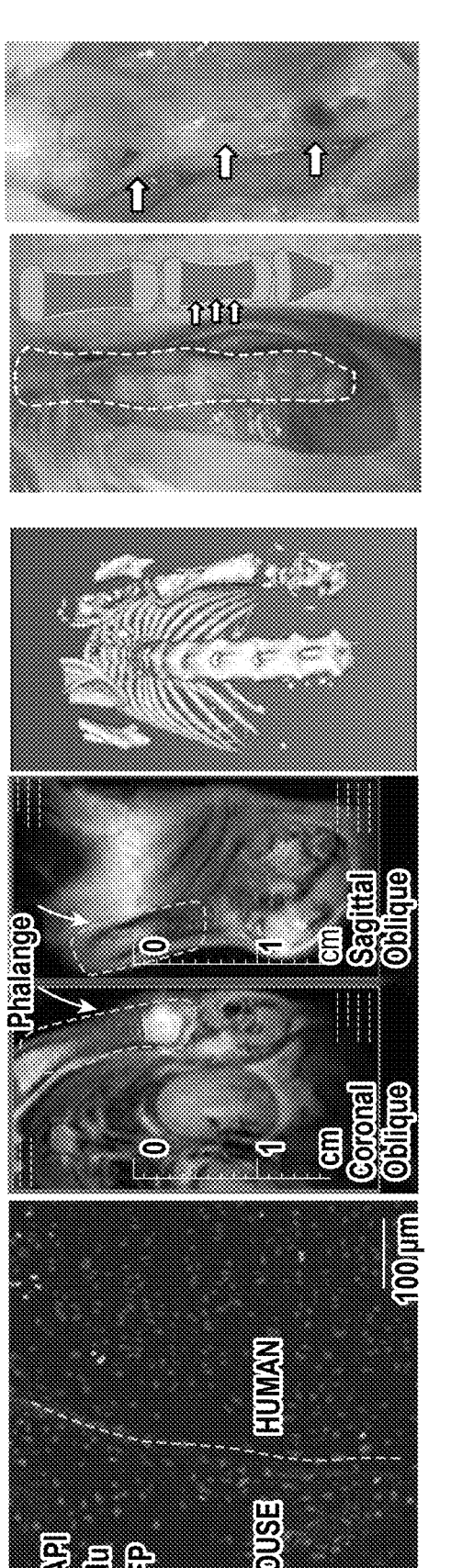
Figure 5:
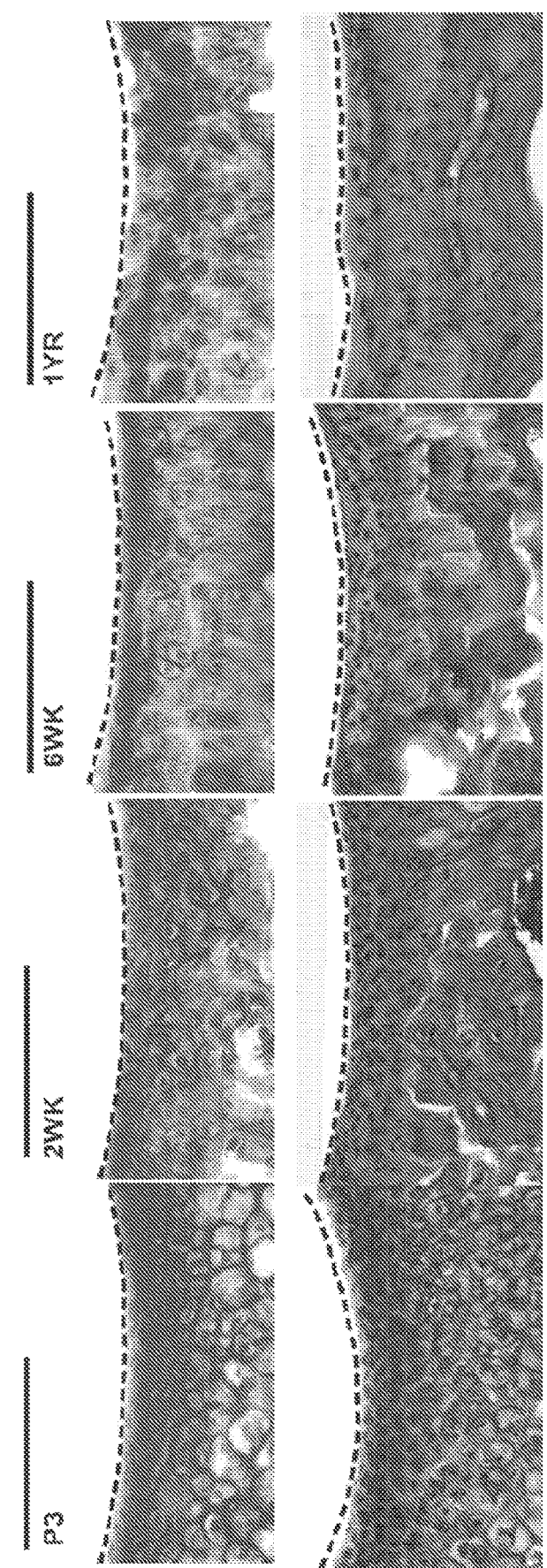
FIG. 5. Adjacent H&E stain demonstrating histomorphometric changes with age. Pentachrome images as shown in FIG. 1 (Upper panels) with adjacent H&E stains (Lower panels) showing the changes in morphology of articular cartilage with maturity (purple=cartilage, pink=extracellular material). (Left-right: P3, 2 WK, 6 WK, 1 YR). Scale bar 100 μm.

To investigate whether MF surgery could reactivate human hSSC expansion, we established a preclinical human xenograft model transplanting human 18-week gestation phalanges into the dorsum of red fluorescent protein (RFP) NSG P3 pups (FIG. 4g). Human tissue viability was confirmed by detection of numerous proliferating EdU+ cells within non-RFP human fetal phalangeal xenograft tissue in vivo as well as viable cartilage on MRI and ossification on Micro-CT (FIG. 4h). To assess if a cortical bone defect would yield a significant increase in hSSC, the viable human fetal phalangeal xenograft was acutely injured at the diaphysis (FIG. 4i). To utilize a bone niche, we chose to create a cortical bone defect at the human fetal phalangeal diaphysis rather than the articular surface of the human fetal phalangeal xenograft, as the articular surfaces are still highly cartilaginous. We observed that unicortical defect of the human fetal phalangeal diaphysis resulted in an amplification of hSSC detected by FACS, 1 week after surgery (FIG. 4j). In order to confirm if a cortical bone defect with the addition of chemical niche manipulation could stimulate de novo cartilage growth within a cortical bone niche, we injured the human fetal phalangeal diaphyseal cortex and applied hydrogels with PBS or BMP2+sVEGFR1 within the defects (FIG. 4k). As was seen in mice, BMP2+sVEGFR1 generated significantly more de novo cartilage even within the human fetal phalangeal cortical bone niche compared with PBS (FIG. 4l-o).

Paralleling the results we saw in our mouse mSSC model, our human data confirmed the role that MF-mechanical stimulus had in activating local SSC populations and supported the role of BMP2 and VEGF inhibition in regenerating cartilage. Our in vivo xenograft system establishes a human preclinical model to test whether MF combined with BMP2 and VEGFi could induce SSC derived cartilage formation in living human bones. Clinical studies, in the settings of acute cartilage defects or hand osteoarthritis can provide good clinical opportunities to test the efficacy of this approach in human patients.

Figure 16:
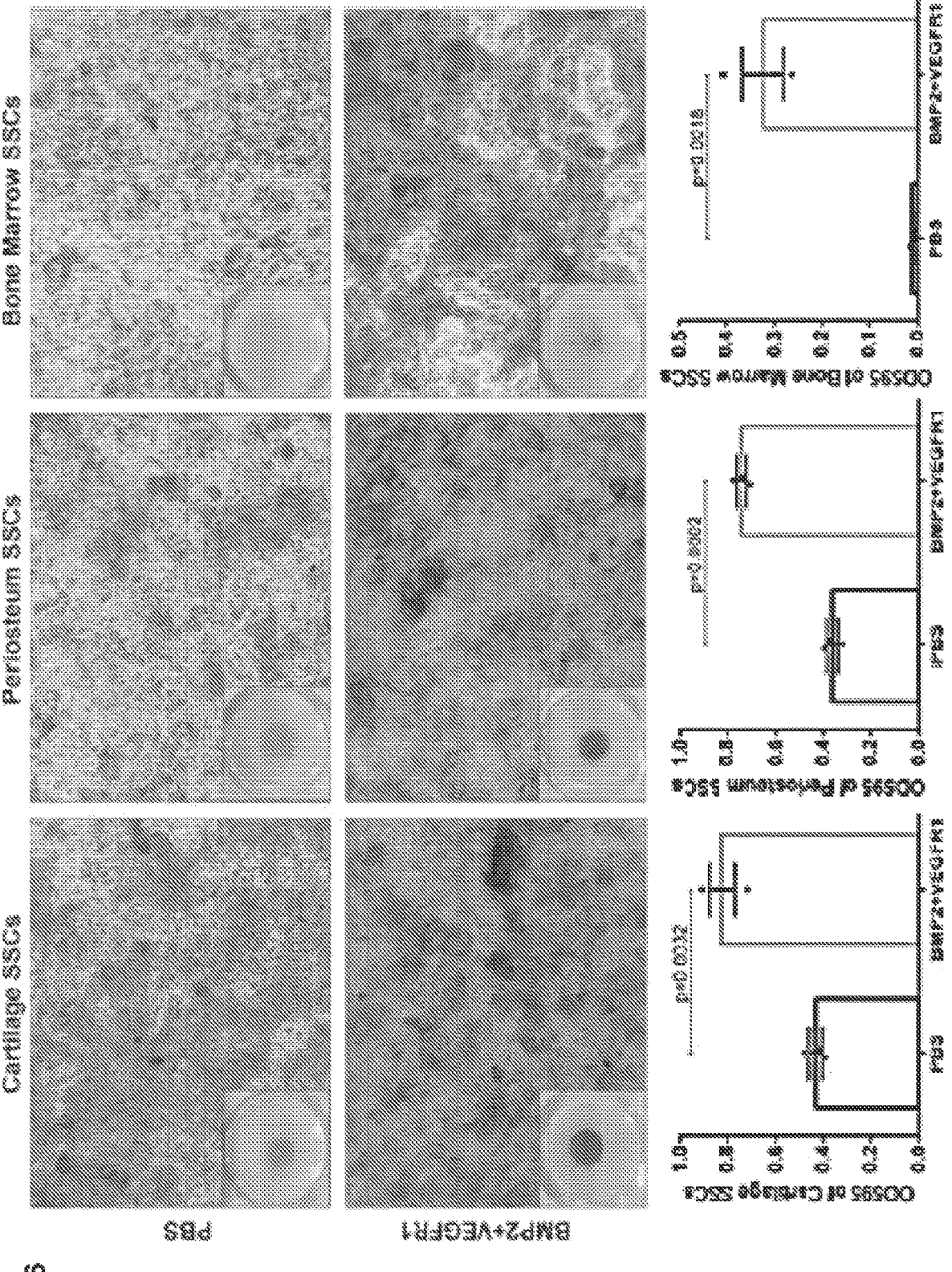
FIG. 16. Comparison of mSSCs isolated from Chondral cartilage, Bone Marrow, and Periosteum. Alcian blue stain-ing of Ad and Ad/MF mSSCs (Left) and mBCSPs (Right), and graph representing amount of alcian blue stain detected (Bottom).

Awakening of resident stem cell populations for tissue regeneration. Tissue-specific stem cells are necessary for formation and maintenance of many tissue types. Emerging evidence suggests that in some adult tissues there is no or diminished resident stem cell populations. Since adult articular cartilage possesses little regenerative ability compared to bone tissues, we initially suspected that skeletal stem cells (SSC) may no longer be present in adult cartilage tissues. Using our previously described methods for isolating functionally-defined mSSC and hSSC by FACS, we found that the frequency of adult SSC are significantly lower than juvenile or fetal tissues. However, mature articular cartilage tissues in both mice and humans still contain reservoirs of SSC. We have found that these resident pools of SSC can be reactivated in response to a local acute injury following MF and these "activated" SSC contain enhanced chondrogenic potential, reflecting alterations at the transcriptomic level. These findings led us to develop a multi-faceted approach for successful regeneration of articular cartilage. Resident SSC are first "activated" by a local MF surgery, expanded by local delivery of BMP2 and guided towards cartilage using VEGF blockade, which repress osteogenic and fibroblastic fates (FIG. 16). The chondrogenic potential of BMP2 with sVEGFR1 has been shown in mouse and human studies and with FDA-approved versions of BMP2 (Infuse) and VEGF signaling blockage (Avastin) already in clinical use, these factors have the potential to be used in combination with MF surgery for cases of OA cartilage regeneration.

Our study further demonstrates that localized, acute injuries can present a powerful extrinsic cue to resident stem cells even in adult tissues with poor regenerative potential. Acute injury can dramatically alter resident stem cell behavior and provide opportunities for further enhancing their regenerative ability by specific modulation of their regenerative niche. While other studies have investigated disease progression of OA, to our knowledge, this is one of the first studies that has shown effective, stable articular cartilage reformation through the lens of resident SSC-specific activation and biochemical niche differentiation fate control.

Materials and Methods

Mouse MF model. 9-week old, skeletally mature, sex-matched C57BL/6 or β Actin-Cre$^{ERT}$/Rainbow mice were used to examine the effect of MF on the resident mSSC population. Under general anesthesia, (Isoflurane) after assessment of pain response with toe pinch, we made a 5 mm incision medial to knee, reflected the patella laterally, applied a drop of sterile 0.9% sodium chloride and flexed the knee to expose the femoral condyles. Microfracturing was performed on the articular surface of the left femur (0.1 mm diameter to access underling subchondral bone). The right femur underwent incisions to expose patella but without MF and acted as a control (sham). The patella was repositioned. The incision was closed with 6-0 prolene suture.

Mouse OA model. General Anesthetic with Inhaled Isoflurane and a pre-operative dose of 0.5 ml/kg of buprenorphine SR. Routine preparation and surgical draping of the animal around surgical site included: shaving the leg, cleaning thoroughly with 70% alcohol/betadine and draping with sterile gauze. Heat-sterilized surgical instruments. 5 mm incision made medial to knee. The patella was reflected laterally. A drop of sterile 0.9% sodium chloride was applied. The knee was flexed to expose the femoral condyles. A small vertical incision was made in the medial meniscus. The patella was repositioned. The incision was closed with 6-0 prolene.

Human Xenograft MF model. Fetal 10-18-week old phalanges were dissected and transplanted under the dorsum of immunocompromised P3 RFP NSG pups. The xenograft model was then left for at least 6-18 weeks to ensure optimal xenograft engraftment. After engraftment, under general anesthesia (Isoflurane) the graft was accessed and the diaphyseal cortical surfaces of the middle phalangeal bone underwent MF. Non-MF areas in the proximal and distal phalangeal diaphysis served as controls.

Mouse Parabiosis model. To investigate the effect of circulating cells to form the regenerate after MF we parabiosed GFP+ Homozygous mice with C57BL/6. Both mice were positioned side by side in the supine position with the non-GFP mouse on the right and the GFP+ mouse on the left. Under general anesthesia (Isoflurane), we made a longitudinal (midaxial line) incision from knee to elbow on the right side of the C57BL/6 and the left side of the GFP+ mouse. Deep 4-0 prolene sutures were placed uniformly through the muscle bellies of both mice along the quadriceps, obliques, latissimus dorsi and triceps. The skin was closed with 6-0 prolene. For confirmation of adequate chimerism we FACS analyzed the circulation of the non GPF mouse showing GFP+ cells at 4 weeks by a blood draw from a tail vein assay of the C57BL/6 mice at 4 weeks. After confirming cross circulation at 4 weeks, MF surgery was performed on the left knee of the non-GFP parabiont, using a technique described above in the Mouse MF model in the C57BL/6 mouse.

Clonal analysis. We accessed clonal skeletogenic activity in male Rainbow mouse model crossed with ubiquitous β Actin-Cre$^{ERT}$ driver. Systemic induction by Intraperitoneal administration of Tamoxifen 200 mg/kg for 5 days labelled all cells. The rainbow reporter is a multi-color Cre-dependent marker system with a four-color construct. Once recombination occurs, cells are randomly and genetically marked with a color (1 of 8 total colors). All daughter cells will inherit that same color. The systemic contribution to clonality was then assessed. Fixation, decalcification and embedding of the isolated knee joints was performed as described by our group. Prospective isolation and analysis of mouse SSC using fluorescence-activated cell sorting (FACS). The region of interest (distal femur) was dissected out and cells were isolated with a combination of mechanical and collagenase digestion. The solution was then centrifuged. The supernatant was removed with the remaining cell pellet resuspended in FACS buffered solution. The remaining cells were then stained for antibodies to include: CD45, Ter119, CD202b, Thy1.1, Thy 1.2, CD105, CD51, 6C3, and Streptavidin-conjugated antibody for CD200 as used before by Chan et al. Propidium Iodide (PI) was used to label and exclude any dead cells. FACS analysis was performed on FACS Aria II Instrument.

Prospective isolation and analysis of human SSC using fluorescence-activated cell sorting (FACS). The region of interest was dissected out and serially digested with the collagenase buffer supplemented with DNase in constant agitation at 37° C. for 20 minutes. This was repeated 3 times in total. Each digest was filtered through a 70 μm filter and the collagenase buffer was neutralized with FACS buffered solution. The solution was then centrifuged. The supernatant was removed with the remaining cell pellet resuspended in FACS buffered solution. The remaining cells were stained for antibodies to include: CD45, CD235ab, Tie2, CD31, CD146, PDPN, CD73 and CD164. DAPI was used to label and exclude any dead cells 24. FACS analysis was performed on FACS Aria II Instrument (BD Biosciences, San Jose, CA) using a 100 μm nozzle. FACS analysis was analyzed and sorted for cell population to include SSC, BCSP and PCP populations. Populations were double sorted for purity.

Determining Colony Forming capabilities. Purified populations of mouse and human SSC were harvested by FACS and plated directly in N=3 on pre-coated (0.1% gelatin) culture plates. There were a uniform 1,000 cells per well in a 10 cm2 plate. The media used was MEMalpha medium with 20% FCS and 1% penicillin-streptomycin. Conditions were set at low 02 (2% atmospheric 02 and 7.5% CO2). The Colony Forming Units (CFU) were assessed at 2 weeks after plating using an inverted microscope at ×40 magnification.

In vivo differentiation assays. After isolation of the respective cell using FACS, 20,000 cells were collected and resuspended in 2 μl matrigel. The cellular mix was then injected into either the renal capsule or orthotopic cartilaginous defect. The animals were then euthanized 4 weeks post transplantation.

Tissue Preparation. Fixation, decalcification and embedding of the isolated knee joints was performed using: 2% Paraformaldehyde at 4° C. for 24 hours, 0.4M EDTA in PBS (pH 7.2) at 4° C. for 2 weeks. Embedded: OCT after 24 hours in 30% sucrose. 8 μm slices were made with a microtome in a coronal plane.

Collagen sponge preparation. Collagen sponges (Integra LifeSciences REF. 1690-ZZ) were cut to a dimension of 5 mm³. Factors included: recombinant mouse/human BMP2 (R&D 355-BM/CF), recombinant mouse sVEGFR1 (R&D 471-F1/CF) and recombinant human sVEGFR1 (R&D 321-F1/CF) which were reconstituted as per the manufacturers' guidelines. The sponges were lyophilized and stored at −80° C.

Hydrogel fabrication. Eight-arm poly(ethylene glycol) (PEG) monomers with end groups of 30 norbornene (MW 10 kDa) or mercaptoacetic ester (MW 10 kDa) were dissolved in phosphate buffered saline (PBS) at a concentration of 20% (w/v). Photoinitiator lithium phenyl-2,4,6-trimethylbenzoylphosphinate was then added to each solution to make a concentration of 0.05% (w/v). The two polymer solutions were mixed at a 1:1 volume ratio to obtain a hydrogel precursor solution. Recombinant BMP2 and sVEGFR1 (R&D Systems) were added to precursor solution to reach predetermined loading amount. Solutions were sandwiched between two slides with thickness of 400 μm and exposed to UV (365 nm, 4 mW/cm2) for 5 min. The hydrogels were made with volume of 1 μL or 10 μL. The growth factor loading per each 6 μL hydrogel included: 3 μg BMP2+/−25 μg sVEGFR1. The hydrogels were made without growth factors and served as controls.

Determining proliferative capacity of cells. To determine the proliferative capacity of the cells we pulse-injected the mice with 50 mg/kg of EdU twice weekly for 1 week. For histology: The mice were euthanized at 1 week. After tissue preparation we used a Click-iT reaction by Invitrogen Thermofisher (as per manufacturer's guidelines)—a copper-catalyzed azide—alkyne cycloaddition—using a fluorescent Alexa Fluor 488 to detect the incorporated EdU.

EdU Intracellular FACS. To assess the proliferative capacity of SSC and BCSP populations we first FACS the populations into buffered solution. Then we fixed the cells and permeabilized the cells using BD fix perm kit. When the cells were fixed and permeabilized, we then performed the ClickiT EdU assay on the FACS-isolated cells. Following the Click-iT EdU reaction we then re-FACS the purified SSC and BCSP populations assessing GFP signal changes between the MF and uninjured groups.

Definition of fibrocartilage by: Movat's Pentachrome staining. Sections were stained using Movat's Pentachrome. The outcomes were reported by expert histopathologists who were blinded to the experimental groups. Immunofluorescence (IF) of ACAN, COL 1, COL 2 and MMP 13. IF staining involved: rehydration and staining with Rabbit anti-mouse or antihuman primary to either ACAN, COL 1, COL 2, and MMP 13 (diluted to 1:500) overnight at 4° C. The secondary Goat anti-rabbit AF-488 was added the following day. Fluorescence 31 microscopy (Leica TCS Sp8) was used to assess for FITC tagged secondary to ACAN, COL 1, COL 2, and MMP 13.

Atomic Force Microscopy. 8 weeks post Microfracture and application of hydrogels the mice were euthanized. Distal Femurs were then imaged grossly. Utilizing a microtome blade the defect was bisected. Half of the tissue was immediately fixed in 4% PFA (and processed as usual) and the other half of the freshly isolated tissue was then dissected further and cleaned. The tissue was then fixed to a slide glass utilizing tissue glue. The samples were hydrated in protease-free PBS to prevent tissue degradation. The samples were then imaged on a Bruker Resolve Bio-AFM (Bio-AFM). We utilized a pre-calibrated set of Nanotools 40 N/m B50-NCH biosphere spherical probes. All variables including Spring constant, Resonant frequency in air and Quality factor in air was kept constant throughout experimental groups. Analysis was performed utilizing Nanoscope Analysis 1.9 Software.

Gait Analysis. Mouse gait is analyzed using the CatWalk XT (Noldus Information Technology, Wageningen, The Netherlands), an automated gait analysis system which assesses motor performance. A video camera records from below while each subject walks unforced across an illuminated gate platform. The software calculates statistics based on the footprints and body weight distribution.

Statistical Analysis. Statistical analysis was done using a ratio paired Student T test or an ANOVA test where appropriate. Software used for statistical analysis was Prism 7 Graph Pad. Exact P values were calculated and presented to 2 significant figures. Reporting Summary. Additional information regarding study design is available at Nature Research Reporting Summary linked to this article.

REFERENCES

Robinson, W. H. et al. Low-grade inflammation as a key mediator of the pathogenesis of osteoarthritis. *Nat Rev Rheumatol* 12, 580-592, doi:10.1038/nrrheum.2016.136 (2016).

Rahmati, M., Mobasheri, A. & Mozafari, M. Inflammatory mediators in osteoarthritis: A critical review of the state-of-the-art, current prospects, and future challenges. *Bone* 85, 81-90, doi:10.1016/j.bone.2016.01.019 (2016).

Marques-Rocha, J. L. et al. Noncoding RNAs, cytokines, and inflammation-related diseases. *FASEB J* 29, 3595-3611, doi:10.1096/fj.14-260323 (2015).

Liu-Bryan, R. & Terkeltaub, R. Emerging regulators of the inflammatory process in osteoarthritis. *Nat Rev Rheumatol* 11, 35-44, doi:10.1038/nrrheum.2014.162 (2015).

Hoemann, C. D. et al. Chondroinduction Is the Main Cartilage Repair Response to Microfracture and Microfracture With BST-CarGel: Results as Shown by ICRS-II Histological Scoring and a Novel Zonal Collagen Type Scoring Method of Human Clinical Biopsy Specimens. *Am J Sports Med* 43, 2469-2480, doi:10.1177/0363546515593943 (2015).

Mithoefer, K., McAdams, T., Williams, R. J., Kreuz, P. C. & Mandelbaum, B. R. Clinical efficacy of the microfracture technique for articular cartilage repair in the knee: an evidence-based systematic analysis. *Am J Sports Med* 37, 2053-2063, doi:10.1177/0363546508328414 (2009).

Goldberg, A., Mitchell, K., Soans, J., Kim, L. & Zaidi, R. The use of mesenchymal stem cells for cartilage repair and regeneration: a systematic review. *J Orthop Surg Res* 12, 39, doi:10.1186/s13018-017-0534-y (2017).

Vos, T. et al. Years lived with disability (YLDs) for 1160 sequelae of 289 diseases and injuries 1990-2010: a systematic analysis for the Global Burden of Disease Study 2010. *Lancet* 380, 2163-2196, doi:10.1016/50140-6736(12)61729-2 (2012).

Murray, C. J. et al. The state of US health, 1990-2010: burden of diseases, injuries, and risk factors. *JAMA* 310, 591-608, doi:10.1001/jama.2013.13805 (2013).

Hootman, J. M., Helmick, C. G., Barbour, K. E., Theis, K. A. & Boring, M. A. Updated Projected Prevalence of Self-Reported Doctor-Diagnosed Arthritis and Arthritis— Attributable Activity Limitation Among US Adults, 2015-2040. *Arthritis Rheumatol* 68, 1582-1587, doi:10.1002/art.39692 (2016).

Johnson, V. L. & Hunter, D. J. The epidemiology of osteoarthritis. *Best Pract Res Clin Rheumatol* 28, 5-15, doi:10.1016/j.berh.2014.01.004 (2014).

Marshall, M., Watt, F. E., Vincent, T. L. & Dziedzic, K. Hand osteoarthritis: clinical phenotypes, molecular mechanisms and disease management. *Nat Rev Rheumatol* 14, 641-656, doi:10.1038/s41584-018-0095-4 (2018).

Bijlsma, J. W., Berenbaum, F. & Lafeber, F. P. Osteoarthritis: an update with relevance for clinical practice. *Lancet* 377, 2115-2126, doi:10.1016/50140-6736(11)60243-2 (2011).

Steadman, J. R., Rodkey, W. G., Briggs, K. K. & Rodrigo, J. J. [The microfracture technic in the management of complete cartilage defects in the knee joint]. *Orthopade* 28, 26-32 (1999).

Makris, E. A., Gomoll, A. H., Malizos, K. N., Hu, J. C. & Athanasiou, K. A. Repair and tissue engineering techniques for articular cartilage. *Nat Rev Rheumatol* 11, 21-34, doi:10.1038/nrrheum.2014.157 (2015).

Knutsen, G. et al. Autologous chondrocyte implantation compared with microfracture in the knee. A randomized trial. *J Bone Joint Surg Am* 86-A, 455-464 (2004).

Devitt, B. M., Bell, S. W., Webster, K. E., Feller, J. A. & Whitehead, T. S. Surgical treatments of cartilage defects of the knee: Systematic review of randomised controlled trials. *Knee* 24, 508-517, doi:10.1016/j.knee.2016.12.002 (2017).

Vanlauwe, J. et al. Five-year outcome of characterized chondrocyte implantation versus 33 microfracture for symptomatic cartilage defects of the knee: early treatment matters. *Am J Sports Med* 39, 2566-2574, doi:10.1177/0363546511422220 (2011).

Piuzzi, N. S. et al. Accelerated Growth of Cellular Therapy Trials in Musculoskeletal Disorders: An Analysis of the NIH Clinical Trials Data Bank. *Orthopedics,* 1-7, doi:10.3928/01477447-20190118-04 (2019).

Sipp, D., Robey, P. G. & Turner, L. Clear up this stem-cell mess. *Nature* 561, 455-457, doi:10.1038/d41586-018-06756-9 (2018).

Jo, C. H. et al. Intra-articular injection of mesenchymal stem cells for the treatment of osteoarthritis of the knee: a proof-of-concept clinical trial. *Stem Cells* 32, 1254-1266, doi:10.1002/stem.1634 (2014).

Vega, A. et al. Treatment of Knee Osteoarthritis With Allogeneic Bone Marrow Mesenchymal Stem Cells: A Randomized Controlled Trial. *Transplantation* 99, 1681-1690, doi:10.1097/TP.0000000000000678 (2015).

Pers, Y. M. et al. Adipose Mesenchymal Stromal Cell-Based Therapy for Severe Osteoarthritis of the Knee: A Phase I Dose-Escalation Trial. *Stem Cells Transl Med* 5, 847-856, doi:10.5966/sctm.2015-0245 (2016).

Worthley, D. L. et al. Gremlin 1 identifies a skeletal stem cell with bone, cartilage, and reticular stromal potential. *Cell* 160, 269-284, doi:10.1016/j.cell.2014.11.042 (2015).

Sacchetti, B. et al. Self-renewing osteoprogenitors in bone marrow sinusoids can organize a hematopoietic microenvironment. *Cell* 131, 324-336, doi:10.1016/j.cell.2007.08.025 (2007).

Chan, C. K. et al. Identification and specification of the mouse skeletal stem cell. *Cell* 160, 285-298, doi:10.1016/j.cell.2014.12.002 (2015).

Chan, C. K. F. et al. Identification of the Human Skeletal Stem Cell. *Cell* 175, 43-56 e21, doi:10.1016/j.cell.2018.07.029 (2018).

Ambrosi, T. H., Longaker, M. T. & Chan, C. K. F. A Revised Perspective of Skeletal Stem Cell Biology. *Front Cell Dev Biol* 7, 189, doi:10.3389/fcell.2019.00189 (2019).

Luria, E. A., Owen, M. E., Friedenstein, A. J., Morris, J. F. & Kuznetsow, S. A. Bone formation in organ cultures of bone marrow. *Cell Tissue Res* 248, 449-454, doi:10.1007/bf00218212 (1987).

Gronthos, S., Simmons, P. J., Graves, S. E. & Robey, P. G. Integrin-mediated interactions between human bone marrow stromal precursor cells and the extracellular matrix. *Bone* 28, 174-181, doi:10.1016/s8756-3282(00)00424-5 (2001).

Kratchmarova, I., Blagoev, B., Haack-Sorensen, M., Kassem, M. & Mann, M. Mechanism of divergent growth factor effects in mesenchymal stem cell differentiation. *Science* 308, 1472-1477, doi:10.1126/science.1107627 (2005).

Marecic, O. et al. Identification and characterization of an injury-induced skeletal progenitor. *Proc Natl Acad Sci USA* 112, 9920-9925, doi:10.1073/pnas.1513066112 (2015).

Jiang, Y. & Tuan, R. S. Origin and function of cartilage stem/progenitor cells in osteoarthritis. *Nat Rev Rheumatol* 11, 206-212, doi:10.1038/nrrheum.2014.200 (2015).

Ransom, R. C. et al. Genetic dissection of clonal lineage relationships with hydroxytamoxifen liposomes. *Nat Commun* 9, 2971, doi:10.1038/s41467-018-05436-6 (2018).

Loeser, R. F., Collins, J. A. & Diekman, B. O. Ageing and the pathogenesis of osteoarthritis. *Nat Rev Rheumatol* 12, 412-420, doi:10.1038/nrrheum.2016.65 (2016).

Gulati, G. S. et al. Isolation and functional assessment of mouse skeletal stem cell lineage. *Nat Protoc* 13, 1294-1309, doi:10.1038/nprot.2018.041 (2018).

Eldracher, M., Orth, P., Cucchiarini, M., Pape, D. & Madry, H. Small subchondral drill holes improve marrow stimulation of articular cartilage defects. *Am J Sports Med* 42, 2741-2750, doi:10.1177/0363546514547029 (2014).

Rinkevich, Y., Lindau, P., Ueno, H., Longaker, M. T. & Weissman, I. L. Germ-layer and lineage-restricted stem/progenitors regenerate the mouse digit tip. *Nature* 476, 409-413, doi:10.1038/nature10346 (2011).

Fang, H. & Beier, F. Mouse models of osteoarthritis: modelling risk factors and assessing outcomes. *Nat Rev Rheumatol* 10, 413-421, doi:10.1038/nrrheum.2014.46 (2014).

Loeser, R. F. et al. Microarray analysis reveals age-related differences in gene expression during the development of osteoarthritis in mice. *Arthritis Rheum* 64, 705-717, doi:10.1002/art.33388 (2012).

Ransom, R. C. et al. Mechanoresponsive stem cells acquire neural crest fate in jaw regeneration. *Nature* 563, 514-521, doi:10.1038/s41586-018-0650-9 (2018).

Ray, A., Singh, P. N., Sohaskey, M. L., Harland, R. M. & Bandyopadhyay, A. Precise spatial restriction of BMP signaling is essential for articular cartilage differentiation. *Development* 142, 1169-1179, doi:10.1242/dev.110940 (2015).

Bragdon, B. et al. Earliest phases of chondrogenesis are dependent upon angiogenesis during ectopic bone formation in mice. *Bone* 101, 49-61, doi:10.1016/j.bone.2017.04.002 (2017).

Urist, M. R. Bone: formation by autoinduction. *Science* 150, 893-899 (1965).

Sun, T. et al. Loading of BMP2 related peptide onto three-dimensional nanohydroxyapatite scaffolds accelerates mineralization in critical-sized cranial bone defects. *J Tissue Eng Regen Med*, doi:10.1002/term.2371 (2016).

Keeney, M. et al. Scaffold-mediated BMP-2 minicircle DNA delivery accelerated bone repair in a mouse critical-size calvarial defect model. *J Biomed Mater Res A* 104, 2099-2107, doi:10.1002/jbm.a.35735 (2016).

Chung, H. J. et al. Anti-Osteoporotic Activity of Harpagoside by Upregulation of the BMP2 and Wnt Signaling Pathways in Osteoblasts and Suppression of Differentiation in Osteoclasts. *J Nat Prod* 80, 434-442, doi:10.1021/acs.jnatprod.6b00964 (2017).

Gonzalez-Fernandez, T., Tierney, E. G., Cunniffe, G. M., O'Brien, F. J. & Kelly, D. J. Gene Delivery of TGF-beta3 and BMP2 in an MSC-Laden Alginate Hydrogel for Articular Cartilage and Endochondral Bone Tissue Engineering. *Tissue Eng Part A* 22, 776-787, doi:10.1089/ten.TEA.2015.0576 (2016).

Hamilton, J. L. et al. Targeting VEGF and Its Receptors for the Treatment of Osteoarthritis and Associated Pain. *J Bone Miner Res* 31, 911-924, doi:10.1002/jbmr.2828 (2016).

Nagai, T. et al. Bevacizumab, an anti-vascular endothelial growth factor antibody, inhibits osteoarthritis. *Arthritis Res Ther* 16, 427, doi:10.1186/s13075-014-0427-y (2014). 51 Tevlin, R. et al. Pharmacological rescue of diabetic skeletal stem cell niches. *Sci Transl Med* 9, doi:10.1126/scitranslmed.aag2809 (2017).

Adouni, M. & Dhaher, Y. Y. A multi-scale elasto-plastic model of articular cartilage. *J Biomech* 49, 2891-2898, doi:10.1016/j.jbiomech.2016.06.031 (2016).

Chandran, P. L., Dimitriadis, E. K., Mertz, E. L. & Horkay, F. Microscale mapping of extracellular matrix elasticity of mouse joint cartilage: an approach to extracting bulk elasticity of soft matter with surface roughness. *Soft Matter* 14, 2879-2892, doi:10.1039/c7sm02045g (2018).

Kretzschmar, K. et al. Profiling proliferative cells and their progeny in damaged murine hearts. *Proc Natl Acad Sci USA* 115, E12245-E12254, doi:10.1073/pnas.1805829115 (2018).

Nagao, M. et al. Vascular Endothelial Growth Factor in Cartilage Development and Osteoarthritis. *Sci Rep* 7, 13027, doi:10.1038/s41598-017-13417-w (2017).

Steinberg, J. & Zeggini, E. Functional genomics in osteoarthritis: Past, present, and future. *J Orthop Res* 34, 1105-1110, doi:10.1002/jor.23296 (2016).

Prockop, D. J. et al. Defining the risks of mesenchymal stromal cell therapy. *Cytotherapy* 12, 576-578, doi:10.3109/14653249.2010.507330 (2010).

Jones, I. A., Togashi, R., Wilson, M. L., Heckmann, N. & Vangsness, C. T., Jr. Intraarticular treatment options for knee osteoarthritis. *Nat Rev Rheumatol* 15, 77-90, doi:10.1038/s41584-018-0123-4 (2019).

Conrad, B., Han, L. H. & Yang, F. Gelatin-Based Microribbon Hydrogels Accelerate Cartilage Formation by Mesenchymal Stem Cells in Three Dimensions. *Tissue Eng Part A* 24, 1631-1640, doi:10.1089/ten.TEA.2018.0011 (2018).

Taylor, S. E. et al. Identification of Human Juvenile Chondrocyte-Specific Factors that Stimulate Stem Cell Growth. *Tissue Eng Part A* 22, 645-653, doi:10.1089/ten.TEA.2015.0366 (2016).

What is claimed is:

1. A method for regenerating human articular cartilage in a subject with diminished chondrogenesis, the method comprising:

activating human skeletal stem cells with a combination of (i) a mechanical stimulus, and (ii) a biochemical stimulus, wherein the mechanical stimulus is a surgically performed microfracture procedure to bone tissue at a desired site for articular cartilage regeneration; and wherein the biochemical stimulus is a combination of an effective dose of human BMP2 protein and a VEGF inhibitor.

2. The method of claim 1, wherein the biochemical stimulus is provided within 3 days of the mechanical stimulus.

3. The method of claim 1, wherein the VEGF inhibitor is cabozantinib.

4. The method of claim 1, wherein the human BMP2 protein and the VEGF inhibitor are provided in a drug delivery device.

5. The method of claim 4, wherein the drug delivery device comprises the human BMP2 protein and the VEGF inhibitor as the sole active agents.

6. The method of claim 4, wherein the drug delivery device is a biodegradable implant.

7. The method of claim 6, wherein the biodegradable implant is a block polymer implant.

8. The method of claim 6, wherein the biodegradable implant comprises poly(caprolactone) (PCL), poly(lactic acid) (PLA) or poly(lactic-co-glycolic acid) (PLGA).

9. The method of claim 6, wherein the biodegradable implant comprises one or more of polyethylene glycol, alginate, collagen, hyaluronic acid, cellulose, chitosan, silk, gelatin, albumin, or elastin.

10. The method of claim 6, wherein the biodegradable implant is a hydrogel.

11. The method of claim 4, wherein the drug delivery device is implanted at the site undergoing the surgically performed microfracture procedure in the absence of exogenous cells.

12. A method for regenerating human articular cartilage in an aged human, the method comprising:

activating human skeletal stem cells with a combination of (i) a mechanical stimulus, and (ii) a biochemical stimulus, wherein the mechanical stimulus is a surgically performed microfracture procedure to bone tissue at a desired site for articular cartilage regeneration;

wherein the biochemical stimulus is a combination of an effective dose of human BMP2 protein and a VEGF inhibitor, wherein human BMP2 protein is provided at a dose of from about 10 μg to 10 mg, and the VEGF inhibitor is provided at a dose of from about 0.1 μg to 50 mg; and wherein the biochemical stimulus is provided within 3 days of the mechanical stimulus.

13. The method of claim 12, wherein the VEGF inhibitor is cabozantinib.

14. A method for regenerating human articular cartilage in an individual with osteoarthritis, the method comprising:

activating human skeletal stem cells with a combination of (i) a mechanical stimulus, and (ii) a biochemical stimulus, wherein the mechanical stimulus is a surgically performed microfracture procedure to bone tissue at a desired site for articular cartilage regeneration;

wherein the biochemical stimulus is a combination of an effective dose of human BMP2 protein and a VEGF inhibitor, wherein the human BMP2 protein is provided at a dose of from about 10 μg to 10 mg, and the VEGF inhibitor is provided at a dose of from about 0.1 μg to 50 mg; and wherein the biochemical stimulus is provided within 3 days of the mechanical stimulus.

15. The method of claim 14, wherein the VEGF inhibitor is cabozantinib.

* * * * *